(12) United States Patent
Yan et al.

(10) Patent No.: US 9,855,156 B2
(45) Date of Patent: Jan. 2, 2018

(54) BIODEGRADABLE ENDOPROSTHESES AND METHODS OF THEIR FABRICATION

(71) Applicant: Elixir Medical Corporation, Sunnyvale, CA (US)

(72) Inventors: John Yan, Los Gatos, CA (US); Vinayak Bhat, Cupertino, CA (US)

(73) Assignee: Elixir Medical Corporation, Milpitas, CA (US)

( * ) Notice: Subject to any disclaimer, the term of this patent is extended or adjusted under 35 U.S.C. 154(b) by 0 days.

(21) Appl. No.: 15/043,331

(22) Filed: Feb. 12, 2016

(65) Prior Publication Data

US 2016/0166414 A1 Jun. 16, 2016

Related U.S. Application Data

(63) Continuation-in-part of application No. 14/800,536, filed on Jul. 15, 2015, now Pat. No. 9,730,819, and a
(Continued)

(51) Int. Cl.
*A61F 2/06* (2013.01)
*A61F 2/89* (2013.01)
*A61F 2/915* (2013.01)

(52) U.S. Cl.
CPC ............... *A61F 2/89* (2013.01); *A61F 2/915* (2013.01); *A61F 2002/91558* (2013.01); *A61F 2002/91566* (2013.01); *A61F 2002/91575* (2013.01); *A61F 2210/0004* (2013.01); *A61F 2210/0014* (2013.01); *A61F 2230/001* (2013.01); *A61F 2230/0006* (2013.01); *A61F 2230/0008* (2013.01); *A61F 2230/0069* (2013.01); *A61F 2250/0036* (2013.01); *A61F 2250/0067* (2013.01)

(58) Field of Classification Search
CPC .... A61F 2/89; A61F 2/915; A61F 2/82; A61F 2/90; A61F 2/91; A61F 2/844
See application file for complete search history.

(56) References Cited

U.S. PATENT DOCUMENTS 3,867,190 A 2/1975 Schmitt et al.
5,298,276 A 3/1994 Jayaraman
(Continued)

FOREIGN PATENT DOCUMENTS

CN 1328853 A 1/2002
CN 1569270 A 1/2005
(Continued)

OTHER PUBLICATIONS

Bae, et al. Drug delivery. Fundamentals and methods of tissue engineering. From 'Frontiers in Tissue Engineering' edited by Patrick et al. Feb. 20, 1998; Ch II. 14:263-272.
(Continued)

*Primary Examiner* — Alvin Stewart
(74) *Attorney, Agent, or Firm* — Wilson Sonsini Goodrich & Rosati

(57) ABSTRACT

A biodegradable stent prosthesis formed from a degradable material, having a plurality of luminal, abluminal, and side surface regions, wherein a surface portion extending between the abluminal and luminal surface region of at least some structural elements is convex.

68 Claims, 13 Drawing Sheets

Related U.S. Application Data continuation-in-part of application No. 14/697,537, filed on Apr. 27, 2015, now Pat. No. 9,480,588, and a continuation-in-part of application No. 14/682,014, filed on Apr. 8, 2015, now Pat. No. 9,259,339, and a continuation-in-part of application No. 14/461,159, filed on Aug. 15, 2014, now Pat. No. 9,119,905.

(60) Provisional application No. 62/187,737, filed on Jul. 1, 2015.

(56) References Cited

U.S. PATENT DOCUMENTS

| | | | |
|---|---|---|---|
| 5,441,483 | A | 8/1995 | Avitall |
| 5,447,724 | A | 9/1995 | Helmus et al. |
| 5,449,384 | A | 9/1995 | Johnson |
| 5,500,013 | A | 3/1996 | Buscemi et al. |
| 5,607,466 | A | 3/1997 | Imbert et al. |
| 5,670,161 | A | 9/1997 | Healy et al. |
| 5,674,286 | A | 10/1997 | D'Alessio et al. |
| 5,741,329 | A | 4/1998 | Agrawal et al. |
| 5,902,333 | A | 5/1999 | Roberts et al. |
| 5,935,119 | A | 8/1999 | Guy et al. |
| 5,957,975 | A | 9/1999 | Lafont et al. |
| 5,964,798 | A | 10/1999 | Imran |
| 5,980,564 | A | 11/1999 | Stinson |
| 6,027,526 | A | 2/2000 | Limon et al. |
| 6,039,755 | A | 3/2000 | Edwin et al. |
| 6,120,847 | A | 9/2000 | Yang et al. |
| 6,190,405 | B1 | 2/2001 | Culombo et al. |
| 6,224,803 | B1 | 5/2001 | Tiernan |
| 6,245,103 | B1 | 6/2001 | Stinson |
| 6,251,134 | B1 | 6/2001 | Alt et al. |
| 6,322,847 | B1 | 11/2001 | Zhong et al. |
| 6,323,256 | B1 | 11/2001 | Delmain |
| 6,325,825 | B1 | 12/2001 | Kula et al. |
| 6,395,326 | B1 | 5/2002 | Castro et al. |
| 6,537,312 | B2 | 3/2003 | Datta et al. |
| 6,547,814 | B2 | 4/2003 | Edwin et al. |
| 6,585,755 | B2 | 7/2003 | Jackson et al. |
| 6,626,939 | B1 | 9/2003 | Burnside et al. |
| 6,652,582 | B1 | 11/2003 | Stinson |
| 6,719,934 | B2 | 4/2004 | Stinson |
| 6,726,701 | B2 | 4/2004 | Gilson et al. |
| 6,761,784 | B1 | 7/2004 | Hage |
| 6,773,455 | B2 | 8/2004 | Allen et al. |
| 6,774,278 | B1 | 8/2004 | Ragheb et al. |
| 6,776,796 | B2 | 8/2004 | Falotico et al. |
| 6,805,898 | B1 | 10/2004 | Wu et al. |
| 6,863,757 | B1 | 3/2005 | Gonzalez et al. |
| 6,896,695 | B2 | 5/2005 | Mueller et al. |
| 6,920,677 | B2 | 7/2005 | Dolan et al. |
| 6,997,948 | B2 | 2/2006 | Stinson |
| 7,001,421 | B2 | 2/2006 | Cheng et al. |
| 7,108,716 | B2 | 9/2006 | Burnside et al. |
| 7,153,322 | B2 | 12/2006 | Alt |
| 7,258,697 | B1 | 8/2007 | Cox et al. |
| 7,279,005 | B2 | 10/2007 | Stinson |
| 7,285,304 | B1 | 10/2007 | Hossainy et al. |
| 7,291,166 | B2 | 11/2007 | Cheng et al. |
| 7,329,366 | B1 | 2/2008 | Gale et al. |
| 7,354,450 | B2 | 4/2008 | Bicek et al. |
| 7,377,939 | B2 | 5/2008 | Wiliams et al. |
| 7,390,333 | B2 | 6/2008 | Dutta |
| 7,550,005 | B2 | 6/2009 | Bates et al. |
| 7,563,277 | B2 | 7/2009 | Case et al. |
| 7,572,287 | B2 | 8/2009 | Stinson |
| 7,594,928 | B2 | 9/2009 | Headley et al. |
| 7,618,448 | B2 | 11/2009 | Schmitz et al. |
| 7,622,070 | B2 | 11/2009 | Atladottir et al. |
| 7,666,342 | B2 | 2/2010 | Limon et al. |
| 7,731,890 | B2 | 6/2010 | Gale et al. |
| 7,758,636 | B2 | 7/2010 | Shanley et al. |
| 7,824,601 | B1 | 11/2010 | Stankus et al. |
| 7,829,008 | B2 | 11/2010 | Gueriguian et al. |
| 7,875,233 | B2 | 1/2011 | Huang et al. |
| 7,964,136 | B2 | 6/2011 | Sabaria |
| 7,967,998 | B2 | 6/2011 | Gale et al. |
| 7,971,333 | B2 | 7/2011 | Gale et al. |
| 8,043,553 | B1 | 10/2011 | Durcan |
| 8,057,534 | B2 | 11/2011 | Boismier et al. |
| 8,062,465 | B1 | 11/2011 | Huang et al. |
| 8,172,897 | B2 | 5/2012 | Gale et al. |
| 8,173,062 | B1 | 5/2012 | Durcan |
| 8,182,890 | B2 | 5/2012 | Zheng et al. |
| 8,241,554 | B1 | 8/2012 | Abbate et al. |
| 8,268,228 | B2 | 9/2012 | Huang et al. |
| 8,323,760 | B2 | 12/2012 | Zheng et al. |
| 8,425,587 | B2 | 4/2013 | Trollsas et al. |
| 8,501,079 | B2 | 8/2013 | Glauser et al. |
| 8,545,546 | B2 | 10/2013 | Wang |
| 8,562,670 | B2 | 10/2013 | Pacetti et al. |
| 8,636,792 | B2 | 1/2014 | Zheng et al. |
| 8,709,071 | B1* | 4/2014 | Huang ............... A61L 31/08 623/1.42 |
| 8,740,839 | B2* | 6/2014 | Eaton ............... A61B 17/24 604/104 |
| 8,778,256 | B1 | 7/2014 | Huang et al. |
| 8,795,030 | B2 | 8/2014 | Huang et al. |
| 8,814,930 | B2 | 8/2014 | Zheng et al. |
| 8,834,556 | B2 | 9/2014 | Papp et al. |
| 8,840,660 | B2 | 9/2014 | Weber |
| 8,852,263 | B2 | 10/2014 | Wang |
| 8,872,062 | B2 | 10/2014 | Chen et al. |
| 8,900,292 | B2* | 12/2014 | Gregorich ............... A61F 2/91 623/1.42 |
| 8,956,403 | B2 | 2/2015 | Gregorich et al. |
| 9,005,276 | B2 | 4/2015 | Fox et al. |
| 9,119,905 | B2* | 9/2015 | Zheng ............... A61F 2/82 |
| 9,259,339 | B1* | 2/2016 | Yan ............... A61L 31/06 |
| 9,480,588 | B2* | 11/2016 | Yan ............... A61L 31/06 |
| 9,566,371 | B2 | 2/2017 | Zheng et al. |
| 9,730,819 | B2 | 8/2017 | Yan et al. |
| 2001/0016729 | A1 | 8/2001 | Divino et al. |
| 2001/0016769 | A1 | 8/2001 | Hojeibane |
| 2001/0016770 | A1 | 8/2001 | Allen et al. |
| 2001/0021871 | A1 | 9/2001 | Stinson |
| 2001/0053929 | A1 | 12/2001 | Vonesh et al. |
| 2002/0007209 | A1 | 1/2002 | Scheerder et al. |
| 2002/0038146 | A1 | 3/2002 | Harry |
| 2002/0161430 | A1 | 10/2002 | Jang |
| 2002/0165597 | A1 | 11/2002 | Clerc et al. |
| 2002/0183581 | A1 | 12/2002 | Yoe et al. |
| 2002/0193336 | A1 | 12/2002 | Elkins et al. |
| 2003/0004563 | A1 | 1/2003 | Jackson et al. |
| 2003/0033007 | A1 | 2/2003 | Sirhan et al. |
| 2003/0050687 | A1 | 3/2003 | Schwade et al. |
| 2003/0050692 | A1 | 3/2003 | Sirhan et al. |
| 2003/0064097 | A1 | 4/2003 | Patel et al. |
| 2003/0083732 | A1 | 5/2003 | Stinson |
| 2003/0088307 | A1* | 5/2003 | Shulze ............... A61F 2/91 623/1.15 |
| 2003/0093143 | A1 | 5/2003 | Zhao et al. |
| 2003/0144726 | A1 | 7/2003 | Majercak et al. |
| 2003/0144729 | A1 | 7/2003 | Bicek et al. |
| 2003/0199993 | A1 | 10/2003 | Gellman et al. |
| 2003/0236320 | A1 | 12/2003 | Martin et al. |
| 2004/0006382 | A1 | 1/2004 | Sohier |
| 2004/0073290 | A1 | 4/2004 | Chouinard |
| 2004/0147999 | A1 | 7/2004 | Udipi et al. |
| 2004/0199242 | A1 | 10/2004 | Hong et al. |
| 2005/0031704 | A1 | 2/2005 | Ahn |
| 2005/0060020 | A1 | 3/2005 | Jenson |
| 2005/0070991 | A1 | 3/2005 | Pienknagura |
| 2005/0070996 | A1 | 3/2005 | Dinh et al. |
| 2005/0075625 | A1 | 4/2005 | Dao et al. |
| 2005/0075716 | A1 | 4/2005 | Yan |
| 2005/0123588 | A1 | 6/2005 | Zhu et al. |
| 2005/0125051 | A1 | 6/2005 | Eidenschink et al. |
| 2005/0171595 | A1 | 8/2005 | Feldman et al. |
| 2005/0187615 | A1 | 8/2005 | Williams et al. |
| 2005/0209680 | A1 | 9/2005 | Gale et al. |
| 2005/0216074 | A1 | 9/2005 | Sahatjian et al. |
| 2005/0232964 | A1 | 10/2005 | Fennimore et al. |

(56) References Cited

U.S. PATENT DOCUMENTS

| | | |
|---|---|---|
| 2006/0025852 A1 | 2/2006 | Armstrong et al. |
| 2006/0076708 A1 | 4/2006 | Huang et al. |
| 2006/0100695 A1 | 5/2006 | Peacock |
| 2006/0111485 A1 | 5/2006 | Laghi |
| 2006/0122697 A1 | 6/2006 | Shanley et al. |
| 2006/0129222 A1 | 6/2006 | Stinson |
| 2006/0136048 A1 | 6/2006 | Pacetti et al. |
| 2006/0147538 A1 | 7/2006 | Craig et al. |
| 2006/0193892 A1 | 8/2006 | Furst et al. |
| 2006/0229711 A1 | 10/2006 | Yan et al. |
| 2006/0251618 A1 | 11/2006 | Dennis et al. |
| 2006/0265048 A1 | 11/2006 | Cheng et al. |
| 2006/0271170 A1 | 11/2006 | Gale et al. |
| 2006/0287710 A1 | 12/2006 | Lendlein et al. |
| 2007/0023974 A1 | 2/2007 | Wu |
| 2007/0129789 A1 | 6/2007 | Cottone et al. |
| 2007/0231365 A1 | 10/2007 | Wang et al. |
| 2007/0253999 A1 | 11/2007 | Huang et al. |
| 2007/0259099 A1 | 11/2007 | Van Sciver |
| 2007/0270941 A1 | 11/2007 | Headley et al. |
| 2007/0271763 A1 | 11/2007 | Huang et al. |
| 2007/0278720 A1 | 12/2007 | Wang et al. |
| 2007/0281117 A1* | 12/2007 | Kaplan ............... A61F 2/91 428/35.7 |
| 2007/0282426 A1 | 12/2007 | Wang et al. |
| 2007/0282434 A1 | 12/2007 | Wang et al. |
| 2007/0283552 A1 | 12/2007 | Gale et al. |
| 2007/0290412 A1 | 12/2007 | Capek et al. |
| 2007/0299505 A1 | 12/2007 | Gregorich et al. |
| 2008/0051866 A1 | 2/2008 | Chen et al. |
| 2008/0081063 A1 | 4/2008 | Wang et al. |
| 2008/0082162 A1* | 4/2008 | Boismier ............ A61F 2/91 623/1.38 |
| 2008/0097571 A1 | 4/2008 | Denison et al. |
| 2008/0097580 A1 | 4/2008 | Dave |
| 2008/0103584 A1 | 5/2008 | Su et al. |
| 2008/0147165 A1 | 6/2008 | Hossainy et al. |
| 2008/0177373 A1 | 7/2008 | Huang et al. |
| 2008/0177374 A1 | 7/2008 | Zheng et al. |
| 2008/0243243 A1 | 10/2008 | Williams et al. |
| 2008/0249608 A1 | 10/2008 | Dave |
| 2008/0306579 A1 | 12/2008 | Dolan et al. |
| 2009/0030507 A1 | 1/2009 | Klocke et al. |
| 2009/0095715 A1 | 4/2009 | Sabaria |
| 2009/0096137 A1 | 4/2009 | Williams et al. |
| 2009/0099639 A1 | 4/2009 | Sabaria |
| 2009/0105800 A1 | 4/2009 | Sabaria |
| 2009/0146348 A1 | 6/2009 | Huang et al. |
| 2009/0208555 A1 | 8/2009 | Kuttler et al. |
| 2009/0216309 A1 | 8/2009 | Granada et al. |
| 2009/0228094 A1 | 9/2009 | Yan et al. |
| 2010/0036478 A1 | 2/2010 | Wang et al. |
| 2010/0038822 A1 | 2/2010 | Wang et al. |
| 2010/0049300 A1* | 2/2010 | Harder ............... A61F 2/91 623/1.15 |
| 2010/0198331 A1 | 8/2010 | Rapoza et al. |
| 2010/0217370 A1 | 8/2010 | Scheuermann et al. |
| 2010/0244329 A1 | 9/2010 | Hossainy et al. |
| 2010/0252965 A1 | 10/2010 | Wang et al. |
| 2010/0262224 A1 | 10/2010 | Kleiner |
| 2010/0292773 A1 | 11/2010 | Schmid et al. |
| 2011/0022163 A1 | 1/2011 | Wang et al. |
| 2011/0054591 A1 | 3/2011 | Sahatjian et al. |
| 2011/0062638 A1 | 3/2011 | Glauser et al. |
| 2011/0160757 A1 | 6/2011 | Ferrera et al. |
| 2011/0215505 A1 | 9/2011 | Kleiner et al. |
| 2011/0238158 A1 | 9/2011 | Heringes et al. |
| 2011/0238162 A1 | 9/2011 | Busold et al. |
| 2011/0260352 A1 | 10/2011 | Tang et al. |
| 2011/0260358 A1 | 10/2011 | Wang et al. |
| 2012/0071962 A1 | 3/2012 | Huang et al. |
| 2012/0187606 A1 | 7/2012 | Zheng et al. |
| 2012/0226345 A1 | 9/2012 | Zheng et al. |
| 2012/0271396 A1 | 10/2012 | Zheng et al. |
| 2012/0290070 A1 | 11/2012 | Wang et al. |
| 2012/0290071 A1 | 11/2012 | Wang et al. |
| 2013/0084322 A1 | 4/2013 | Wu |
| 2013/0085564 A1 | 4/2013 | Papp et al. |
| 2013/0150943 A1 | 6/2013 | Zheng et al. |
| 2013/0190676 A1 | 7/2013 | Dickinson et al. |
| 2013/0331927 A1 | 12/2013 | Zheng et al. |
| 2014/0004312 A1 | 1/2014 | Foreman et al. |
| 2014/0012362 A1 | 1/2014 | Gale et al. |
| 2014/0018903 A1 | 1/2014 | Eli et al. |
| 2014/0025161 A1 | 1/2014 | Stankus et al. |
| 2014/0081381 A1 | 3/2014 | Kim |
| 2014/0114398 A1 | 4/2014 | Hossainy et al. |
| 2014/0121294 A1 | 5/2014 | Huang et al. |
| 2014/0188243 A1 | 7/2014 | Zheng et al. |
| 2014/0252683 A1 | 9/2014 | Huang et al. |
| 2014/0277373 A1 | 9/2014 | Huang et al. |
| 2014/0350659 A1 | 11/2014 | Zheng et al. |
| 2015/0025619 A1 | 1/2015 | Zheng et al. |
| 2015/0073536 A1 | 3/2015 | Rapoza et al. |
| 2015/0320577 A1 | 11/2015 | Zheng et al. |
| 2015/0374521 A1 | 12/2015 | Zheng et al. |
| 2016/0045343 A1 | 2/2016 | Yan et al. |
| 2016/0045344 A1* | 2/2016 | Yan .................. A61F 2/915 623/1.16 |
| 2016/0166414 A1* | 6/2016 | Yan ................... A61F 2/89 623/1.16 |
| 2016/0213499 A1 | 7/2016 | Zheng et al. |
| 2016/0278952 A1 | 9/2016 | Ngo et al. |
| 2016/0278953 A1 | 9/2016 | Zheng et al. |
| 2017/0156899 A1 | 6/2017 | Zheng et al. |

FOREIGN PATENT DOCUMENTS

| | | |
|---|---|---|
| JP | H11512626 A | 11/1999 |
| JP | 2000202032 A | 7/2000 |
| JP | 2003500101 A | 1/2003 |
| JP | 2004149692 A | 5/2004 |
| JP | 2005298617 A | 10/2005 |
| JP | 2006504467 A | 2/2006 |
| JP | 2006192111 A | 7/2006 |
| JP | 2006223860 A | 8/2006 |
| JP | 2009538688 A | 11/2009 |
| JP | 2011502008 A | 1/2011 |
| JP | 2011502195 A | 1/2011 |
| WO | WO-9204393 A1 | 3/1992 |
| WO | WO-0195834 A1 | 12/2001 |
| WO | WO-02091956 A1 | 11/2002 |
| WO | WO-03034940 A2 | 5/2003 |
| WO | WO-2004052420 A2 | 6/2004 |
| WO | WO-2004080332 A2 | 9/2004 |
| WO | WO-2004110315 A1 | 12/2004 |
| WO | WO-2004110515 A1 | 12/2004 |
| WO | WO-2004080332 A3 | 4/2005 |
| WO | WO-2005096992 A1 | 10/2005 |
| WO | WO-2005115277 A2 | 12/2005 |
| WO | WO-2005115277 A3 | 5/2007 |
| WO | WO-2007126599 A2 | 11/2007 |
| WO | WO-2007146354 A2 | 12/2007 |
| WO | WO-2008002479 A2 | 1/2008 |
| WO | WO-2008002636 A2 | 1/2008 |
| WO | WO-2008005390 A1 | 1/2008 |
| WO | WO-2008008416 A1 | 1/2008 |
| WO | WO-2008011048 A2 | 1/2008 |
| WO | WO-2007146354 A3 | 2/2008 |
| WO | WO-2008016667 A2 | 2/2008 |
| WO | WO-2008016696 A2 | 2/2008 |
| WO | WO-2008016696 A3 | 3/2008 |
| WO | WO-2008033263 A2 | 3/2008 |
| WO | WO-2008002636 A3 | 4/2008 |
| WO | WO-2008051867 A2 | 5/2008 |
| WO | WO-2007126599 A3 | 7/2008 |
| WO | WO-2008089434 A2 | 7/2008 |
| WO | WO-2008051867 A3 | 8/2008 |
| WO | WO-2008098434 A1 | 8/2008 |
| WO | WO-2008002479 A3 | 9/2008 |
| WO | WO-2008016667 A3 | 11/2008 |
| WO | WO-2008137821 A1 | 11/2008 |
| WO | WO-2008011048 A3 | 3/2009 |
| WO | WO-2008033263 A3 | 4/2009 |

(56) References Cited

FOREIGN PATENT DOCUMENTS

| WO | WO-2011025945 A1 | 3/2011 |
|----|------------------|--------|
| WO | WO-2014045068 A1 | 3/2014 |
| WO | WO-2014091438 A2 | 6/2014 |

OTHER PUBLICATIONS

Breiby, et al. Quantification of preferential orientation in conjugated polymers using X-ray diffraction. J. Polymer Science Part B: Polymer Physics. 2003; 41(20):2375-2393.
Co-pending U.S. Appl. No. 14/604,621, filed Jan. 23, 2015.
Cruz, et al. Quantitative mapping of the orientation of fibroin beta-sheets in B. mori cocoon fibers by scanning transmission X-ray microscopy. Biomacromolecules. Mar. 2006;7(3):836-43.
Donald, et al. Electron Microscopy of Banded Structures in Oriented Thermotropic Polymers. J. Materials Science. 1983; 18:1143-1150.
European search report and search opinion dated Feb. 18, 2015 for EP Application No. 12804895.6.
European search report and search opinion dated Dec. 20, 2012 for Application No. 8727927.9.
Fuhrman, et al. Central nervous system. From 'Tissue Engineering: From Lab to Clinic' edited by Pallua et al. 2010; Ch12:221-244.
Hacker, et al. Synthetic polymers. From 'Principles of Regenerative Medicine 2nd ed.' Edited by Atala et al. 2011; Ch 33:587-622.
Hara. Ion-containing polymers and their biological interactions. Polyelectrolytes Science and Technology. 1993; Ch 6:321-325.
Hombreiro-Perez, et al. Non-degradable microparticles containing a hydrophilic and/or a lipophilic drug: preparation, characterization and drug release modeling. J Control Release. Mar. 26, 2003;88(3):413-28.
International search report and written opinion dated Apr. 13, 2015 for PCT/US2015/012780.
International search report and written opinion dated Aug. 1, 2008 for PCT/US2008/051479.
International search report and written opinion dated Aug. 1, 2008 for PCT/US2008/051497.
International search report and written opinion dated Sep. 25, 2012 for PCT/US2012/44736.
Lamberti, et al. Real-time orientation and crystallinity measurements during the isotactic polypropylene film-casting process. J. Polymer Science Part B: Polymer Physics. 2003; 41(9):998-1008.
Lee, et al. Retardation of enzymatic degradation of microbial polyesters using surface chemistry: effect of addition of non-degradable polymers. Surface Science. 2003; 542(3):235-243.
Ma, et al. Scaffolding in Tissue Engineering. 2005; pp. 78-80.
Majoros, et al. Poly(amidoamine) dendrimer synthesis and characterization. Dendrimer-based Nanomedicine. 2008; Ch 3:35-57.
Notice of allowance dated May 12, 2014 for U.S. Appl. No. 13/897,302.
Notice of allowance dated Jul. 15, 2015 for U.S. Appl. No. 14/461,159.
Notice of allowance dated Dec. 13, 2013 for U.S. Appl. No. 13/539,770.
Notice of allowance dated Dec. 23, 2015 for U.S. Appl. No. 14/682,014.
Office action dated Mar. 2, 2010 for U.S. Appl. No. 12/016,077.
Office action dated Mar. 10, 2016 for U.S. Appl. No. 14/611,043.
Office action dated Mar. 28, 2016 for U.S. Appl. No. 14/697,537.
Office action dated Mar. 30, 2011 for U.S. Appl. No. 12/016,085.
Office action dated Apr. 1, 2011 for U.S. Appl. No. 12/016,077.
Office action dated Apr. 24, 2015 for U.S. Appl. No. 14/461,159.
Office action dated Jul. 2, 2013 for U.S. Appl. No. 12/016,077.
Office action dated Jul. 12, 2012 for U.S. Appl. No. 13/473,354.
Office action dated Jul. 15, 2015 for U.S. Appl. No. 14/682,014.
Office action dated Jul. 17, 2013 for U.S. Appl. No. 13/539,770.
Office action dated Aug. 1, 2014 for U.S. Appl. No. 14/097,087.
Office action dated Oct. 4, 2012 for U.S. Appl. No. 13/539,770.
Office action dated Oct. 27, 2011 for U.S. Appl. No. 12/016,077.
Office action dated Nov. 10, 2010 for U.S. Appl. No. 12/016,077.
Office action dated Nov. 14, 2014 for U.S. Appl. No. 14/461,159.
Office action dated Dec. 5, 2012 for U.S. Appl. No. 12/016,077.
Office action dated Dec. 15, 2011 for U.S. Appl. No. 12/016,085.
Office action dated Dec. 18, 2013 for U.S. Appl. No. 13/897,302.
Qin, et al. Synthesis and Characterization of Unsaturated Thermotropic Polyesters Prepared via Acyclic Diene Metathesis Polymerization. Macromolecules. 2004; 37:5239-5249.
Sanders. Controlled delivery systems for peptides. From 'Peptide and protein drug delivery' Edited by Vincent Lee, Advances in Parenteral science vol. 4. 1990; Ch 19:785-806.
Seal, et al. Polymeric biomaterials for tissue and organ regeneration. Materials Science and Engineering. R34. 2001; 147-230.
Shastri. Non-degradable biocompatible polymers in medicine: past, present, and future. Current Pharmaceutical Biotechnology. 2003; 4:331-337.
Tanimoto, et al. Comparison of in vivo acute stent recoil between the bioabsorbable everolimus-eluting coronary stent and the everolimus-eluting cobalt chromium coronary stent: insights from the ABSORB and SPIRIT trials. Catheter Cardiovasc Interv. Oct. 1, 2007;70(4):515-23.
Valimaa, et al. Viscoelastic memory and self-expansion of self-reinforced bioabsorbable stents. Biomaterials. Sep. 2002;23(17):3575-82.
Weir, et al. Processing, Annealing and Sterilisation of Poly-L-Lactide. Biomaterials. 2004; 25:3939-3949.
International search report and written opinion dated Aug. 25, 2016 for PCT Application No. PCT/US2016/026821.
International search report and written opinion dated Oct. 7, 2014 for PCT Application No. PCT/US2014/038508.
Notice of allowance dated Sep. 8, 2016 for U.S. Appl. No. 14/697,537.
Office action dated Jul. 1, 2016 for U.S. Appl. No. 14/604,621.
Office action dated Aug. 10, 2016 for U.S. Appl. No. 14/804,415.
Office action dated Nov. 4, 2016 for U.S. Appl. No. 15/178,506.
Office action dated Nov. 21, 2016 for U.S. Appl. No. 14/800,536.
Notice of allowance dated Apr. 18, 2017 for U.S. Appl. No. 14/800,536.
Notice of allowance dated Dec. 13, 2016 for U.S. Appl. No. 14/804,415.
Office action dated Feb. 16, 2017 for U.S. Appl. No. 14/800,536.
Office action dated Mar. 10, 2017 for U.S. Appl. No. 14/604,621.
Office action dated Aug. 21, 2017 for U.S. Appl. No. 15/420,615.

* cited by examiner

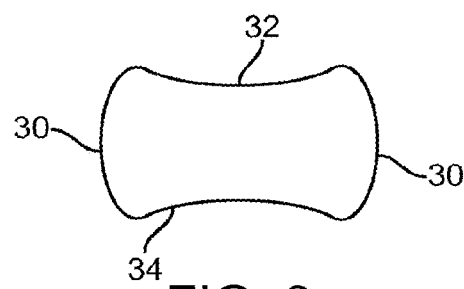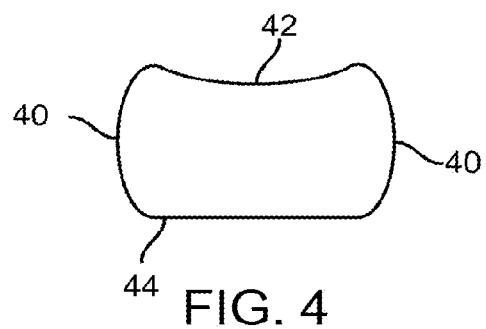
FIG. 3  FIG. 4
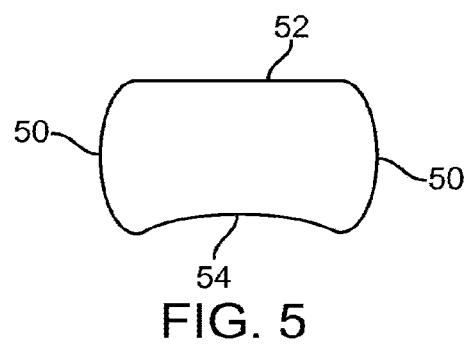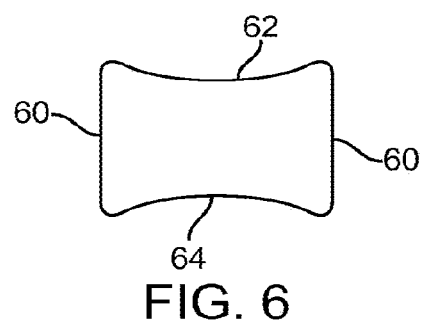
FIG. 5  FIG. 6
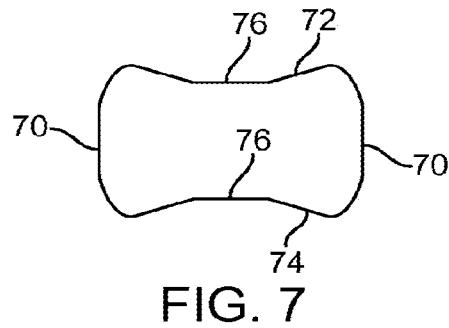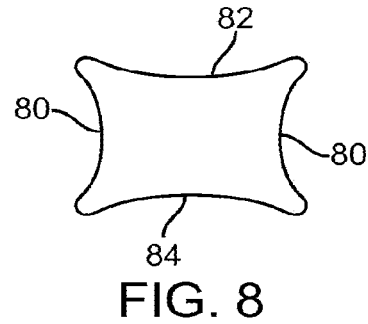
FIG. 7  FIG. 8
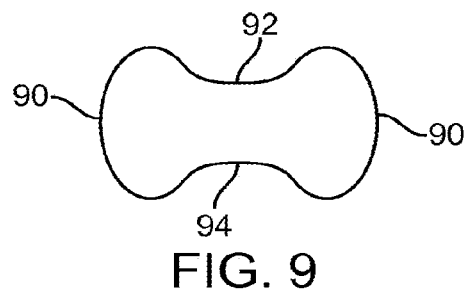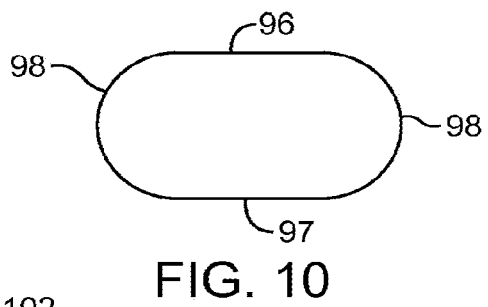
FIG. 9  FIG. 10
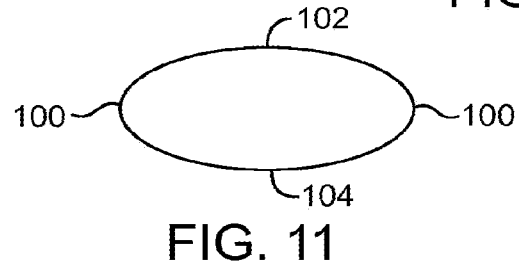
FIG. 11

BIODEGRADABLE ENDOPROSTHESES AND METHODS OF THEIR FABRICATION

CROSS-REFERENCE TO RELATED APPLICATIONS

This application is a continuation-in-part of U.S. patent application Ser. No. 14/800,536, filed Jul. 15, 2015, which claims priority to U.S. Provisional Patent Application No. 62/187,737, filed on Jul. 1, 2015; this application is also a continuation-in-part of U.S. patent application Ser. No. 14/697,537, filed Apr. 27, 2015, which is a continuation-in-part of U.S. patent application Ser. No. 14/682,014, filed Apr. 8, 2015, which is a continuation-in-part of U.S. patent application Ser. No. 14/461,159, filed Aug. 15, 2014, all of which are incorporated herein by reference.

FIELD OF THE INVENTION

The present invention relates generally to medical devices and methods for their fabrication. In particular, the present invention relates to the fabrication of biodegradable endoprostheses, such as stent prostheses, having shaped surface regions for enhanced implantation performance, enhanced drug delivery or other enhanced properties.

Stents are generally tubular-shaped devices which function to hold open or reinforce a segment of a blood vessel or body lumen, such as a coronary artery, carotid artery, saphenous vein graft, or femoral artery. They also are suitable to support and hold back a dissected arterial lining that could otherwise occlude the body lumen, to stabilize plaque, or to support/hold open a bioprosthetic valves. Stents can be formed from various materials, particularly polymeric and/or metallic materials, and may be non-degradable or biodegradable. Stents are typically delivered to the target area within the body lumen using a catheter. With balloon-expandable stents, the stent is mounted onto a balloon catheter, navigated to the appropriate area, and the stent is expanded by inflating the balloon. A self-expanding stent is delivered to the target area and released, expanding to treat the disease.

Of particular interest to the present invention are biodegradable stents, including polymer stents, such as biodegradable polymer stents or also called scaffolds and other endoprostheses. Biodegradable stents are usually formed from polymers which degrade by various mechanisms such as by hydrolysis and other reaction mechanisms in the vascular or other body environment. This invention also applies to metallic biodegradable stents.

Biodegradable polymer implantable devices and methods of making them are also described in commonly owned U.S. Pat. Nos. 8,182,890; 8,323,760; 8,636,792; 8,814,930; and U.S. Patent Publication Nos. 2008/0177373 and 2006/0029711 the entire disclosure of each of which is incorporated herein by reference.

BRIEF SUMMARY OF THE INVENTION

In embodiments of the disclosure an expandable biodegradable stent prosthesis comprises: a tubular expandable stent prosthesis body comprising a biodegradable material, for example a polymeric biodegradable material, said expandable stent prosthesis body comprising stent structural elements each having a luminal surface region and an abluminal surface region and a thickness between said luminal and abluminal surface regions; wherein a region extending between the abluminal surface region and the luminal surface region of at least some structural elements is bulbous.

In some embodiments two side surface regions extending between the luminal and abluminal surface regions of at least some stent structural elements are bulbous.

In embodiments of the disclosure an expandable biodegradable stent prosthesis comprises: an expandable stent prosthesis body comprising a biodegradable polymeric material, wherein the stent comprises a plurality of stent structural elements, wherein said stent structural elements each have a luminal surface region, an abluminal surface region, and two side surface regions extending between the luminal and abluminal surface regions; and wherein at least some of the stent structural elements have a bulbous shape coupling said abluminal and said luminal surface regions to form a dogbone shaped cross section.

In embodiments of the disclosure an expandable biodegradable stent prosthesis comprises: a tubular expandable stent prosthesis body comprising a biodegradable polymeric material, said expandable stent prosthesis body comprising stent structural elements each having a luminal surface region and an abluminal surface region and a thickness between said luminal and abluminal surface regions; wherein the thickness varies across the width of at least some of the structural elements.

In embodiments of the disclosure an expandable biodegradable stent prosthesis comprises a tubular expandable stent prosthesis body formed from a biodegradable, for example polymeric, material, said expandable stent prosthesis body comprising stent structural elements having luminal and abluminal surface regions; wherein at least some of the body abluminal surface regions are concave or flat across substantially their width. Said stent prosthesis may be expandable from a crimped configuration to an expanded larger configuration to support a blood vessel. At least some or substantially all of the side surface regions may be substantially convex. At least some or substantially all of the side surface regions which in use face the distal end of the delivery catheter may be substantially convex or completely convex.

The stent structural elements may for example comprise struts and crowns. The struts and crowns may each have an abluminal surface region and a luminal surface region. The stent structural elements may comprise struts, crowns, and links, each having an abluminal surface region and a luminal surface region. Each strut, crown, and link may have an abluminal surface region, a luminal surface region, and two side surface regions extending between the abluminal and luminal surface regions.

The expandable stent prosthesis body may comprise expandable serpentine rings, each ring may be composed of struts joined by crowns, and each ring may be connected to an adjacent ring by at least one link.

The struts and crowns may have two side surface regions extending between the luminal and abluminal surface regions, wherein at least some of the side surface regions are convex.

The expandable prosthesis may be formed of a biodegradable polymeric material which comprises at least two biodegradable polymers.

The expandable prosthesis body may have been treated to form the concave abluminal surface regions.

In embodiments of the disclosure an expandable biodegradable stent prosthesis comprises a tubular expandable stent prosthesis body comprising a biodegradable, for example polymeric material, said expandable stent prosthesis body comprising stent structural elements having luminal and abluminal surface regions; wherein at least some of the side surface regions are convex across substantially the thickness of said side surface regions. Said stent prosthesis may be expandable from a crimped configuration to an expanded larger configuration to support a blood vessel. Substantially all of the side surface region may be convex. At least some or substantially all of the side surface regions which in use face the distal end of the delivery catheter may be convex. At least some or substantially all of the abluminal surface regions may be concave, flat or straight, substantially across their width.

The convex side surface regions and concave, flat or straight abluminal surface regions may be prepared by treating to shape the stent structural elements or may be formed to have the desired shapes. The treatment may comprise shaping by application of a solvent by at least one of dipping, spraying, or contact with a solvent vapor. The treatment may alternatively or additionally comprise shaping by at least one of tumbling, agitating, deburring, scraping, media blasting, laser treatment and heat treatment.

The treatment may not significantly dissolve (or permanently remove) the polymeric material from which said prosthesis is formed. For example, the treatment may shift material from one stent structural element (also referred to herein as a stent structure) to an adjacent surface region of the same or different stent structural element without a substantial change in body weight or mass of said expandable stent prosthesis. The application of the solvent may soften the polymeric material allowing it to move, flow or redistribute from one surface region to another surface region on the stent structural elements without the polymeric material becoming dissolved in (or otherwise dispersed in) in the solvent.

The expandable stent prosthesis body may have been patterned from a tube by a laser. The expandable stent may have been patterned from a substantially continuous tubular body, substantially free from discontinuities or substantially free from holes.

The expandable stent prosthesis body may have been patterned from a tube by a laser and the stent structural elements treated to form the concave abluminal surface regions and convex side surface regions.

A coating comprising at least one drug may be formed over at least some portions of the expandable stent prosthesis body.

The stent prosthesis may further comprise a coating over the expandable stent prosthesis body with the coating such that concave surface regions of said stent structural elements remain substantially concave and convex surface regions of said stent structural elements remain substantially convex. Whatever shape the surface region has may remain substantially the same shape after the coating.

A weight or mass of the expandable stent prosthesis after treatment may be substantially the same as before treatment.

The biodegradable polymeric material may have an elastic modulus of at least 0.35 GPa.

The biodegradable polymeric material may comprise one or more of polymers and copolymers.

The prosthesis may be capable of being expanded from a crimped diameter to a deployed diameter at body temperature without fracture.

The prosthesis may be capable of being expanded from a crimped diameter to a deployed diameter at body temperature without substantial rotation of at least one of the stent structural elements about their axis.

The biodegradable polymeric material may comprise at least one material selected from the group consisting of lactides, poly-DL-Lactide, polylactide-co-gycolide, polylactide-co-polycaprolactone, poly (L-lactide-co-trimethylene carbonate), polytrimethylene carbonate, polyhydroxybutyrate, polyhydroxyvalerate, poly orthoesters, poly anhydrides, polylactide, polyglycolides, polycaprolactone, polyiminocarbonates and copolymers thereof.

The prosthesis may be balloon expandable.

The biodegradable polymeric material may have a molecular weight from 100 KDa to 1000 KDa.

The body may have been treated to adjust a thickness of at least one of the stent structural elements from a first thickness before treatment to a second thickness after treatment, wherein the second thickness is greater than the first thickness and the second thickness may vary across the width of the stent structural element.

The body may have been treated to cause a thickness of a plurality of stent structural elements between the luminal and abluminal surface regions to increase while a width of the stent structural elements between the side surface regions remains substantially the same.

The body may be treated by exposing the expandable prosthesis to a solvent for a predetermined period of time to provide at least some substantially convex side surface regions and at least some concave abluminal surface regions of said stent structural elements.

The body may have been treated to cause a thickness of the plurality of stent structural elements between the luminal and abluminal surface regions to increase while decreasing a minimum width of the stent structural elements between the side surface regions by redistributing the polymeric material.

In an embodiment, a stent prosthesis comprises a tubular expandable stent prosthesis body formed from a biodegradable material, such as a polymeric material, said material is patterned into a stent radially expandable from a crimped diameter to a deployed larger configuration, wherein the stent comprises a plurality of stent structural elements, such as struts joined by crowns, wherein said stent structural elements each have a luminal surface region, an abluminal surface region, and two side surface regions extending between the luminal and abluminal surface regions; and wherein at least some of the side surface regions have a convex shape across substantially the thickness of said side surface regions; said stent prosthesis in the deployed diameter has sufficient strength to support a blood vessel. The stent may comprise a plurality of stent structural elements such as struts joined by crowns where at least some of the crowns are connected to adjacent crowns by links or where at least some of the crowns are connected to adjacent crowns.

At least some of the stent structural element abluminal surface regions may have a concave shape across substantially their width. At least some of the stent structural element abluminal surface regions may have a surface shape similar to the surface of a dogbone, that is, a combination of convex and concave shapes across the width of the abluminal surface region.

Substantially all of the side surface regions may have a convex shape across substantially the thickness of said side surface regions.

The prosthesis may have been treated by contact with a solvent to redistribute said polymeric material to provide said concave or convex surface regions as the case may be.

The prosthesis may have been treated by contact with a solvent to flow said polymeric material to provide said concave or convex surface regions as the case may be.

In embodiments of the disclosure an expandable biodegradable stent prosthesis comprises a tubular expandable stent prosthesis body comprising a biodegradable metal or metal alloy, such as zinc, magnesium, and iron, and alloys thereof, wherein the stent is treated to modify at least some abluminal surface regions making them concave substantially across the width of said abluminal surface regions, and/or to modify at least some of side surface regions making them substantially convex across the thickness of said side surface regions. The above surface region modifications may be provided without a substantial change in weight or mass compared to before treatment, or without losing more than 15% in weight or mass after treatment, or without losing more than 25% in weight or mass after treatment. The metallic tubular body may be substantially continuous or substantially free from discontinuities or substantially free from holes before patterning.

The prosthesis may have been treated by contact with a solvent to redistribute said polymeric material to vary the thickness of at least one stent structural element and/or to vary the width of at least one stent structural element, for example to provide at least one stent structural element with a width that is larger away from than close to said abluminal and luminal surface regions and/or with a thickness that is smaller away from than close to the side surface regions.

In embodiments of the disclosure an expandable biodegradable stent prosthesis comprises a tubular expandable stent prosthesis body comprising a biodegradable polymeric material, wherein the tubular body has an initial diameter, which may be larger than an intended deployed diameter (labeled or nominal diameter) of the stent prosthesis (may be 1.1-1.5 times larger than intended deployed diameter). The tubular body may be patterned with a laser or by etching to provide stent structural elements, with the patterning preferably occurring at the initial diameter that is 1.1-1.5 times the intended deployed diameter. After patterning, some or all of the stent structural elements may be treated to provide a convex shape to at least some of the side surface regions and optionally a flat or concave shape to at least some of the abluminal surface regions. Said treatment may be performed at substantially the as-formed (initial) tubular diameter, The stent prosthesis may be treated by heating the polymeric material above Tg (the glass transition temperature) and below Tm (the melting point) of said polymeric material before or/and after the patterning of the stent prosthesis to provide or modify various physical properties of the resulting stent prosthesis. The stent structural elements may be heated to above Tg and below Tm of the polymeric material after said shaping treatment but before being crimped to a smaller diameter. The stent prosthesis is capable of being radially expanded or/and radially crimped and following insertion of the crimped prosthesis may be expanded to a deployed to a diameter larger than the crimped diameter to support a blood vessel or other body lumen without fracture.

In disclosed embodiments, a stent is formed from a substantially continuous body (or a body at least substantially free from holes and/or discontinuities), said body has been patterned into a stent body comprising stent structural elements each having at least two surface regions, said at least two surface regions are an abluminal surface region and a luminal surface region, wherein said stent structural elements have a thickness, wherein said thickness of at least some stent structural elements is variable across the width of said stent structural elements, wherein the thickness extends between the abluminal surface and luminal surface regions of a said stent structural element which may have a convex shape. In preferred embodiments, at least some structural elements have a larger thickness at about an end of their abluminal surface region than about a midpoint of their abluminal surface region. In some embodiments, the thickness at about an end of an abluminal region is smaller than that about a midpoint of the abluminal surface region. In preferred embodiments, the cross section of at least some stent structural elements is oval, or dogbone shape. In some embodiments, the maximum stent structural element thickness is at least 1.05 times the minimum stent structural element thickness. In some embodiments, the maximum stent structural element thickness ranges between 1.05-1.3 times the minimum stent structural element thickness. The minimum stent structural element thickness generally occurs near a center of the abluminal surface region.

In some embodiments, a stent is formed from a substantially continuous body (that is a body that is at least substantially free from holes and/or discontinuities), said body has been patterned into a stent body comprising stent structural elements each having at least two surface regions, said at least two surface regions are an abluminal surface region and a luminal surface region, wherein said structural elements have a thickness, wherein the surface area extending between the abluminal surface and luminal surface regions of the at least some stent structural elements is convex. In some embodiments, the abluminal surface region is substantially concave or substantially flat across the width of said stent structural element. In preferred embodiments, the cross section of at least some stent structural elements is oval or dogbone shape.

In a preferred embodiment, a degradable stent is formed from a substantially continuous body comprising a polymeric material, formed by extrusion, dipping, spraying, or molding, said body has been patterned after forming into a stent body comprising stent structural elements said structural elements comprising two surface regions, an abluminal surface region and a luminal surface region, wherein said structural elements have a thickness, wherein the region extending across the thickness between the abluminal surface and luminal surface regions of the at least some stent structural elements is bulbous in shape. The stent prosthesis may have a thickness that varies across the width of said structural elements. The stent prosthesis structural elements may have at least one side surface region wherein the side surface region is convex across substantially the thickness of said structural elements. The stent prosthesis abluminal surface region may have a concave shape across substantially the width of said structural elements or the width of the abluminal surface, said abluminal surface region may have a bulbous region about an end region or towards an end region of said structural element width, wherein said bulbous region may have a convex shape, wherein the bulbous region maximum thickness is greater than a minimum thickness across the width of said abluminal surface with the difference ranging from 3 micrometers to 100 micrometers, preferably 5 micrometers to 30 micrometers. The bulbous surface region coupling the abluminal and luminal surface regions may in some instances have a flat portion at about the middle of the bulbous or convex shape.

In some examples, wherein the stent prosthesis is treated to form the region having a bulbous shape, the bulbous region protrudes outwardly forming a convex shape.

A concave abluminal surface region minimizes or at least reduces the possibility of slippage of the stent when expanded to a deployed configuration, such that the structural elements hug the vessel wall or the plaque area better.

In some embodiments, the stent prosthesis is formed from a substantially continuous tubular body using extrusion, spraying, dipping, molding, or printing; said tubular body has been formed into a stent comprising a pattern of structural elements being radially expandable from a crimped configuration to an expanded larger configuration and have sufficient strength in the deployed configuration to support a body lumen; wherein, in cross section, surface regions extending between an abluminal surface region and a luminal surface region of at least some of said structural elements are bulbous; optionally wherein the thickness between the abluminal and luminal surfaces changes across the width of said abluminal surface regions wherein the thickest point is substantially towards the sides of said structural elements wherein the difference in thickness between said thickest point and thinnest point ranges between 1 micrometer and 15 micrometer, preferably between 2 micrometer and 10 micrometer, more preferably between 3 micrometer and 7 micrometer; wherein the stent structural elements are coated with a coating comprising a drug wherein the coating contours to said structural elements surface regions shapes wherein the thickness difference between the thickest point and the thinnest point across the width of said structural elements ranges between 1 micrometer and 15 micrometer, preferably ranges between 2 micrometer and 10 micrometer, more preferably ranges between 3 micrometer and 7 micrometer.

In some examples, in cross section, side surface regions of at least some structural elements extend outwardly forming a bulbous or convex region; wherein said convex region has a widest point and a narrowest point across the thickness of said structural elements and wherein the widest point is substantially about the center of said structural elements side surface regions, wherein the narrowest point is substantially about the ends of said structural elements side surface region, wherein the difference between the widest and narrowest point ranges between 4 micrometer and 30 micrometer, preferably ranges between 5 micrometer and 20 micrometer, most preferably ranges between 6 micrometer and 15 micrometer. Optionally, the abluminal surface region cross section is concave in shape with the difference between thickest and thinnest points of the structural element across the width of said abluminal surface region ranges between 1 micrometer and 10 micrometers. The thinnest point across the width is generally about at the center of the structural element.

In some examples, in cross section, at least some structural elements have a bulbous surface region extending between an abluminal surface region and a luminal surface region wherein the bulbous surface region comprises portions of the luminal and abluminal surface regions and side regions, wherein the bulbous surface regions forms variable thicknesses and widths across the thickness and widths of said structural elements; wherein said structural elements are coated with a coating comprising a drug and a polymer, wherein said coating contours to the shape of said surface regions maintaining a difference in thickness and widths across the thickness and widths of said structural elements cross sections.

In some examples, the abluminal surface of at least some structural elements may, in cross section, have a substantially concave shape across the width of the structural element, wherein the concave shape is formed between two bulbous surface regions.

In some examples, the stent prosthesis structural elements may have a coating comprising a mixture of drug and polymer, said coating being coated onto said structural elements wherein said coating contours to the shape of said structural elements abluminal, luminal, and side surfaces.

In some examples, the stent prosthesis structural elements may have a coating comprising a mixture of drug and polymer, said coating being coated onto said structural elements wherein said coating contours to the shape of said structural elements which have a substantially concave abluminal surface shape, a substantially concave luminal surface shape, and convex side surface shapes; said coating substantially maintaining or conforming to said concave abluminal surface shape, concave luminal surface shape, and convex side surface shapes.

In some examples, the coating may comprise a drug wherein the total drug dose ranges between 50 micrograms and 200 micrograms for an 18 mm stent prosthesis. In some examples the coating may comprise a drug wherein the total drug dose ranges between 2 micrograms per mm and 25 micrograms per mm.

In some examples, at least some abluminal surface regions have a lip or an edge across the abluminal surface region, wherein said lip or edge has a thickness that is different from the adjacent abluminal surface region, for example wherein the difference in thickness ranges between 2 micrometer and 10 micrometer.

In some examples, at least some structural elements abluminal surfaces are concave across the width of said abluminal surfaces extending along the length of said structural element.

In some examples at least some structural elements side surfaces are convex across the thickness of said side surfaces extending along the length of said side surfaces.

In some examples, at least some structural elements have concave abluminal surface, bulbous, dogbone, or convex side surface and a lip formed along the length of said structural element. In some examples, the concave luminal and/or abluminal surface regions join convex side surface regions at one or more lips which extend along the side or length of at least some of the structural elements. For example, the lips may extend continuously along a strut and a connected crown of the expandable stent prosthesis.

In some examples, the abluminal surface region has a convex shape across the width of said abluminal surface, while the luminal surface region has a convex, concave or substantially flat shape. In some examples both luminal and abluminal surface regions of said structural elements are substantially flat. In some examples both abluminal and luminal surface regions are convex wherein said structural element thickest point is about a midpoint across the abluminal and luminal surface regions, or wherein the structural element thickest point is about a midpoint across the width of said structural element. In some examples of any of the previous examples the side surface region extending between luminal and abluminal surface regions is convex.

In one example, the cross section of at least some of the stent structural elements such as struts and/or crowns have a maximum thickness at the middle of said strut and/or crown width, or have a maximum thickness near the middle of said strut and/or crown width, or have a maximum thickness about the middle of said strut and/or crown width, or have a maximum thickness between 0 to 25 micrometer offset from the middle of said strut and/or crown width, or have a maximum thickness between 1% and 15% of the middle of said strut and/or crown width. In another example, the middle of said strut and/or crown is the midpoint of said strut and/or crown width, or is the center of said strut and/or crown width, or is the mid-section of said strut and/or crown width. In some instances, the abluminal surface region of the struts and/or crowns forms a relatively uniform curved convex surface. In some instances of the struts and/or crown cross section there is one or more thickest points near the middle of the strut and/or crown width, that is, there is an indentation around the middle of the strut and/or crown with the two thickest regions of the structural element flanking each side of the indentation. The indentation may be at about the middle of the abluminal surface region or is offset from the middle in one direction or another. In some cases, the abluminal surface region is a convex curve with two bumps or additional convex curves along the top of the convex curve of the abluminal surface with a depression or indentation between the two bumps which bumps or raised sections form the thickest regions of the struts and/or crowns. These bumps may be symmetrical or non-symmetrical in both curvature and size or thickness. In one example, the cross section of at least some of the stent structural elements such as struts and/or crowns have a maximum thickness at about the middle of said strut and/or crown abluminal surface width. There may, in some instances, be a lip, ledge, or a rib extending along the side surface region of the struts and/or crowns located at about where the side surface regions meet the luminal surface regions and/or abluminal surface regions of the struts and/or crowns.

In a preferred example, the luminal surface of said strut and/or crowns is flat/straight, substantially flat/straight, concave, or substantially concave, across the width of said strut and/or crown. In one preferred example, the side surfaces extending between the abluminal and luminal surfaces are convex or substantially convex. In another example, the side surface extending between the luminal and abluminal surfaces are flat or substantially flat. In one preferred example, the luminal surface of said strut and/or crowns is substantially flat or concave across the width of said strut and/or crown, the side surfaces are flat or convex and the abluminal surface is convex so the thickest part of the struts and/or crowns falls at about the middle of the width of the struts and/or crowns. In one preferred example, the luminal surface of said strut and/or crowns is substantially flat across the width of said strut and/or crown, the side surfaces are convex and the abluminal surface is convex so the thickest part of the struts and/or crowns falls at about the middle of the width of the struts and/or crowns. In another preferred example, the luminal surface of said struts and/or crowns is substantially flat or substantially concave across the width of said strut and/or crown, the side surfaces are flat or convex and the abluminal surface is convex with an indentation at about the middle of the width of the abluminal surface region. In another preferred example, the luminal surface of said struts and/or crowns is substantially flat across the width of said strut and/or crown, the side surfaces are convex and the abluminal surface is convex with an indentation at about the middle of the width of the abluminal surface region.

In one example, the cross section of at least some of the stent structural elements, such as struts and/or crowns, has a maximum thickness at about the middle of said strut and/or crown width; the maximum thickness is located adjacent to a depression or indentation at about the middle of the strut and/or crown abluminal surface; or the maximum thickness is located adjacent to a depression or indentation at about the middle of said strut and/or crown width. In a preferred example, the luminal surface of said strut and/or crowns is flat/straight, substantially flat/straight, concave, or substantially concave, across the width of said strut and/or crown. In a preferred example, the side surfaces extending between the abluminal and luminal surfaces are convex or substantially convex. In another example the side surface extending between the luminal and abluminal surfaces are flat or substantially flat. In some examples, the side surface regions slant slightly outward between the side surface region and luminal surface region so the width at a region adjacent to the luminal surface is greater than the width of the struts and/or crowns at a region adjacent to the abluminal surface region.

In another example, the cross section of said struts and/or crowns abluminal surface has a depression or indentation at about the mid-section (or about the middle or about a mid-point) of said strut and/or crown abluminal surface. In a preferred example, the luminal surface of said strut and/or crowns is flat/straight, substantially flat/straight, concave, or substantially concave across the width of said strut and/or crown. The depression or indentation at about the mid-section of the said strut on the abluminal surface provides for increased interaction of the artery vessel wall with the strut as the stent is deloyed from a crimped configuration to the deployed configuration in a body lumen. The depression or indentation about the mid-section of the said strut on the abluminal surface provides for reduced scaffold slippage, and improved scaffold placement during implantation of the scaffold in a body lumen.

In a preferred example the luminal surface of said strut and/or crowns is flat/straight, substantially flat/straight, concave, or substantially concave across the width of said strut and/or crown. Such luminal surface shapes provide a smaller strut thickness, lower crimp profile, better fit onto the delivery system, reduced blood flow disturbance in the artery, or better or faster endothelialization of the implanted stent. The substantially flat or substantially concave luminal surface may be combined with any of the described abluminal and side surface regions, including for example, concave or convex abluminal surface regions and flat or convex side surface regions.

In one example, the thickness of the indentation or depression on the abluminal surface region ranges between 1 micrometer and 50 micrometer, preferably ranges between 1 micrometer and 25 micrometer, and most preferably ranges between 1 micrometer and 15 micrometer. In one example, the width of said depression or indentation at or near the widest point or section of the depression or indentation ranges between 1 micrometer and 50 micrometer, preferably ranges between 1 micrometer and 25 micrometer, and most preferably ranges between 1 micrometer and 15 micrometer. While the depression or indentation is depicted in the drawings as a concave depression in the otherwise convex abluminal surface region of the struts and/or crowns, the indentation or depression can have any shape such as concave, square, rectangle, U shape, etc. In some examples, the indentation or concave section of the convex abluminal surface does not extend across the width of the abluminal surface region and only extends about one fourth of the distance between the side surface regions.

In another example, the cross section of said struts and/or crowns has an abluminal surface that is substantially convex across the width of said struts and/or crowns. In another example said struts and/or crowns have a substantially convex shape abluminal surface and have side surfaces that are substantially straight or convex. In another example the cross section of said struts and/or crown abluminal surface is substantially convex across the width of said strut and/or crown and the abluminal surface has an indentation or depression at about the middle point of said strut and/or crown abluminal surface. In another example, the cross section of said struts and/or crown has an abluminal surface that is substantially convex across the width of said strut and/or crown and the abluminal surface has an indentation or depression about 1 micrometer to about 25 micrometer from the middle point of said strut and/or crown abluminal surface.

In another example the cross section of said struts and/or crowns has an abluminal surface that is substantially convex across the width of said strut and/or crown and has the maximum thickness about the middle of said width. In another example of any of the previous examples the cross section of said struts and/or crown having an abluminal surface that is substantially convex across said abluminal surface of said strut and/or crown and the abluminal surface has an indentation or depression at about the middle point of said abluminal surface with the maximum thickness of said strut and/or crown located adjacent to said indentation or depression.

It can be appreciated that all these examples within this application are applicable to all biodegradable materials including polymeric and metallic materials. It can also be appreciated that all the examples of forming with desired shape and treating to form a desired shape are applicable to all biodegradable materials including polymeric and metallic materials.

In some examples, the stent prosthesis is formed as a tubular body by extrusion, dipping, molding or printing and then patterned into a stent. In some examples the stent prosthesis is formed as a sheet, wherein the sheet is rolled to form a tubular body wherein the sheet is patterned into a stent before or after forming into a tubular body. The rolled sheet edges are affixed or joined together to form a tubular body by treatment such as using heating, chemical bonding, ultrasound bonding, laser bonding or other means. In some examples the stent prosthesis is formed as a sheet, wherein the sheet is patterned prior to rolling the patterned stent into a tubular patterned stent using the methods described previously. In some examples, the stent prosthesis is formed as a tubular pattered body, wherein the patterning and forming of the tubular body take place concurrently, such as the example of 3-D printing. In some examples, the stent prosthesis is formed as a three dimensional structure or body and then patterned into a stent. In some examples, the stent prosthesis is formed as a substantially tubular body and then patterned into a stent. In any of the above examples the structural elements are formed with the desired shape or treated to form the desired shape as described herein.

In a preferred example, the luminal surface of said strut and/or crowns of any of the examples is flat/straight, substantially flat/straight, concave, or substantially concave, across the width of said strut and/or crown.

In a preferred example, the biodegradable stent is heat treated one or more times after patterning and before crimping. Heat treating the biodegradable stent after patterning and before crimping provides for at least some of the following: increased radial strength in the deployed configuration. aligning the polymeric material orientation in the radial direction, increase orientation of the polymeric material in the radial direction, and reduced residual solvent in the stent. In one example, heat treating the biodegradable stent after patterning and after treatment to form the desired shape cross sectional shape for the struts and/or crowns and before crimping provides for substantially maintaining the stent pattern.

It can be appreciated that a prosthesis may have any or all of the features set out in this document.

BRIEF DESCRIPTION OF THE DRAWINGS

FIG. 3 is a cross section of a stent structural element having a concave abluminal surface region, a concave luminal surface region, and two convex side surface regions, showing a bulbous region extending between the luminal surface region and abluminal surface region;

FIG. 4 is a cross section of a stent structural element having convex side surface regions, a concave abluminal surface region and a substantially straight/flat luminal surface region, showing a bulbous region extending between the abluminal surface region and the luminal surface region;

FIG. 5 is a cross section of a stent structural element having two convex side surface regions, a substantially straight/flat abluminal surface region and a concave luminal surface region, showing a bulbous region extending between the abluminal surface region and the luminal surface region;

FIG. 6 is a cross section of a stent structural element having substantially straight side surface regions, a concave abluminal surface region and a concave luminal surface region, showing a bulbous region in the abluminal surface region extending or protruding outwardly and a bulbous region in the luminal surface region extending or protruding outwardly;

FIG. 7 is a cross section of a stent structural element having convex side surface regions, a concave abluminal surface region and a concave luminal surface region with a center part of the concave surface regions being substantially straight (flat), showing a bulbous region extending between the abluminal and luminal surface regions extending outwardly;

FIG. 8 is a cross section of a stent structural element having concave side surface regions, a concave abluminal surface region and a concave luminal surface region, showing bulbous regions in the abluminal surface region extending or protruding outwardly and bulbous regions in the luminal surface region extending or protruding outwardly;

FIG. 9 is a cross section of a stent structural element having a dogbone shape comprising concave luminal and abluminal surface regions, and convex side surface regions, showing a bulbous region extending between the abluminal surface region and the luminal surface region where the bulbous region comprises an abluminal surface region that has a convex shape towards the end of the structural element width and a luminal surface region that has a convex shape towards the end of the structural element width;

FIG. 10 is a cross section of a stent structural element having a racetrack shape with substantially flat luminal and abluminal surface regions, and convex side surface regions;

FIG. 11 is a cross section of a stent structural element having an elliptical shape with convex luminal and abluminal surface regions, and convex side surface regions;

DETAILED DESCRIPTION OF THE INVENTION

Figure 1:
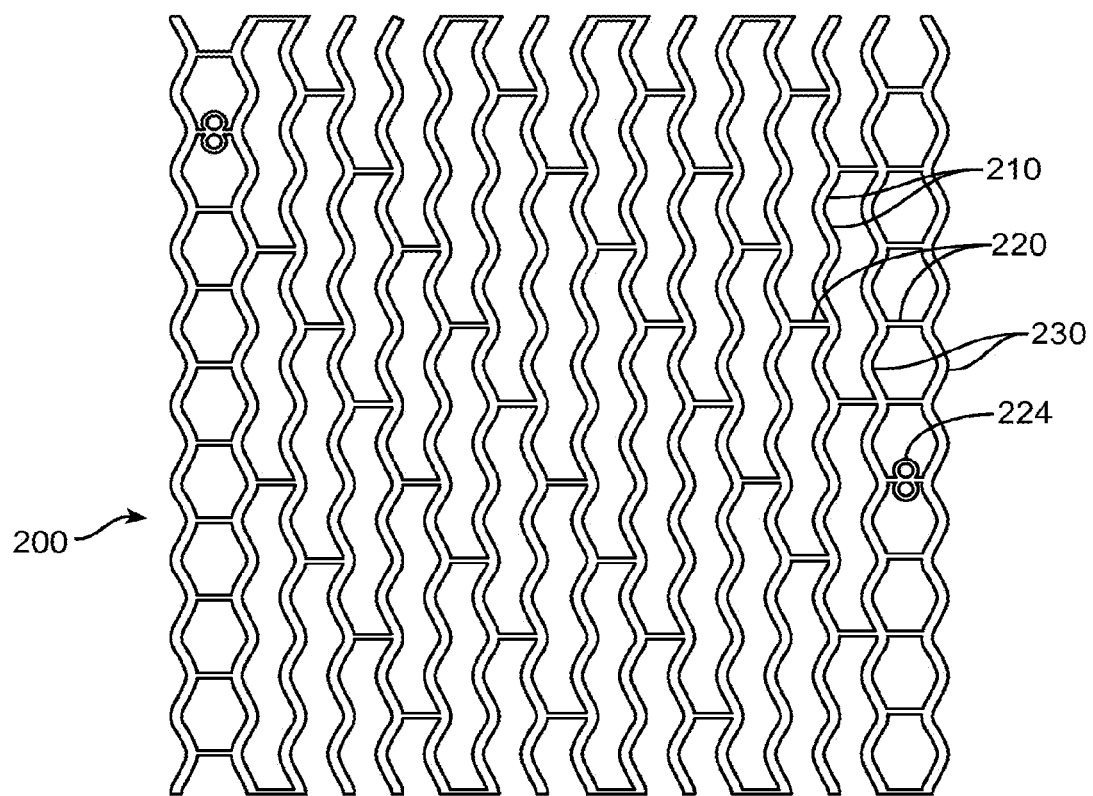
FIG. 1 depicts an example of a two dimensional stent pattern.

Embodiments provide an expandable biodegradable stent prosthesis comprising: a tubular expandable stent prosthesis body comprising a biodegradable material, for example a polymeric biodegradable material, said expandable stent prosthesis body comprising stent structural elements each having a luminal surface and an abluminal surface and a thickness between said luminal and abluminal surfaces; wherein a region extending between the abluminal surface and the luminal surface of at least some structural elements is bulbous.

Embodiments provide an expandable biodegradable stent prosthesis comprising: a tubular expandable stent prosthesis body comprising a biodegradable material, for example a polymeric biodegradable material, said expandable stent prosthesis body comprising stent structural elements each having a surface with a luminal surface region, an abluminal surface region, coupling portions coupling the abluminal and luminal surface regions, and a thickness between said luminal and abluminal surface regions; wherein at least a part of at least some of the coupling portions is bulbous.

Embodiments provide an expandable biodegradable stent prosthesis comprising: a tubular expandable stent prosthesis body comprising a biodegradable material, for example a polymeric biodegradable material, said expandable stent prosthesis body comprising stent structural elements each having an interior, luminal, surface region and an exterior, abluminal, surface region such that when the stent prosthesis is placed in the lumen of a vessel, the luminal surface regions face the lumen of the vessel and the abluminal surface regions face the vessel wall; wherein at least some of the abluminal surface regions have a concave shape across substantially the width of said surface regions; and/or at least some of the luminal surface regions have a concave shape across substantially the width of said surface regions; and/or at least some of the side surface regions coupling the abluminal and luminal surface regions have a straight, convex or concave shape across substantially the width of said surface regions.

In a preferred example, the luminal surface of said strut and/or crowns is flat/straight, substantially flat/straight, concave, or substantially concave, across the width of said strut and/or crown. In one preferred example, the side surfaces extending between the abluminal and luminal surfaces are convex or substantially convex. In another example, the side surface extending between the luminal and abluminal surfaces are flat or substantially flat. In one preferred example, the luminal surface of said strut and/or crowns is substantially flat or concave across the width of said strut and/or crown, the side surfaces are flat or convex and the abluminal surface is convex so the thickest part of the struts and/or crowns falls at about the middle of the width of the struts and/or crowns. In one preferred example, the luminal surface of said strut and/or crowns is substantially flat across the width of said strut and/or crown, the side surfaces are convex and the abluminal surface is convex so the thickest part of the struts and/or crowns falls at about the middle of the width of the struts and/or crowns. In another preferred example, the luminal surface of said struts and/or crowns is substantially flat or substantially concave across the width of said strut and/or crown, the side surfaces are flat or convex and the abluminal surface is convex with an indentation at about the middle of the width of the abluminal surface region. In another preferred example, the luminal surface of said struts and/or crowns is substantially flat across the width of said strut and/or crown, the side surfaces are convex and the abluminal surface is convex with an indentation at about the middle of the width of the abluminal surface region.

Each stent structural element (for example struts or other stent structures such as crowns or links) has a particular (certain) surface region geometry or is modified according to a treatment process described herein to provide that certain geometry. As an example, an expandable stent prosthesis may be formed by laser patterning or cutting from a tube or sheet of polymeric material to provide stent structural elements (for example struts or other stent structures such as crowns), with many having substantially rectangular or square cross sections and the expandable stent prosthesis may be treated to provide the certain geometry such as convex side surface regions and/or concave or flat abluminal surface regions.

An exemplary stent pattern is shown in FIG. 1 represented in two dimensions. The stent body 200 comprises stent structural elements forming sinusoidal rings, in this example the stent structural elements comprise struts 210 and V or U shaped crowns 230 joining the struts. The rings are interconnected by links 220. In the example stent pattern shown, links 220 connect adjacent crowns. A length of the stent can be adjusted by changing a number of rings. Some of the links 220 or struts 210 may be replaced by or attached to one or more loops 224 each containing one, two or more radiopaque markers axially or radially or somewhere in between. For example two such pairs of radiopaque markers can be provided at the opposite ends of the stent, and/or at the opposite side of the stent. The stent 200 can be balloon expandable and has low recoil, has sufficient radial strength to support a body lumen, conformable to the body lumen, and has low percent shortening upon expansion of less than 15%. Many other stent structures include differing arrangements of struts, crowns, links and other structures which together form a balloon expandable stent, or stent body, and can be modified according to the methods described herein. The stent can also be self-expandable, or self-expandable prior to balloon expansion, or can self-expand to a second larger diameter than a first deployed diameter after recoil from said first deployed diameter. The stent structures (e.g. struts) have luminal and abluminal surface regions and two side surface regions extending between the luminal and abluminal surface regions as can be seen in the cross sectional views of FIGS. 2-11. Stent structural elements, may have a thickness of 100 micrometer, but the thickness can range from 25 micrometer to 500 micrometer, or from 75 micrometer to 300 micrometer, or preferably from 100-200 micrometers. The strut length (the longest dimension) may be 0.75 mm, but strut length can range from 0.35 mm to 3 mm, preferably from 0.5 mm to 1.5 mm, or other. The width of stent structural elements may be 150 micrometer, but can range from 50 to 500 micrometer, from 100 to 300 micrometers or from 150 to 250 micrometers.

Other embodiments of stent and materials and treatments therefore are described in further detail in U.S. Pat. Nos. 8,182,890; 8,323,760; 8,636,792; 8,814,930; and U.S. Patent Publication Nos. 2008/0177373 and 2006/0029711 which have been previously incorporated by reference herein.

Figure 19:
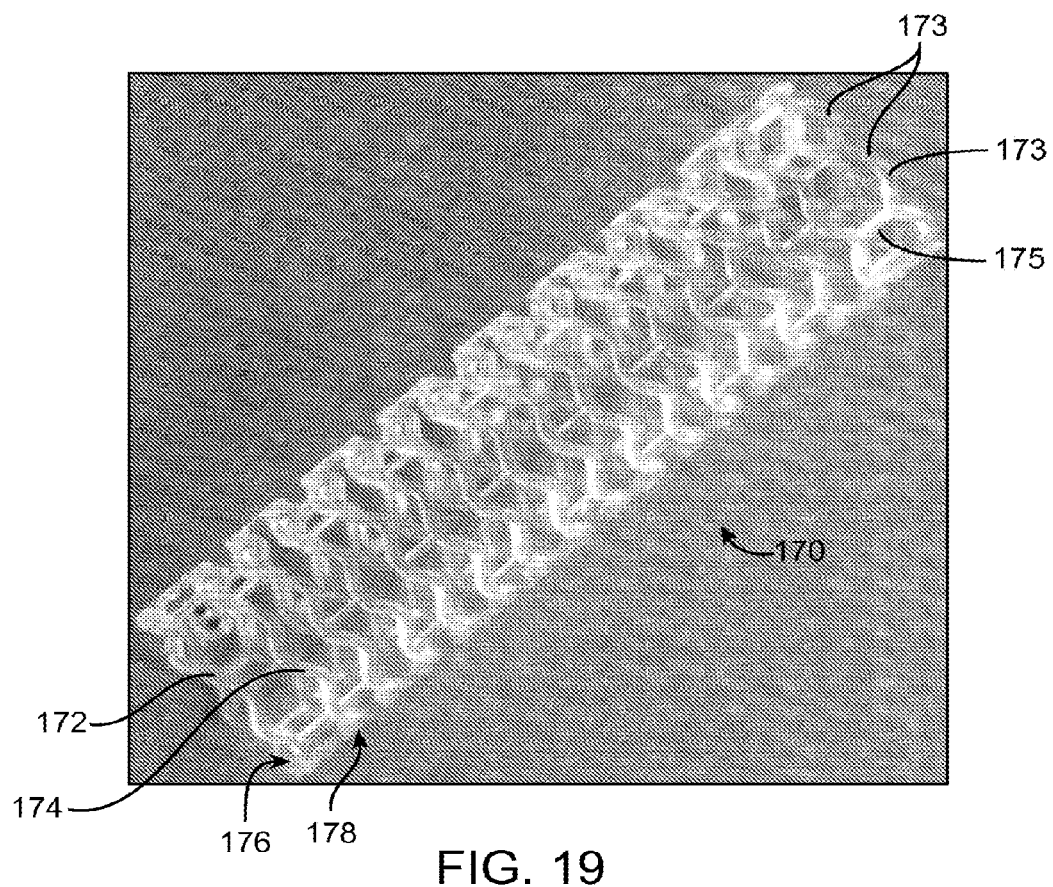
FIG. 19 is a perspective view showing an example of a stent prosthesis showing the stent pattern.

An exemplary patterned stent 170 is shown in FIG. 19. The patterned stent, stent or stent body 170 has struts 174 joined by crowns 172. The patterned stent has luminal surface regions 176 facing the lumen of the blood vessel, and abluminal surface regions 178 which face the blood vessel wall or faces the lumen wall. Each of the stent structures such as struts, crowns, and links, has two side surface regions extending between the luminal and abluminal surface regions. The rings 173 each comprise struts 174 joined by crowns 172. The rings 173 can be in-phase or out-of-phase or a combination thereof and are interconnected by links 175. A ring 173 is connected to an adjacent ring by links 175, or also some adjacent crowns are connected by links 175. Some of the links 175 may be attached to or replaced by one or more loops each containing one, two or more axially or radially displaced radiopaque markers, or radiopaque markers may be placed in the end rings of the patterned stent. The patterned stent 170 is balloon expandable and has low recoil, sufficient radial strength to support a body lumen or blood vessel, conformability to the body lumen or blood vessel, and low percent shortening upon expansion of less than 15%.

Many other stent patterns including differing arrangements of struts, crowns, links and other structures which together form a balloon expandable structure are possible. Two such examples are shown in FIGS. 20 and 21.

Figure 20:
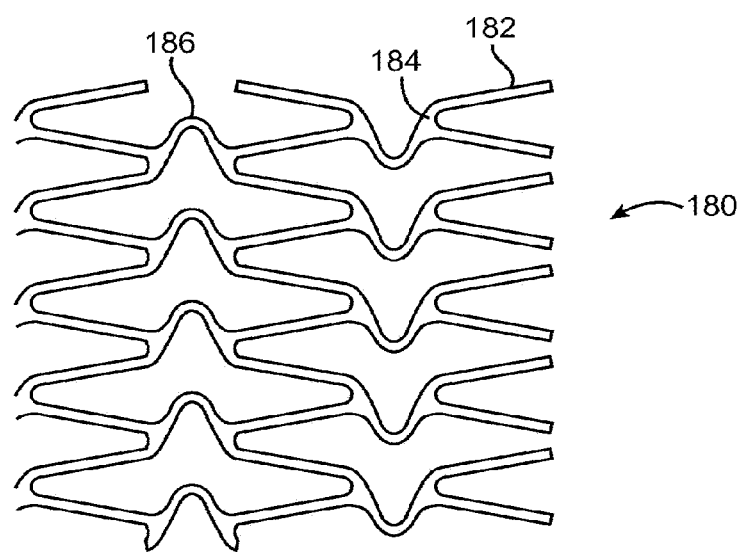
FIG. 20 is a two dimensional top view showing an example of a part of a stent prosthesis, showing the stent pattern.

FIG. 20 depicts a two dimensional view of a part/portion of a patterned stent 180 having a plurality of struts 182 joined by crowns 184. As shown in FIG. 20, the crowns 184 are connected by U-shaped links 186 which alternate in directions (upward and downward directed) depending on axial location along the length of the stent. The U-shaped links 186 may be replaced with straight, S-shaped, W-shaped or other shaped links and may be positioned at every crown or at some crowns, every other crown, or other numbers of crowns. In addition to links connecting adjacent rings, typically connecting adjacent crowns of adjacent rings, links can also connect/interconnect struts to other struts or crowns of adjacent rings. In addition to or as an alternative to rings, or serpentine ring patterns, helically wound rings, or helically wound serpentine patterns can also be used.

Figure 21:
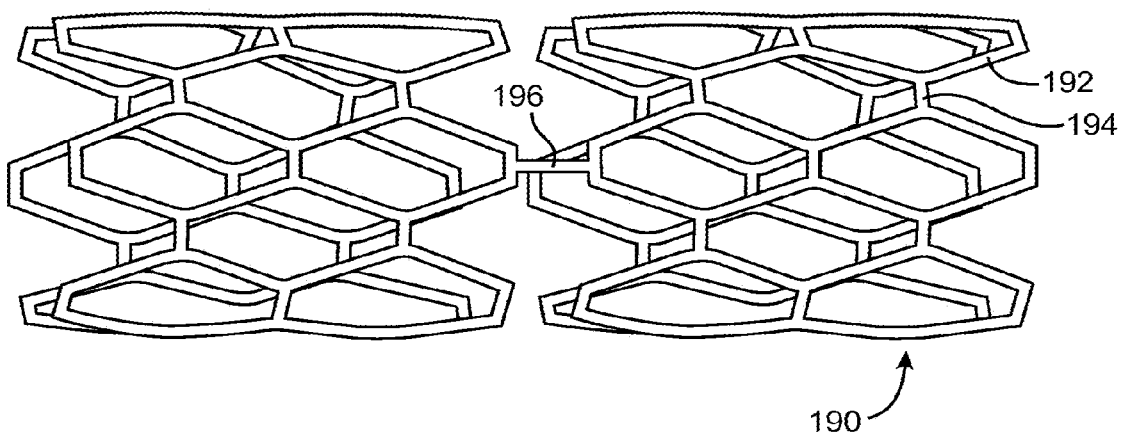
FIG. 21 is a side perspective view showing an example of a stent prosthesis showing the stent pattern.

FIG. 21 depicts an example of a patterned stent 190 having struts 192 and crowns 194 joining struts. Optionally as seen in the patterned stent of FIG. 21, link 196 connects two adjacent crowns. The links 196 may be straight, sinusoidal, or other shaped. One, two or more links 196 can connect the stent rings. The struts shown in the stent examples of FIGS. 1 and 19-21 are straight; however some or all of these straight struts can be replaced by curved or other shaped struts. Struts can be axially aligned in a crimped configuration or can be at an angle to the longitudinal axis. Upon expansion of the stent, generally the angle between the struts and the longitudinal axis of the stent increases.

In a stent pattern, generally crowns join struts, for example crowns may join two struts or three or four struts, or other. Crowns can be straight, arc, semi-circular, or key hole shaped, or other crown shapes that connect struts. Struts can be straight, wavy, or other strut shapes. Struts may extend axially, in a helical direction, or other direction such as between an axial direction and a radial direction. Crowns can be connected to adjacent crowns. Crowns may be connected to adjacent crowns by a link, such link can be straight links, or have other shapes such as U, V, W, S, or other shapes or geometries. Crowns connected to adjacent crowns by links typically connected on any points or areas along the length of the crown may be connected to adjacent crowns without a link, at the point of intersection of the adjacent crowns or at any other point along the length of the adjacent crowns where they meet. Crowns may be connected to adjacent crowns by fusing the two crowns into one, such as in the embodiment of FIG. 21.

The terms "scaffold structures," "stent structures," and "stent elements" as used herein comprise stent structural elements such as struts, links, crowns, elements or other structural components of the stent prosthesis. Together these stent structural elements form a stent, scaffold, stent body, prosthesis, or prosthesis body. The terms "scaffold, "stent", and "prosthesis" can be used interchangeably.

The term "bulbous" or as used herein means resembling a bulb in shape, curving outwardly in a convex shape, protruding, protruding outwardly, extending, extending outwardly, bulging, bulb like, bulb shape, swelling, outwardly protruding or extending in a convex shape. A "dogbone" shape has opposed bulbous ends which need not necessarily be of the same size, shape or be uniform or symmetrical.

The term "concave" as used herein means hollowed or rounded inward like the inside of a bowl, sphere, circle, or other geometric shape such as an ellipse or parabola, arched in or curving in, and also may include a stepped series of surface regions which together form a concave shape.

The term "convex" as used herein means curved outward the exterior of a bowl sphere, circle or other geometric shape such as an ellipse or parabola, arched out or curving out, and also may include a stepped series of surface regions which together form a convex shape.

The surface region that has a concave or convex shape may be a smoothly continuous surface region, a surface region that has a concave or convex shape may have one or more discontinuities, depressions, protrusions or other perturbations, provided that the overall shape or form of the surface region is concave or convex shape. The bulbous surface regions may in some instances have one or more discontinuities, depressions, protrusions or other perturbations, provided that the overall shape or form is bulbous.

In disclosed embodiments, surface regions of stent structural elements created during laser cutting are modified to provide a shape which improves mechanical performance of the stent and/or provides improved drug delivery from the stent or from a coating on the shaped stent. The modified surface regions formed by the methods described herein may occur on some or substantially all stent structural elements.

The flat side surface regions extending between the luminal and abluminal surface regions of the stent structural elements (e.g. struts, crowns, links and/or other structures) of the stent created by a fabrication process such as laser cutting can be modified to form convex side surface regions, preferably convex side surface regions substantially along the thickness of the stent structural element. The convex side surface regions in either the convex or bulbous shape function to more widely distribute tensile stresses and compressive stresses along the stent and can increase radial strength of the stent. The dimension of a stent structural element between the luminal and abluminal surface regions is the thickness of the stent structural element. In some instances, the convex or bulbous shape of the side surface regions joining the abluminal and luminal surface regions may have a flat portion in about the middle of the side surface between the abluminal and luminal surface regions.

The flat or slightly convex abluminal surface regions of the stent structural elements can be modified by the processes/treatment described herein to form concave or flat abluminal surface regions. The flat or slightly concave luminal surface regions of the stent structural elements can be modified by the processes/treatment described herein to form concave luminal surface regions. In some instances, the concave shape of the abluminal surface region may have a flat portion at about the middle of the abluminal surface region or at about the middle of the width between the two side surface regions. Concave abluminal surface regions can provide benefits in drug coating and in drug delivery and benefits of embedding the stent into the vessel wall and convex side surface regions can provide benefits in retaining the stent on a balloon catheter, and also improved trackability in tortuous anatomy. Convex side surface regions make it easier to insert the stent on the catheter into and through the blood vessel to the desired location. The dimension of a stent structural element between its side surface regions is the width of the stent structure. The concave curvature of the abluminal and/or luminal surface regions extends substantially across the width of these surface regions.

The stent prosthesis may be further coated with a coating comprising at least one drug and at least one polymer, wherein the coating follows the contour of the underlying surface region, in a preferred embodiment, without substantially changing the luminal, abluminal or side surface region shapes.

The luminal and abluminal surface regions of the stent structural elements can be fabricated or modified by the processes described herein to form substantially dumbbell, barbell, bow tie, or dogbone shaped stent structural elements or cross section stent structural elements.

Figure 2A:
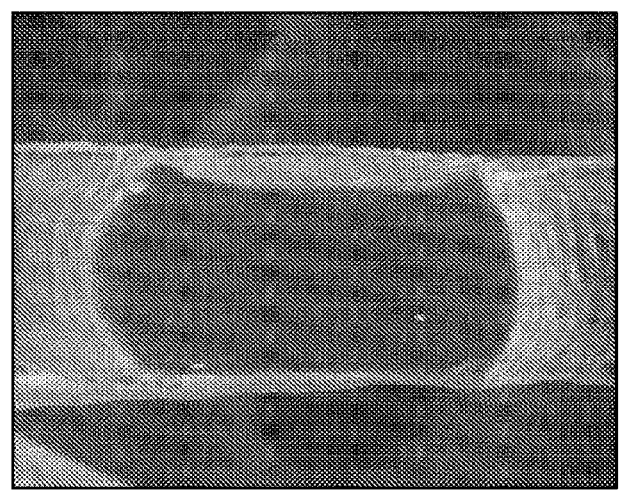
FIGS. 2A-2C are SEM images taken at a magnification of 1000-1200× showing a cross section of a stent structural element, in these images, showing a bulbous region extending between the abluminal surface region and the luminal surface region.
Figure 2B:
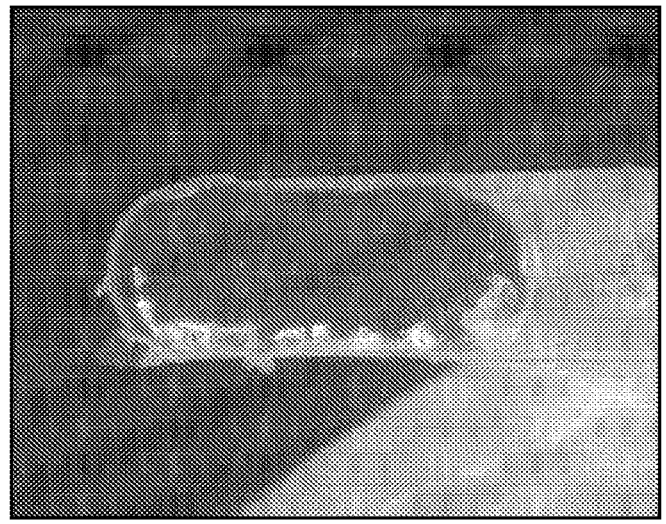
Figure 2C:
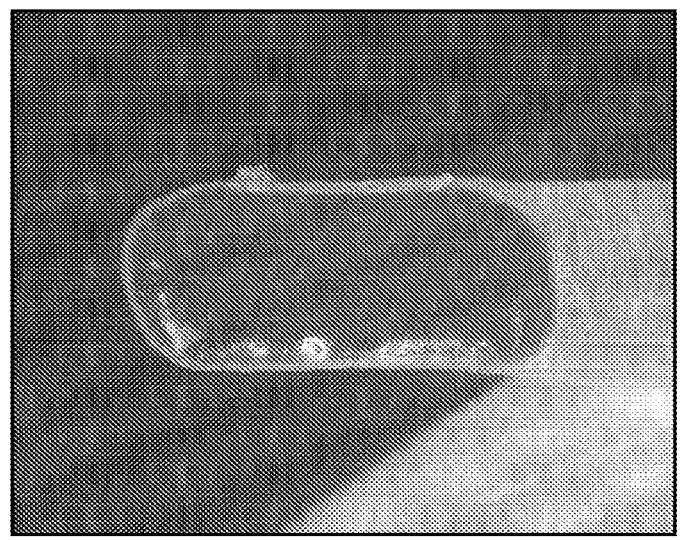

FIGS. 2A-2C are SEM images showing cross sections of stent structural elements which have been modified to have a shape designed for improved stent performance. The stent structural elements of each of FIGS. 2A-2C have a luminal surface region (bottom), an abluminal surface region (top), and two side surface regions. As shown in FIGS. 2A-C, the abluminal surface region is substantially concave across the width of the abluminal surface region while the two side surface regions are substantially convex across the thickness of the side surface regions of the strut. These structural elements cross sections of convex and/or concave surface regions form the dogbone, dumbbell, barbell or bulbous shape. This fabricated shape or modified/treated shape can distribute tensile stresses and compressive stresses along of the stent and can provide improved radial strength of the stent. The SEM images of FIGS. 2A-C are taken at a magnification of 1200× to show the stent structural element features at the micrometer level.

Figure 22:
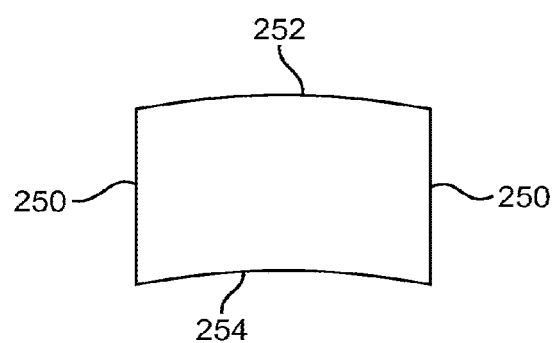
FIG. 22 is an example of a stent structural element, for example a strut, cross section before treatment.

FIG. 22 shows an example of a cross section of a stent structural element before modification or treatment when the strut is a part of a stent formed from a tube. The abluminal surface region 252 of the untreated stent structural element is slightly convex due to the overall curvature of the tube. Similarly, the luminal surface region 254 is slightly concave due to the curvature of the tube. The side surface regions 250 extend from the abluminal to the luminal surface regions and may be parallel or non-parallel depending on the process used to form the tubular stent but are generally flat/straight.

In embodiments, the modification of the stent surface region shapes improves tracking (maneuverability) and/or push by reducing the force required to track or push the stent mounted on a catheter through a cylindrical body, such as a blood vessel. The reduction of track or push force is achieved because of the changing of the area of surface region contact between the modified stent shape and the vessel. On the abluminal side, the unmodified surface regions on the stent structure can act like ratchet elements as the stent is pushed through a blood vessel, especially one with calcified lesions. This may hinder tracking or movement through the vessel because the unmodified side regions can get caught on the walls of the vessel. On the luminal side, the unmodified side regions of the stent can inhibit a guidewire or catheter from going through one of the spaces between stent structures, such as for treatment of a bifurcation. In order to improve tracking or passage of guidewire and catheter, it is beneficial to modify the shapes of the surface regions on the stent structure. The modification of the shape of the surface regions to provide convex surface regions, concave surface regions or a combination thereof improves performance of the stent.

Examples of processes which can be used to shape the surface regions of the stent structures include solvent treatment, media blasting, abrasive tumbling, mechanical shaping, laser shaping, heat treatment or other shaping processes. The processes of shaping the surface regions of the stent create substantially convex side surface regions extending from the luminal to the abluminal edge. The convex side surface regions can have radii of curvatures of about 0.020 to about 0.375 mm, about 0.030 to about 0.200 mm, or about 0.050 to about 0.175 mm. The processes of shaping the surface regions of the stent can also create substantially concave abluminal surface regions extending between the side surface regions. The concave luminal and/or abluminal surface regions can have radii of curvatures of about 0.020 to about 0.500 mm, about 0.030 to about 0.200 mm, or about 0.050 to about 0.175 mm. The concavity of the abluminal surface regions may extend substantially across the width from one side surface region of the stent structure to the other side surface region of the same structure, with a single concave depression, or a concave shape. Similarly, the convexity of side surface regions of the stent structures may extend across the thickness substantially from the luminal to the abluminal surface region of the same structure as one convex surface region, or as a convex shape.

The stent structures can be shaped before and/or after the application of a polymer/drug coating layer to the exterior of the stent. The shape treatment may be performed on the stent structure followed by coating with drug matrix coating wherein the coating process does not substantially change the shape of the surface regions but conforms to the concave and convex shapes of the treated surface regions.

The concave luminal surface regions after the treatment process may have a concave shape with a radius of curvature different than the radius of curvature of the inner diameter of the tube from which the stent is formed.

The ratio of radius of curvature of at least a portion of the luminal or abluminal surface region of the stent structure to the radius of curvature of the side of the stent structure may be less than one.

The ratio of radius of curvature of at least a portion of the luminal or abluminal surface region of the stent structure to the radius of curvature of the side of the stent structure may as another possibility be greater than one.

As another possibility, the radius of curvature of at least a portion of the luminal or abluminal surface region of the stent structure may be substantially equal to the radius of curvature of the side of the stent structure.

The radius of curvature of at least a portion of the concave luminal or abluminal surface regions may be greater than the radius of curvature of at least a portion of the convex side surface regions.

The cross section of a stent structure (stent structural element), may form a substantially dumbbell, barbell, bow tie, scalloped or dogbone shaped cross section structure.

Examples of shaped cross sections of stent structures are shown in FIGS. 3-11 each having a surface with a luminal surface region, an abluminal surface region, coupling portions coupling the abluminal and luminal surface regions, and a thickness between said luminal and abluminal surface regions; wherein at least a part of at least some of the coupling portions is bulbous. These stent structures can represent any stent structure including struts, crowns or/and links. The stent structure cross section shown in FIG. 3 includes a concave abluminal surface region 32 and a concave luminal surface region 34 and two convex side surface regions 30 extending between the luminal and abluminal surface regions of the stent structure. The convex shape of the side surface regions 30 extends substantially across the thickness of the stent structure to provide two bulbous regions. The concave shape of the abluminal and luminal surface regions 34, 32 extends substantially across the width of the stent structure. FIGS. 29-34 show struts with convex abluminal surface regions, flat or convex side surface regions and concave or substantially flat luminal surface regions.

The stent structure cross section shown in FIG. 4 includes two convex side surface regions 40, as well as a concave abluminal surface region 42 and a substantially flat luminal surface region 44 so that bulbous coupling portions are provided by the abluminal surface region 42 and the side surface regions 40. The stent structure cross section of FIG. 5 includes two convex side surface regions 50, as well as a substantially flat abluminal surface region 52 and a concave luminal surface region 54 so that bulbous coupling portions are provided by the luminal surface region 54 and the side surface regions 50. The stent structure cross section of FIG. 6 includes substantially flat side surface regions 60, as well as a concave abluminal surface region 62 and a concave luminal surface region 64 so that bulbous coupling portions are provided by the abluminal surface region 62 and the side surface regions 60 and by the luminal surface region 64 and the side surface regions 60. The stent structure cross section of FIG. 7 includes convex side surface regions 70, as well as a concave abluminal surface region 72 and a concave luminal surface region 74 so that bulbous coupling portions are provided by the abluminal surface region 76 and the side surface regions 70 and by the luminal surface region 74 and the side surface regions 70. The concave abluminal and luminal surface regions 72, 74 may include a substantially flat center portion 76 which forms a bottom part of the concave surface region. Similarly, the convex side surface regions 70 can include flat portions. The stent structure cross section of FIG. 8 includes two concave side surface regions 80, as well as a concave abluminal surface region 82 and a concave luminal surface region 84 so that bulbous coupling portions are provided by the abluminal surface region 82 and the side surface regions 80 and by the luminal surface region 84 and the side surface regions 80.

The stent structure cross section of FIG. 9 includes substantially convex side surface regions 90, as well as a concave abluminal surface region 92 and a concave luminal surface region 94 and rounded intersection of the concave and convex surface regions, which together form a dogbone shaped cross section so that bulbous coupling portions are provided by the side surface regions 90. In the example of FIG. 9, the shape of the stent structure is such that it can embed or nest the stent into the vessel wall upon expansion providing better stent apposition to the surrounding tissue. In contrast, square or rectangular flat cross section abluminal stent structure surface regions may inhibit embedding because the substantially flat surface regions push on the uneven plaque covered vessel wall during expansion.

The stent structure cross section of FIG. 10 includes convex side surface regions 98, a substantially flat abluminal surface region 96 and a substantially flat luminal surface region 97.

Figure 29:
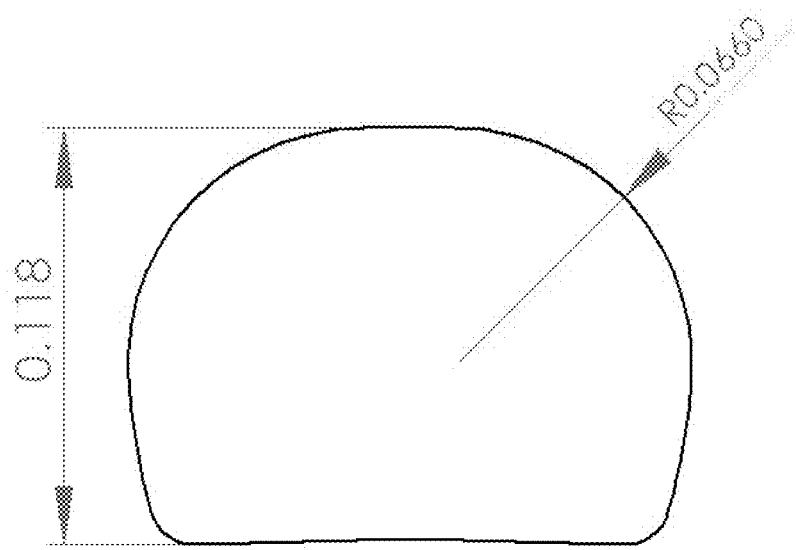
FIG. 29 is an example that shows a strut cross section with maximum thickness of 0.118 mm near the middle of the abluminal surface region of the strut cross section, with radiused edges adjacent to the abluminal surface of 0.066 mm, substantially convex sides, and a luminal surface that is concave.
Figure 30:
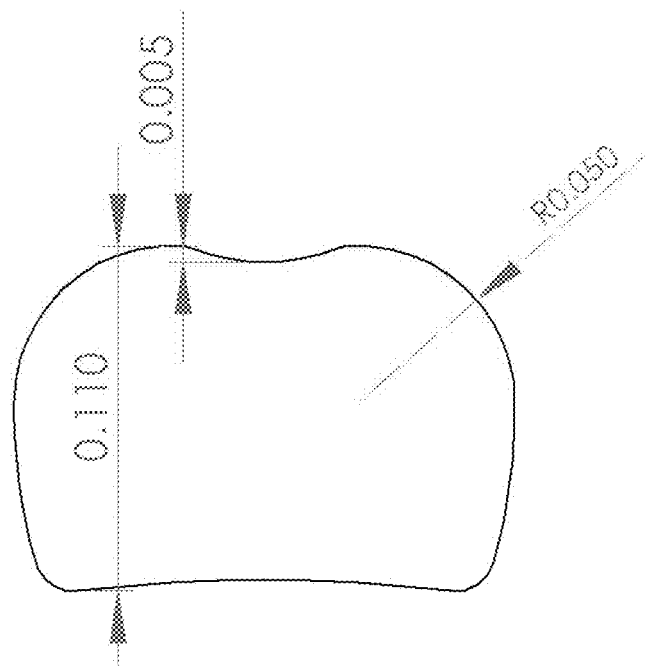
FIG. 30 is an example that shows a strut cross section with maximum thickness of 0.110 mm, a concave surface near the middle of the abluminal surface region of the strut cross section 0.005 mm deep, with radiused edges adjacent to the abluminal surface of 0.050 mm, substantially convex sides, and a luminal surface that is concave.
Figure 31:
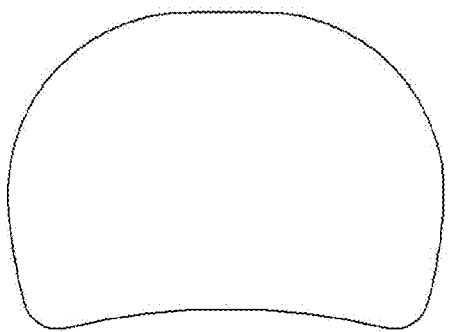
FIG. 31 is an example that shows a cross section of a strut having a maximum thickness about the middle of the abluminal surface of the strut and/or crown, with a concave luminal surface.
Figure 32:
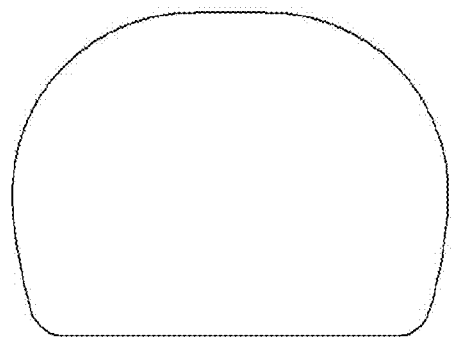
FIG. 32 is an example that shows a cross section of a strut having a maximum thickness at the middle of the abluminal surface region of the strut and/or crown with a substantially flat luminal surface.
Figure 33:
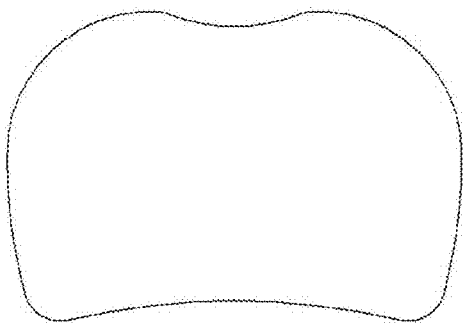
FIG. 33 is an example that shows a cross section of at least some of the stent structural elements such as struts and/or crowns having a maximum thickness about the middle of the abluminal surface region of the strut and/or crown, the maximum thickness located adjacent to a depression or indentation about the middle of the strut and/or crown abluminal surface, with a concave luminal surface.
Figure 34:
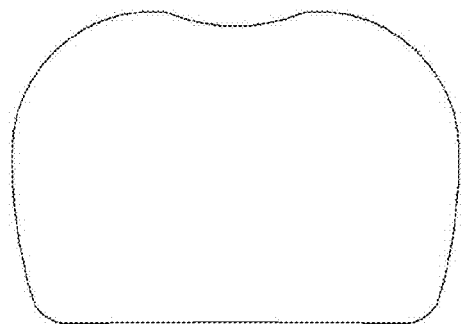
FIG. 34 is an example that shows a cross section of at least some of the stent structural elements such as struts and/or crowns having a maximum thickness about the middle of the strut and/or crown width, the maximum thickness located adjacent to a depression or indentation about the middle of the strut and/or crown abluminal surface, with a flat luminal surface.

The stent structure cross section of FIG. 11 includes convex side surface regions 100, a convex abluminal surface region 102 and a convex luminal surface region 104, which also is an elliptically shaped cross section. The stent structure cross section of FIG. 29 depicts a strut with a convex abluminal surface region, convex side surface regions and a concave luminal surface region. FIG. 30 shows a strut with a convex abluminal surface region that has a concave surface near the middle of the abluminal surface region of the strut cross-section, a concave luminal surface region and convex side surface regions. FIG. 31 shows a strut with a convex abluminal surface region, convex side surface regions and a concave luminal surface region. FIG. 32 shows a strut with a convex abluminal surface region, convex side surface regions and a substantially flat luminal surface region. FIG. 33 depicts a strut with a convex abluminal surface that has a concave surface or depression near the middle of the abluminal surface region, convex side surface regions and a concave luminal surface region. FIG. 34 shows a strut with a convex abluminal surface region that has a concave surface or depression region near the middle of the abluminal surface region, convex side surface regions and a substantially flat luminal surface region.

The convex and/or bulbous surface regions of the cross sections depicted in FIGS. 3-11 can distribute tensile stresses and compressive stresses along of the stent and can provide improved radial strength of the stent. Although the cross sections of FIGS. 3-11 and 29-34 have been shown as symmetrically shaped about a midline of the stent structure, the cross sections can also be asymmetrically shaped. The curvature of any of the surfaces may be asymmetrical along its curve and the curvature of the side surfaces may not be uniform one to the other. At least a portion of the stent structure with a concave abluminal surface region may have a minimum cross sectional thickness of between 50 to 300 micrometers, preferably between 75 to 200 micrometers, more preferably from 100 to 150 micrometers.

At least a portion of the stent structure with a concave abluminal surface region may have a maximum cross sectional thickness of between 50 to 500 micrometers, preferably between 75 to 300 micrometers, more preferably from 100 to 200 micrometers.

At least a portion of the stent structure with a convex side surface region may have a minimum cross sectional width of between 50 to 300 micrometers, preferably between 75 to 300 micrometers, more preferably from 100 to 150 micrometers.

Figure 24:
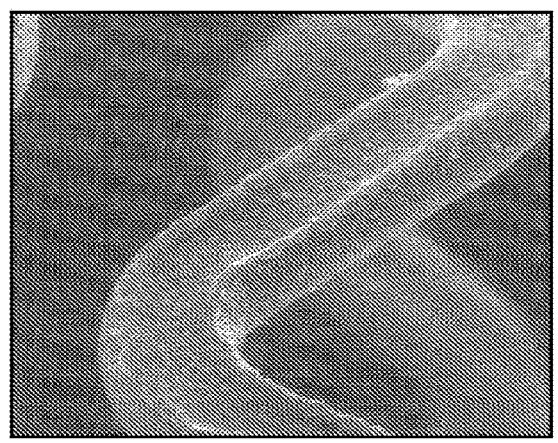
FIG. 24 is an SEM image at 500× magnification showing an abluminal perspective view of a stent structural element such as a strut, a crown or a link showing a lip extending along the strut and crown.
Figure 25:
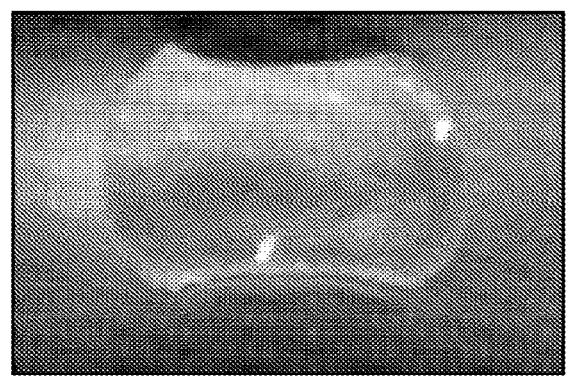
FIG. 25 is a cross section of a stent structural element such as a strut a crown, or a link which has been treated and viewed using Micro-Vu at approximately 315× magnification.

At least a portion of the stent structure with a convex side surface region may have a maximum cross sectional width of between 50 to 500 micrometers, preferably between 75 to 300 micrometers, more preferably from 100 to 200 micrometers. Measurements described herein of the dimensions including widths, thicknesses, radii of curvature and the like may be made on the actual prosthesis or on enlarged views of the prosthesis by SEM or microscope, such as the SEM 1200X images in FIGS. 2A-C and FIGS. 23 and 24. Other means of viewing the bulbous region, convex side surface region, or concave abluminal surface region can also be accomplished using microscope or Micro-Vu at magnifications ranging from 500×-1500×. FIG. 25 is a cross section of a treated stent structural element viewed using Micro-Vu at approximately 315× magnification with the abluminal surface on the top in the figure.

The maximum and minimum dimensions described herein may be measured on a single structural element, strut, crown or link. In some examples the maximum or minimum dimensions may be the mean of multiple points at different locations on one or more structural elements.

After the shaping process treatment, the variance in stent structure dimensions along the length of the stent may be less than 40%, preferably less than 25%, more preferably less than 10%. In some embodiments, the tubular body, stent or stent may be formed from at least one biodegradable polymer or other biodegradable material having desired degradation characteristics where the polymer may be modified to have the desired crystallinity, Tg, recoil, strength, shortening, expansion characteristics, crimping characteristics, molecular weight, and/or other characteristics. The tubular body or stent may be modified or treated by one or more treatments before, after or during patterning wherein the treatment comprises at least one or more of heating, cooling, pressurizing the polymeric material, chemically treating the polymeric material, or mechanically stamping the polymeric material.

Biodegradable polymers include one or more polymers, copolymers, blends, and combination thereof of: lactides, caprolactones, and glycolides. Some examples include poly-DL-Lactide, polylactide-co-glycolactide; polylactide-co-polycaprolactone, poly (L-lactide-co-trimethylene carbonate), polylactide-co-caprolactone, polytrimethylene carbonate, elastin, fibrin, collagen and copolymers; polyhydroxybutyrate; polyhydroxyvalerate, poly orthoesters, poly anhydrides, tyrosine derived polycarbonates, polyiminocarbonates, and the like. The biodegradable polylactide based polymer may comprise a copolymer of L-lactide and glycolide, preferably with a weight ratio of 85% L-lactide to 15% glycolide. As another example the biodegradable polylactide based polymer may comprise a copolymer of L-lactide and caprolactone, preferably with a weight ratio of 90% L-lactide to 10% caprolactone.

In some examples, the tubular body, stent or stent comprises a degradable polymeric material wherein the polymeric material comprises one or more polymers; or one or more co-polymers; or one or more blends of monomers, polymers or copolymers; and combinations thereof. The polymeric material may comprise one or more polymer or one or more co-polymer. Additionally, at least one monomer, polymer, or co-polymer of similar material (to the one or more polymer or the one or more co-polymer) is blended with the polymeric material.

In some examples, a biodegradable stent comprising a polymeric material comprises a copolymer of lactide and caprolactone in the ratio by weight ranging from 80-99% lactide to 1-20% caprolactone; wherein the polymeric material further comprises a monomer or polymer including a copolymer of one or more of the following: lactide, glycolide, lactide glycolide, caprolactone, and lactide caprolactone; wherein the one or more monomer or polymer total amount is 1 to 100 micrograms per milligram of polymeric material, preferably 5 to 75 micrograms per milligram of polymeric material, more preferably 10 to 50 micrograms per milligrams of polymeric material; wherein the stent with the modified structure cross section is capable of being crimped from an expanded configuration to a smaller crimped configuration, and at body temperature capable of being expanded to a deployed configuration, and having sufficient strength when expanded to support a body lumen, without fracture of the stent.

The one or more monomer and/or polymer may change (increase or decrease) the crystallinity of the polymeric material by 5% to 150%, preferably by 10% to 75%, more preferably by 10% to 50%. In some examples, the one or more monomer and/or polymer controls the crystallinity of the polymeric material to between 1% and 55%, preferably between 1% and 35%. In some examples, the one or more monomer and/or polymer does not change the crystallinity of the polymeric material from being between 1% and 55%. The one or more monomer and/or polymer may not substantially change the Tg of the polymeric material. Alternatively, the one or more monomer and/or polymer changes (increases or decreases) the Tg temperature of the polymeric material by 1° C. to 15° C., preferably 1° C. to 10° C., more preferably by 1° C. to 5° C. In an example, the one or more monomer and/or polymer controls the Tg temperature of the polymeric material to between 20° C. and 55° C., preferably to between 35° C. and 50° C., more preferably to between 37° C. and 50° C., most preferably between 37° C. and 45° C.

In some examples, the tubular body, degradable stent or stent may comprise at least one non-degradable polymer where the polymer may be modified to have the desired crystallinity, Tg, recoil, strength, shortening, expansion characteristics, crimping characteristics, molecular weight, and/or other characteristics. Non-degradable polymers include for example, a silicone-urethane copolymer, a polyurethane, poly(ethylene), phenoxy, ethylene vinyl acetate, chondroitin sulfatepoly(vinylidene fluoride), poly(vinylidene fluoride-co-hexafluoro propene), poly(tetrafluoroethylene), expanded poly(tetrafluoroethylene), poly(sulfone), polymethylmethacrylate, poly(n-butyl methacrylate), poly(N-vinyl pyrrolidone), copolymers of vinyl monomers and olefins such as poly(ethylene-co-vinyl alcohol) (EVAL), copolymers of acrylonitrile-styrene, ABS resins, and copolymers of ethylene-vinyl acetate, poly(amides) such as Nylon 66 and poly(caprolactam), alkyd resins, poly(oxymethylenes), poly(imides), poly(ester amides), epoxy resins, polyurethanes, rayon, and rayon-triacetate.

In some examples, the tubular body, biodegradable stent or stent may comprise at least one degradable or non-degradable biological molecule where the material may be modified to have the desired recoil, strength, shortening, expansion characteristics, crimping characteristics, molecular weight, and/or other characteristics. Biological materials include, for example, albumin, fibrin, fibrinogen, starch, poly(amino acids), peptides, proteins, gelatin, elastin, chondroitin sulfate, dermatan sulfate (a copolymer of D-glucuronic acid or L-iduronic acid and N-acetyl-D-galactosamine), collagen, hyaluronic acid, glycosaminoglycans, polysaccharides, chitin, chitosan, cellulose, cellulose acetate, cellulose butyrate, cellulose acetate butyrate, cellophane, cellulose nitrate, cellulose propionate, cellulose ethers, and carboxymethylcellulose; and any derivatives, analogs, homologues, congeners, salts, copolymers and combinations thereof.

In some examples, the tubular body, biodegradable stent or stent may comprise at least one degradable metal where the degradable metal has a desired recoil, strength, shortening, expansion characteristics, crimping characteristics, molecular weight, and/or other characteristics. Degradable materials for the metal stent include can be a suitable metal such as magnesium, zinc, iron, and alloys or combinations thereof. The metal can be modified to exhibit different hardnesses, and thus varying stiffnesses, by well-known annealing and manufacturing processes. The tubular body may also comprise combinations of biodegradable polymeric materials and degradable metals.

The degradable stent prosthesis may comprise a metal or metal alloy, optionally formed from a tubular body, wherein the metal or metal alloy comprises zinc, magnesium, and/or iron, or alloys, wherein the stent is treated to modify at least some abluminal surface regions making them concave substantially across the width of said abluminal surface regions, and/or modifying at least some of side surface regions making them substantially convex across the thickness of said side surface regions.

The above surface region modification may be performed without substantially changing weight or mass of the prosthesis compared to the weight or mass of the prosthesis before treatment, or without losing more than 15% in weight or mass after treatment, or without substantially losing more than 25% in weight or mass after treatment.

In some examples, the surface modification treatments is formed on a stent substantially free from pits, holes or grooves. In some examples, the structural elements prior to treatment and following treatment are substantially free from pits, holes or grooves. In some examples, a substantially rectangular cross section or a substantially square cross section of the structural elements prior to treatment becomes a non-rectangular cross section or non-square cross section after treatment. In some examples, a substantially square or substantially rectangular cross section of the structural elements prior to treatment becomes a dogbone, dumbbell, barbell, elliptical, oval or racetrack shaped cross section after treatment. The surface treatment to modify the shapes of the structural elements smoothes the surface regions and/or removes roughness, burrs, sharp edges or corners that would catch on the catheter or vessel wall upon delivery or deployment. Following this treatment, the stent prosthesis is substantially smooth and free from roughness, burrs, sharp edges or corners that would catch, pierce or injure the vessel wall upon delivery or deployment.

Degradable metal and metal alloys can be treated using the methods described in this application. In addition, treatments using acid such as nitric acid, hydrochloric acid, phosphoric acid and/or sulfuric acid can be used to modify the abluminal surface regions to concave, and side surface regions to convex.

1. Structure Shaping by Solvent Treatment

The stent structures may be shaped by exposure to at least one solvent. The exposure to the solvent can be accomplished in a variety of ways such as by dipping, spraying, exposure to solvent vapor or other solvent application processes.

a. Structure Shaping by Solvent Dipping

The stent supported lightly on a mandrel is dipped into a first solvent for about 1 second to one minute, 1 second to 30 seconds, or 2 seconds to 10 seconds and is quickly removed. The stent can be rinsed in a second solvent to remove materials that are adhering to the stent. The solvent, solvent concentration, and time of exposure may be selected based on its ability to move the stent material at the side surface regions of the stent to the luminal and abluminal surface regions and change the shapes of these surface regions without substantially dissolving the stent, that is without the polymeric material dissolving (or otherwise dispersing) in the solvent and without forming a solution of polymeric material in the treatment solvent. Also the solvents, concentrations and/or combinations of solvents and time of exposure may be selected based on the particular polymeric materials utilized to achieve the desired shaping of the stent structural elements. At least a portion of the surface regions on the side, abluminal and luminal surface regions of the struts and other structures can be shaped by inserting a loose mandrel such as a Teflon rod or tube inside the stent to support the stent during the selected treatment process. Preferably, the outer diameter of the loose mandrel is 0.001" to 0.100" smaller, more preferably 0.005" to 0.015" smaller than the inner diameter of the stent for a 2.5 to 4.0 mm stent.

At least some parts of the stent structure width may change by up to 25%, preferably change by up to 15%, more preferably change by up to 10%. In some examples, at least some parts of the stent structure thickness change by up to 25%, preferably change by up to 15%, more preferably change by up to 10% as a result of the treatment.

The stent cross section may be reduced in width and increased in thickness due to the transfer, flow, or movement of stent polymeric material during the solvent shaping process. In some examples, the processes of shaping the surface regions of the stent can increase the maximum thickness of the stent by at least at least 2%, at least 5%, 10%, at least 20%, or at least 30%, when taken in cross section. In some examples, the change in thickness after treatment is 2 to 35 micrometers, preferably 2-20 micrometer, and most preferably 4-10 micrometers. The maximum width of the struts and other structures can remain the same while the thickness changes as described above or can decrease by at least 2%, at least 5%, at least 10%, at least 20%, or at least 30%, when taken in cross section. The treatment may cause the flow of polymeric material from one side surface region to an immediately adjacent surface region, which may be on the same strut, crown or link.

In some examples, a change in width after treatment is 2 to 35 micrometers, preferably 2-20 micrometer, and most preferably 4-10 micrometers. In some examples, the treatment causes an initial diameter of the formed prosthesis to decrease to a smaller diameter, or a patterned diameter of the stent prosthesis to decrease to a smaller diameter. For example, the inner diameter of the prosthesis after treatment can be reduced by an amount of 0.05 to 3 mm, preferably 0.1 to 2 mm, most preferably 0.1 to 1 mm.

In some examples, the treatment does not substantially change angles between the struts or structural elements. In other examples, the angles between the struts or structural elements change by becoming smaller in an amount ranging from 1 to 75 degrees, preferably 2 and 50 degrees, most preferably 2 and 10 degrees. In other examples, the angles between the struts or structural elements change by becoming larger in an amount ranging from 1 to 75 degrees, preferably 2 and 50 degrees, most preferably 2 and 25 degrees.

In some examples, the treatment causes a change in length of the struts or structural elements which ranges between 0.1 and 5 mm, preferably 1 to 2 mm. In other examples, the treatment causes a shrinkage in length of the struts or structural elements in the range of 1% to 20%, preferably 1% to 15%.

In some embodiments, the shaping process can also be due to redistribution of the stent material from some surface regions of the stent to other surface regions to create the shaped struts with convex side surface regions and concave abluminal surface regions. The solvent is selected and applied for periods of time to soften the polymeric material without dissolving it so that it flows from one surface region to another portion of the surface region or an adjacent surface region.

In some embodiments, the stent mass after shaping process and removal of substantially all of the solvent is substantially unchanged from before the treatment process. In some embodiments, the stent mass after the shaping process is decreased by no more than 25%, preferable no more than 10%, more preferably no more than 5%. In some embodiments, after the treatment process with solvent and removal of substantially all of the solvent, the weight of the stent is substantially the same. In another example, the amount of solvent remaining in the polymeric material after treatment with solvent and removal of solvent ranges between 100 parts per million and 10,000 parts per million (PPM), preferably ranging between 1000 parts per million and 5000 parts per million. In some examples, the amount of solvent remaining in the polymeric material after removal of solvent ranges between 10-1000 micrograms, preferably ranges between 10 and 100 micrograms.

The first and second solvent can be a single solvent or a mixture of different solvents. Examples of the first solvent include methylene chloride (DCM), chloroform, tetrahydrofuran, dimethyl-sulfoxide (DMSO), acetone, toluene, xylene, DMF, or the like, or a combination thereof. The first solvent may be any solvent which can dissolve the stent if exposed to this solvent for more than 1 minute at room temperature. The second solvent can be any solvent or other fluid which does not measurably dissolve the stent if the stent is exposed to the second solvent for more than 1 minute at room temperature. In order to provide the shaping without dissolving the polymeric material or losing any significant amount of the polymeric material, the treatment times are about 0.1 second to one minute, 1 second to 30 seconds, or 2 seconds to 10 seconds followed by removal from the solvent.

In a preferred embodiment, the stent material is not dissolved (i.e. not permanently removed from the stent prosthesis) wherein the polymeric material flows from one surface region on a stent structural element to an adjacent surface region on the same stent structural element, or one surface region on a stent structural element to the same surface region on the same stent structural element.

The first solvent can also be a combination of a solvent that is capable of dissolving the stent and a solvent that does not dissolve the stent. For example, the first solvent can include a solvent capable of dissolving the stent after 1 minute or longer of exposure to the solvent at room temperature and a solvent which does not dissolve the stent after 1 minute of exposure at room temperature. One example of such a first solvent combination is 4 parts DCM and 6 parts Ethanol. In some examples, the first solvent includes from 0.1 to 10 parts of solvent capable of dissolving the stent (such as DCM) and 9.9 parts to 0.1 parts of solvent not capable of dissolving the stent (such as Ethanol). The second solvent can be ethanol, methanol, isopropanol, water, aqueous solution, or the like, or combinations therefore.

The stent shaping process may utilize a mixture of solvents to modify the stent structure cross section due to the transfer of stent material from its width to its thickness.

The stent shaping process may utilize at least one solvent to initiate the modification of the stent structure cross section due to the transfer of stent material from its width to the thickness and at least another solvent to terminate the process.

Instead of using a second solvent, the stent on a mandrel can be shaken or blown with gas to remove excess solvent and/or dried in vacuum, oven, and or pressurized $CO_2$. Instead of a second solvent, the stent can be quickly placed in an oven, vacuum oven, freeze dried or exposed to another known process to remove the first solvent.

Not all of the first or second solvent needs to be removed after the dipping treatment is complete. Additional processes which can be used to remove solvent include heat treatment, exposure to carbon dioxide, freeze drying or vacuum. The stent can be transferred to a bigger, tighter mandrel to maintain the dimensions of the stent for additional drying such as drying at ambient temperature, elevated temperature, such as below the glass transition temperature of the polymer in an oven, vacuum oven, freeze drying or the like, in a vacuum, or other means.

The stent can also be further treated by placing on a tight mandrel and dipping to further shape the abluminal and side surface regions as will be described further below. Additional shaping of the side, abluminal and luminal surface regions of the crowns and axial struts can be achieved by repeating a dipping treatment more than once or by dipping for longer periods of time. Agitating during the dipping treatment can increase the rate of shaping. Spinning or rotating of the stent in the solvent can help achieve a more consistent application of the solvent along the length of the stent and particularly in tight spaces of the stent. Spinning can also change the distribution of the material during shaping, for example to provide a strut shape with a wider abluminal side due to forces on the outer material of the stent during spinning. The stent can be treated while oriented in the solvent horizontally, vertically, at an angle or in a combination of orientations to achieve a desired shaping.

The stent may be rotated around its own axis and/or revolved around in a chamber with solvent to control the shaping of the stent structure cross section.

As an alternative or additionally to spinning or rotating the stent, the solvent media can flow relative to the stent, or a combination of rotating the stent and causing solvent to flow can be used to achieve the desired effect. The stent and the solvent can both move relative to each other. Examples of this would be a revolving stent on a rotating mandrel in a solvent bath which is being stirred with a stir bar.

Figure 12:
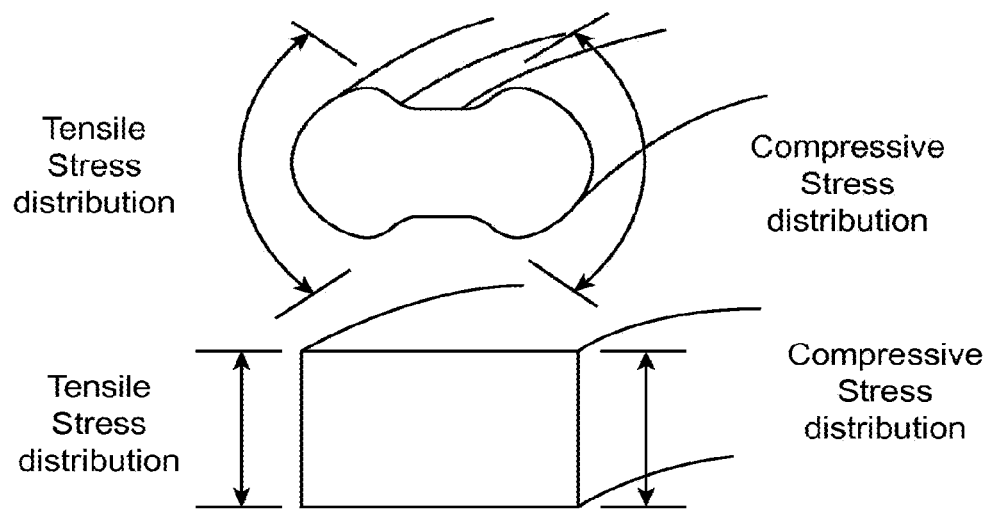
FIG. 12 is a schematic illustration of the difference in tensile and compressive stress distribution between a treated and untreated stents.

FIGS. 2A-2C illustrate cross sections of stent structural elements after treatment according to some examples. In these figures, the treatment provides a concave abluminal surface region across substantially the width of the abluminal surface region; it also provides convex side surface regions across the thickness of the side surface regions. These shapes allow the distribution of tensile and compressive stresses over a greater area as shown in FIG. 12. As shown in FIG. 12, the surface region area over which the tensile and compressive stresses are distributed during bending of the stent structural element is increased due to the convex side surface regions and this leads to increased radial strength of the stent. In some examples, a stent with modified cross section has increased radial strength by at least 5%, at least 10% or at least 20% over stents without modified cross section. The treatments described herein can increase the radial strength of the stent by at least 5%, at least 10% or at least 20%.

The first and second solvents and the processes for dipping and removing solvent can vary depending on the desired stent cross sectional shape.

One advantage of the abluminal shaping is the increased drug delivery to the walls of the lumen which can be achieved with a concave abluminal surface region. The abluminal concave surface region can help direct drug delivery to the lumen wall. The edges of the concave abluminal surface regions such as those shown in FIGS. 2A-2C can have a ledge or lip which further helps to direct drug delivery to the lumen wall. This focuses drug delivery using concave abluminal surface regions.

b. Luminal and Side Shaping by Solvent Dipping

Shaping of or enhancing the luminal shape and/or shaping the side surface regions of the stent struts, crowns and other structures without abluminal shaping can be achieved by placing a tube such as Teflon tube over the stent (or otherwise masking the surface areas not to be treated). The outer tube should be tight fitting so that no significant amount of fluid can pass between the outer surface regions of the stent and the inner surface region of the tube. Optionally, a looser mandrel such as a Teflon rod or tube can be inserted inside the stent as a support for handling purposes. Preferably, the outer diameter of this looser inner mandrel is 0.001" to 0.100" smaller, more preferably 0.005" to 0.015" smaller than the inner diameter of the stent. The stent sheathed with the outer tube and supported lightly on the inner mandrel is then dipped into a first solvent for about 1 sec and quickly removed and preferably rinsed in a second solvent to remove materials that are adhering to the stent according to any of the methods and with any of the solvents described above with respect to the previous processes.

Figure 13:
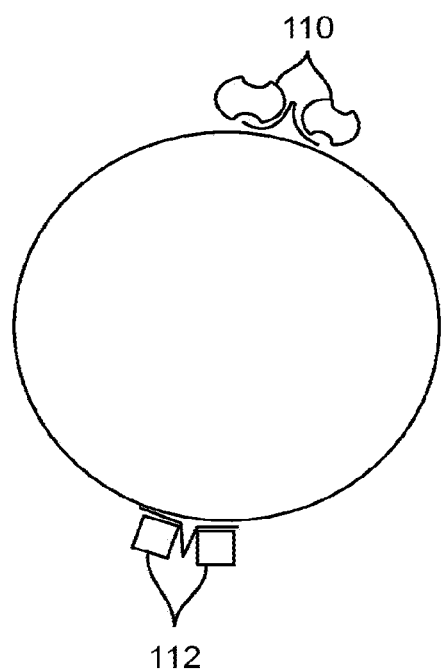
FIG. 13 is a schematic cross section of a balloon showing a pair of struts having modified/treated surface regions and a pair of struts having unmodified surface regions.

Shaped luminal surface regions and shaped side surface regions can provide an improved surface region for contact with a delivery system, such as a balloon catheter. The convex side surface regions provide greater contact than square or rectangular flat surface regions between balloon material of the delivery system and the stent. FIG. 13 illustrates a balloon with a pair of stent structural elements 110 having modified luminal surface regions and convex sides and a pair of stent structural elements 112 having flat surface regions. In the process of crimping the stent onto the balloon a portion or flap of balloon material extends between the stent structural elements. As can be seen in FIG. 13, there is increased surface region area of contact between the modified stent structural elements 110 with convex sides and the balloon flap than with the flat surface regions of the stent structural elements 112. This provides improved stent retention on a balloon catheter in a crimped configuration by using a shaping processing step.

Additionally, the concave luminal surface regions of the stent structures can also improve stent retention on a balloon or other delivery system by providing a form of suction or vacuum surface region which adhere the modified stent better to the balloon.

c. Solvent Vapor Shaping

The stent can be exposed to vapors of a solvent for an amount of time sufficient to provide a desired shaping of the stent structures. In the solvent vapor shaping method, the stent is placed adjacent to a bath of liquid solvent in a solvent chamber. The solvent is selected to be a solvent which can dissolve the stent at least in part if the stent is placed in the solvent for one minute. However, in this method, it is the vapors from the solvent which come in contact with the crowns, axial struts and other portions of the stent and redistribute the material of the stent to provide convex side surface regions, concave luminal and/or abluminal surface regions. The solvent or the entire vapor chamber can be heated to accelerate vaporization of the liquid solvent in the liquid bath. Alternatively, the solvent vapor can be provided into the chamber in a gaseous form alone or with other gases. The time of exposure of the stent to solvent vapor can be greater than 10 mins, greater than 30 mins, greater than 1 hour, greater than 24 hours, or greater than 48 hours.

In some examples, the stent may be rotated around its own axis and revolved around in a chamber with solvent vapor to control the shaping of the stent structure cross section.

After the solvent vapor shaping process is complete, excess solvent can be removed by a second solvent, heating, drying or any of the methods discussed herein. In some examples, the solvent chamber can be pressurized to increase the amount of solvent vapor in contact with the stent.

The exposure of only a portion of the stent to the solvent vapor, such as by inserting a tight tube inside the stent or inserting the stent inside a tight tube (or any other suitable form of masking) can preferentially shape the surface regions on the luminal or abluminal sides of the stent. Other masking methods can also be used.

The solvents employed in the solvent vapor smoothing process can include any of the solvents described above. Particularly useful solvents are those that can be provided in a gaseous form at a temperature of less than the Tg of the stent material.

d. Solvent Spraying

The stent can be exposed to solvent by spraying with the solvent to shape the surface regions of the stent structural elements and redistribute the stent material. Spraying of solvent can be performed with any spray apparatuses, such as those that are known for application of drug/polymer coatings to stents. The sprayed solvent may be any of the solvents described herein which are capable of dissolving a portion of the stent structure.

Solvent spraying from an exterior of the stent can result in preferential shaping with the abluminal surface regions experiencing greater concave shaping than the luminal surface regions. In some examples, abluminal surface regions have a concave radius of curvature greater than luminal surface regions. Solvent spraying can also be from an interior of the stent by passing a spray nozzle into the interior of the stent and moving it along the length of the stent interior. Masking of portions of the stent may also be used to get preferential shaping of some surface regions over other surface regions.

In some examples, a flow rate of solvent sprayed onto the stent is higher than typically use for coating a stent. Flow rates of at least 20 ul/min (microliter/minute), at least 30 ul/min, or preferably at least 75 ul/min, or more preferably at least 100 ul/min can be used.

A loose mandrel can be placed inside the stent during spraying to maintain the shape of the stent as the solvent is sprayed onto the surface regions.

The stent can be rotated and/or moved longitudinally during spraying. In some examples, the stent is rotated and moved in a crisscross fashion during spraying to achieve uniformity of shaping and to prevent large amounts of material from being dissolved or redistributed too quickly. Air can be blown at the stent to remove any excess solvent during and/or after spraying of the solvent. Removal of excess solvent can be performed by any of the processes described herein.

e. Other Solvent Application

In addition to application of solvent by dipping, spraying, or application of solvent vapor, solvent can be applied to a stent to provide shaped stent in other manners including ink jet printing, painting, gel application or the like.

Some of the solvent application methods described herein can apply solvent only to portions of the stent while leaving other portions of the stent untreated such as preferentially shaping and/or smoothing only the luminal or only the abluminal surface regions. In some examples, the treatment is applied only to the crowns to further enhance the convex side surface regions of the crowns as these are the areas most likely to affect tracking of the stent through the vasculature. The treatment can also be used to preferentially treat different longitudinal sections of the stent to achieve a stent with differing performance along its length. In some examples, the ends of the stent are treated to achieve a stent with greater radial strength at the stent ends.

Treatment including heating and/or solvent treatment to provide the desired shaped stent abluminal, luminal and side surface regions may be performed before or during patterning of a stent, such as during laser cutting, or after patterning of the stent. One or more treatments or additional treatments may be performed sequentially, or combined with other treatment processes, such as a heating and solvent treatment process combined, to enhance or control the treatment process. Treatments include heating such as heating in an oven, heating by application of a hot gas stream, freeze drying, cooling by refrigeration, fast cooling with liquid nitrogen, vacuum processing or drying by application of an inert gas may be used before, during, or after shaping treatment process. These treatment or additional treatments may be used to shape the material, remove solvents, soften or harden the polymeric material for treatment, and/or stabilize the treated stent.

2. Media Blasting

Shaping of the stent surface regions can also be performed by material removal or material compacting from the stent by various media blasting techniques. Material removal from or compacting of the stent crowns or axial struts of a stent to create convex side surface regions, and concave abluminal surface regions can be achieved using equipment such as a sandblaster, media blasting machine, or similar equipment which propels particles at the stent. The blasting treatment propels small, abrasive particles toward the stent in a particular pattern which matches the regions of the stent to be shaped.

Examples of particles which can be used include evaporable particles, such as dry ice, salt, sugar, sodium bicarbonate, combination thereof, or the like which will either vaporize or can dissolve in water. The use of dry ice or another evaporable particle as the media particles which will turn gaseous at ambient temperature eliminates the need for removal of the blasting particles after the surface region shaping process. In some examples, the evaporation of the evaporable particles may be assisted by application of heat, vacuum, or the like. The use of dry ice as the media particles can eliminate the need for removal after the shaping process because the dry ice will turn gaseous at ambient temperature.

Other blasting media can include polymeric particles such as polyethylene, polypropylene, polyethylene glycol, polyvinyl alcohol, polyvinylacetate, polyvinyl chloride, cellulose, copolymers of these, combination thereof, or the like which will dissolve in a solvent that does not immediately dissolve the stent such as ethanol, methanol, propanol, THF, acetone, or the like. Exposure to solvent after blasting with polymeric particles can remove particles that become at least partially embedded on the surface region of the stent. The media particles preferably can dissolve in a solvent in a period of less than 1 minute and the solvent is selected such that the stent does not dissolve in the solvent when the stent is exposed to solvent for 1 minute or longer.

A size of the blasting particles using screened mesh sizing can range from 60 to 600 mesh, from 100 to 550 mesh, or preferably from 150 to 500 mesh. The mesh sizes referenced herein are from standard mesh sizes, such as US Sieve Series and Tyler Mesh Size, used to classify particle size.

The size of the blasting particles impacting the surface region of the stent range from 250 micrometers to 10 micrometers, preferably from 100 micrometers to 20 micrometers, more preferably from 50 micrometers to 25 micrometers.

In some examples, instead of focusing the blasting particles on the edge during sandblasting, a mask can cover the majority of the stent surface region but exposes only a portion of the edges of the crowns or axial strut. The mask can be applied by ink jet printing technologies. The covered stent is then sandblasted to remove only material on the edge. Preferably sandblasting is done at an angle. The mask can then be removed by any known means, such as by application of a solvent which dissolves the mask without dissolving the stent. After removal of the mask the resulting convex side surface regions and concave luminal and abluminal surface regions are exposed.

The media blasting may compact the material to provide the desired shapes without removing a substantial amount of the polymeric material from which the stent is formed.

3. Abrasive Tumbling

The stent surface regions can be shaped by abrasive tumbling methods. The stent can be placed in a tumbler, shaker, or vibrator with a lapping media, a sandblasting media, abrasives, abrasive grit, liquid lubricants, dry ice, others, or combination thereof, to form concave abluminal surface region having radii of curvatures of about 0.030 to about 0.200 mm, about 0.040 to about 0.150 mm, or about 0.040 to about 0.100 mm. Examples of abrasive media include aluminum oxide, jeweler's rouge, optician's rouge, emery, silicon carbide, diamond, glass, metal, oxides, ceramics, or the like. In the abrasive tumbling methods, one or more stents are placed inside a barrel or tumbler which is placed on slowly rotating rails which rotates, shakes, or vibrates the barrel. The stents within the barrel slide past each other, with the lapping media, sandblasting media, abrasives, abrasive grit, liquid lubricants, others, or combination thereof, between them. The amount and speed of the shaping depends on the coarseness of the abrasive, and the duration of the tumble, shaking, or vibrating.

The stents can be cooled to make the material more brittle. The stent can be cooled to a temperature below 10 degrees Celsius, preferably below 0 degrees Celsius, more preferably below −50 degrees Celsius using dry ice or liquid nitrogen before and/or during tumbling.

The stents can be heated to make the material softer. The stent can be heated to a temperature above Tg before and/or during tumbling.

In some examples, a mask can be applied by ink jet printing technologies or another known process to allow selective abrasive shaping of the stent surface regions. The masked stent is then tumbled to remove only material on the selected portions. The mask can then be removed by any known means, such as by application of a solvent which dissolves the mask without dissolving the stent. After removal of the mask the resulting convex side surface regions and concave luminal and abluminal surface regions are exposed. As in the other shaping processed described herein, selective portions of the stent can be shaped without shaping other portions of the stent by use of mandrels, sleeves and/or masking.

4. Mechanical Shaping, Molding, Stamping and Ink Jet Printing

The surface regions of crowns, axial struts, or other stent structures of a stent can be shaped or chamfered by certain mechanical tools to form shaped surface regions. The surface regions can be shaped or chamfered with a miniature tool having a sharp edge or deburring brush and small enough to fit between crowns and axial struts and scraping the tool across the surface regions. These tools can be moved robotically and controlled by a camera and an image processing system.

In some examples, the tool can be a rotating miniature sanding tool which by spinning against the surface regions or edges of the crowns or axial struts creates convex side surface regions, concave luminal surface regions and/or concave abluminal surface regions.

In order to increase the hardness of polymer stents or other stents of soft materials for mechanical shaping according to any of the described processes, the stent can be held at a temperature below 10 degrees Celsius, preferably below 0 degrees Celsius, more preferably below −50 degrees Celsius using any suitable cooling method such as dry ice or liquid nitrogen.

The abluminal surface regions of the crowns of a stent can be shaped or chamfered by inserting a curved or flexible mandrel inside the stent. The stent in the curved position on the mandrel is then dragged over an abrasive material such as sandpaper wrapped around a cylinder, round file, deburring brush, sanding stone, or the like. As the stent in a curved position is abraded against the surface region of the abrasive means, the leading edge of the crowns will be chamfered, beveled or deburred.

An inside surface region of the stent can be processed to shape the luminal surface regions of the crowns, struts and other stent structures by inserting a flexible abrasive means through the interior of the stent.

Ink jet printing technologies can also be used to build up some portions of the stent or the stent to achieve concave luminal and abluminal surface regions and convex side surface regions of the stent structures. As an example, a dispenser nozzle (or ink jet print head or cartridge or reservoir therefor) may be filled with a polymeric material solution or an extrusion nozzle loaded with a solid rod of the polymeric material. The nozzle may then be positioned close to the surface region of an object such as a mandrel (optionally substantially round mandrel, preferably a 3-D patterned mandrel of the stent pattern desired) providing a former which together with control of the dispenser nozzle enables material to be deposited onto the mandrel to form a stent embodying the invention. For example, the mandrel may have approximately the deployed or optionally larger than the intended deployed diameter of the stent (labeled or nominal) or optionally 1.1-1.5 times larger than intended deployed diameter of the stent, and optionally the mandrel may have the inner (luminal) surface region shape of the stent and the dispenser nozzle may be controlled to dispense or extrude the polymer as the mandrel is rotated. In addition, the nozzle or the mandrel can be moved radially and or axially by a 3-axis motion controller. The polymer may be dispensed or extruded from the nozzle in a preprogrammed stent pattern and the dispensing of the polymer be controlled to vary the shape of surface regions to provide straight, concave and/or convex shaped surface regions as describes throughout this application. For example, one or more layers or traces of polymeric material can be laid down on top of each other to achieve a certain structural elements thickness. Also, the width of the layer or trace may be adjusted, to make it narrower. The nozzle may then dispenses or extrudes the polymeric material along one side of the initial trace and then repeat for the other side to achieve an abluminal concave surface region and the sides of the struts forming a convex surface region. The stent may be either left to dry, vacuumed, heat set, left to cool, or the like, or a combination thereof. Afterwards, the stent may be removed from the mandrel by swelling the stent with solvent such as ethanol, acetone, tetrahydrofuran, methylene chloride, or the like, or a combination thereof. After removal, the stent can be left to dry, vacuumed, heat set, left to cool, or the like, or a combination thereof. The stent may or may not be coated with a polymer-drug matrix, crimped on a delivery balloon catheter, packaged, and sterilized.

It should be appreciated that the stent structural elements or the stent itself may be manufactured so that the required surface regions have the required shape. As an example, the stent structural elements or the stent itself may be manufactured by way of '3D printing' whereby a three-dimensional model of the stent structural elements or the stent itself is supplied, in machine readable form, to a '3D printer' adapted to manufacture the stent structural elements or the stent itself. This may be by additive means such as extrusion, deposition, Electron Beam Freeform Fabrication (EBF), granular materials binding, lamination, photopolymerization, or stereolithography or a combination thereof or by a removal process such as ablation or cutting. The machine readable model may comprise a spatial map of the object to be printed, typically in the form of a Cartesian coordinate system defining the object's surface regions. This spatial map may comprise a computer file which may be provided in any one of a number of file conventions. One example of a file convention is a STL (STereoLithography) file which may be in the form of ASCII (American Standard Code for Information Interchange) or binary and specifies areas by way of triangulated surface regions with defined normals and vertices. Another file format is AMF (Additive Manufacturing File) which provides the facility to specify the material and texture of each surface region as well as allowing for curved triangulated surface regions. The mapping of the stent structural elements or the stent itself may then be converted into instructions to be executed by 3D printer according to the printing method being used. This may comprise splitting the model into slices (for example, each slice corresponding to an x-y plane, with successive layers building the z dimension) and encoding each slice into a series of instructions. The instructions sent to the 3D printer may comprise Numerical Control (NC) or Computer NC (CNC) instructions, preferably in the form of G-code (also called RS-274), which comprises a series of instructions regarding how the 3D printer should act. The instructions vary depending on the type of 3D printer being used, but in the example of a moving printhead the instructions include: how the printhead should move, when/where to deposit material, the type of material to be deposited, and the flow rate of the deposited material.

The stent structural elements or the stent itself as described herein may be embodied in one such machine readable model, for example a machine readable map or instructions, for example to enable a physical representation of said stent structural elements or the stent itself to be produced by 3D printing. This may be in the form of a software code mapping of the strut and/or crown and/or instructions to be supplied to a 3D printer (for example numerical code).

Molding, over molding or compression of a preformed part in a shaped mold can also be used to form the stent with the shaped concave luminal and abluminal surface regions and convex side surface regions of the stent structures or to treat a stent to form the concave luminal and abluminal surface regions and convex side surface regions.

Stamping of a preformed tubular stent can also be used to treat the stent to form the desired shape such as shaped concave luminal and abluminal surface regions and convex side surface regions.

5. Laser Shaping

A laser can be used to shape the stent structures. With a laser having the ability to ablate with low energy and layer by layer, such as a femtosecond laser, a laser cutting program can be set to ablate a desired shape of the stent surface regions. In some examples, the laser can be used to create concave luminal and abluminal surface regions and convex side surface regions of the stent structures. A series of laser formed steps can create the convex side surface regions of the struts. In a similar manner, the laser can be used to create the concave luminal or flat or concave abluminal surface regions by a series of small steps along the surface region. The steps can be smoothed out with solvent, sandblasting, tumbling, or the like.

In some examples, a series of overlapping cuts, with each cut narrower than 35 micrometers, narrower than 30 micrometers, or narrower than 25 micrometers can be made from the abluminal surface region to the side surface region of the stent structure to achieve the convex side surface region on the crown, axial strut or other stent structure.

In some examples, the stent can be cut during the laser cutting process with off-axis control such that the axis of the laser beam and the axis of the assist gas supply nozzle on the laser such as a femtosecond laser is eccentrically oriented. This allows the laser to cut material at an angle rather than straight cut, resulting in a curved surface region. This process can be used to form the curved surface regions described herein.

The convex side surface regions of the stent can also be formed using either trepanning or helical drilling. Trepanning is a combined cutting and drilling process, typically performed using a pulsed laser. In trepanning, a through hole is first pierced by percussion drilling and then in a second step the through hole is widened to its final diameter in a circular cutting motion by the laser. In a similar manner, the laser beam can cut the material at an angle to form the curved surface regions. After a first cut at an angle to form the rounded top portion of the strut side surface regions, the laser can cut the rest of the stent pattern with a straight cut. This results in a partially convex side surface region. It is also possible to make the last part of the laser at an angle so that side surface region is fully convex. In helical drilling, a rotational movement of the laser beam is used to create a positive or negative taper at the stent surface regions.

In some examples, where the stent is patterned from a tube by laser cutting and the stent is treated to form a dogbone, barbell, bulbous, elliptical, racetrack or other shape described herein by laser, the processes of patterning and shaping can be performed together.

6. Heat Shaping

As an example, the surface regions of stent can be melted by thermal energy and the material can be redistributed to achieve the desired shaping of the surface regions. In the thermal method heat may be applied in an oven, for a duration and at a temperature to provide convex side surface regions and/or concave luminal and abluminal surface regions. The heating temperature can be controlled to reach the melting temperature of the polymer at the surface regions to be shaped without reaching the melting temperature in the remainder of the stent material.

The temperature for heating a biodegradable polymer material, for example a polylactide polymer or copolymer, for heat shaping can be between 50° C. and 180° C., preferably between 75° C. and 150° C. In some examples, the heating temperature can be above Tg, preferably 30° C. to 100° C. above Tg. In some examples, the heating can be for 1 minute to 5 hours, preferably 5 minutes to 4 hours. The temperature and time of treatment may be adjusted and varied to accomplish the desired treatment and changes to the shape of the structural elements.

It should be appreciated that the required shape may be formed by adding material to the surface region of the original stent structural element, removing from the surface region of the original stent structural element and/or moving material on the surface region of the original stent structural element.

The amount of material added, moved and/or removed will be determined based on the original shape of the surface region of the stent structural element and the required shape of the surface region of the stent structural element. Material may be removed from the outer edge, added to the central portion, moved from the outer edge to the central portion, and/or moved from the outer edge to an adjacent side of the stent structural element to form a convex surface region. Material may be removed from the central portion, added to the outer edge, moved from the central portion to the outer edge, and/or moved from an adjacent side to the outer edge of the stent structural element to form a concave surface region.

It should be appreciated that various techniques may be used to remove material from the structural elements so that the required surface regions have a concave and/or a convex shape. For example, material can be removed from the surface region of a strut using techniques such as negative '3D printing', nanofabrication, microfabrication, photolithography, lithography, and etching.

The stent structural element may also be manufactured to the required shape. For example, the stent structural element may be extruded such that the profile of the stent structural element has the required shape. In some examples the stent prosthesis may be manufactured with stent structural elements of the required shape using a molding process.

The convex side surface regions can also improve flexibility of the stent or stent. The stent with curved axial struts can bend in a multitude of directions compared to axial struts with flat surface regions. For example, a stent with rectangular axial struts or links will bend primarily in two preferred directions because of the flat surface regions of the axial struts. The struts cannot bend in the direction of the edge. However, modified strut cross sections with convex sides provide more freedom to bend in multiple directions and thus provide a more flexible and deliverable stent or stent.

When the struts, crowns and/or other stent structures are coated with a drug for delivery to a lumen, convex side surface regions can provide for a more uniform drug coating and thus can release drug from a substantially more uniform surface region than a square or rectangular strut. Concave luminal and abluminal surface regions also can provide improved directionality of drug delivery to the lumen or vessel wall.

For a substantially amorphous polymer material which is less than 15%, preferably less than 10% crystalline, solvent shaping of the tubular body does not significantly alter the crystalline orientation of the material since the substantially amorphous material is random in crystalline orientation.

Figure 14:
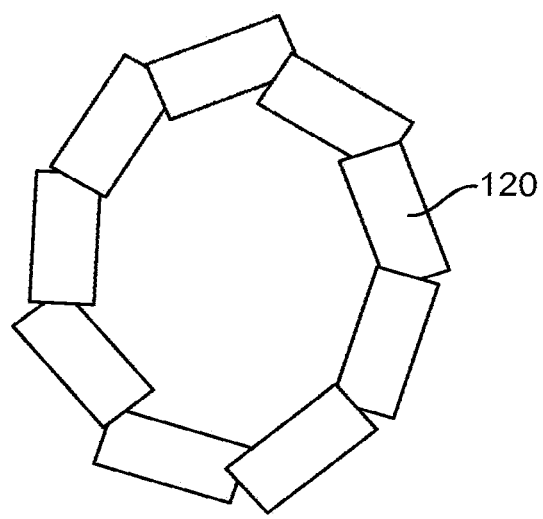
FIG. 14 is a cross section of a crimped stent having unmodified side surface regions.
Figure 15:
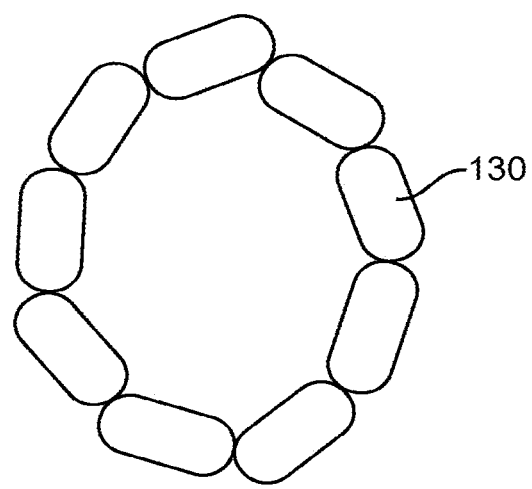
FIG. 15 is a cross section of a crimped stent having modified side surface regions.

Convex side surface regions can also improve crimping of the stent or stent because convex structure sides are more resistant to overlapping struts when crimped from a larger as-cut diameter to a smaller crimped diameter due to the absence of flat surface regions which can catch on one another during crimping. FIG. 14 illustrates an end view of a crimped stent with rectangular cross section stent structural elements 120. The rectangular stent structural elements 120 can overlap and twist due to crimping. The stent structural elements 130 of FIG. 15 having curved side surface regions can reduce or eliminate the overlapping and twisting which occurs with flat rectangular surface regions. FIG. 15 shows a stent body in cross section with convex side surface regions of the stent structural elements. Twisting and rotating of stent structural elements along their axis can happen during expansion as well as during crimping. The convex side surface regions and concave abluminal surface regions prevent or reduce rotating of stent structural elements during crimping and/or during expansion to less than 45 degrees, less than 35 degrees or less than 25 degrees.

Figure 27:
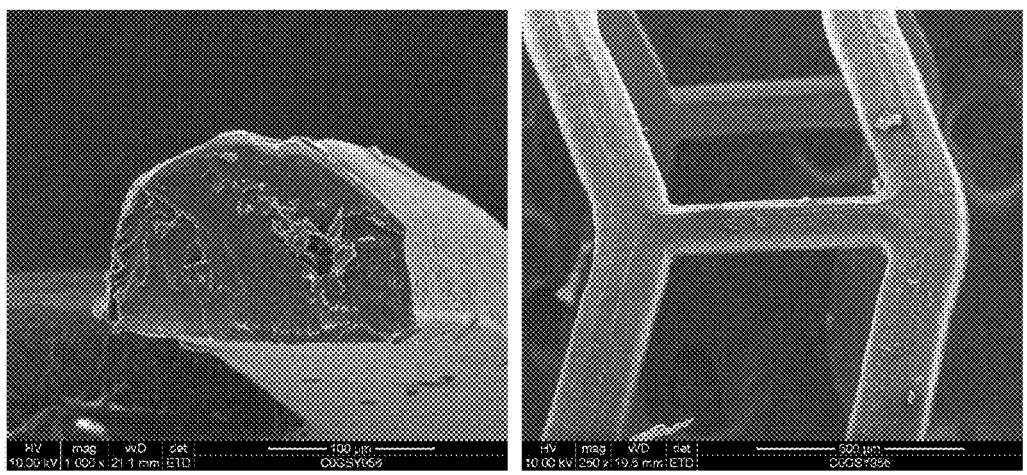
FIG. 27 is an example of an SEM image at about 1000× and about 250× magnification showing maximum thickness near middle and an indentation adjacent to thickest section of the abluminal surface region.

Struts or other stent structures having shaped surface regions as described above can be considered to have oblong, oval, elliptical, near elliptical, circular, near circular, or dogbone like cross sectional shapes. Where the shaping treatment is performed before application of the drug in a preferred embodiment, the drug coating process achieves a product with shaped surface regions as the coating process maintains substantially the same shape. In some examples, in at least some of the treated structural elements where the concave luminal and/or abluminal surface regions join convex side surface regions there is a lip or a ledge which extends along at least some of the structural elements. The lip or ledge may exist at or near one or more of the junctures of the luminal and/or abluminal surface regions and the side surface regions. The lips and or ledges may be between the abluminal and side surface regions or between the luminal and side surface regions such that the lip protrudes outwardly. These lips may extend continuously along a strut and a connected crown of the expandable stent prosthesis in the form of a lip, edge or wave. The thickest part of the cross-section of a structural element may be at the lip. FIG. 24 shows the abluminal lips extending along a strut and along a crown. FIG. 27 shows a lip near or adjacent to the juncture of the luminal and side surface regions.

In some examples, the stent prosthesis cross section has concave luminal and/or abluminal surface regions and convex side surface regions which form a continuous curve across the side surface regions to provide a continuous convex curve in the form of an arc which extends between abluminal and luminal lips. In some examples, at least some abluminal surface regions and at least some luminal surface regions join said side surface regions at a lip and a thickness between an abluminal lip and a luminal lip forms a thickest part of the cross section of said structural elements, while a thickness at a core or substantially a midpoint between the abluminal lips forms a thinnest part of the cross section of said structural elements.

In some embodiments, the biodegradable stent prosthesis comprises a body having a plurality of rings each ring comprises a plurality of struts joined by crowns, wherein each ring is connected to an adjacent ring by at least one link.

In some embodiments, the biodegradable stent prosthesis comprises a body having a plurality of struts joined by crowns.

In some embodiments, the biodegradable stent prosthesis comprises a body having a plurality of rings connected by at least one link, and a plurality of struts joined by crowns.

In some examples, the biodegradable stent prosthesis comprises a body having abluminal surface regions, luminal surface regions, and two side surface regions of each structural component of the stent, along the length of the stent.

In some embodiments, the biodegradable stent prosthesis comprises a polymeric material forming a tubular body, wherein said body comprises a stent pattern having a plurality of struts, crowns and optionally links, each having four surface regions, such that a cross section of said struts is rectangular having a concave abluminal surface region and/or convex side surface region, and a cross section of said crown is substantially rectangular having convex side surface regions and/or optionally a concave abluminal surface region. The cross-section is substantially rectangular in the sense that the dimensions of width and thickness are different.

Although rectangular and square cross sections having four sides are described other cross sections have more than four sides or fewer than four sides are also contemplated.

In some embodiments, the biodegradable stent prosthesis comprises a polymeric material forming a tubular body, wherein said body comprises a stent pattern having a plurality of struts, crowns and optionally links, each having four surface regions, such that a cross section of said struts is substantially square having concave abluminal surface regions, and/or convex side surface regions, and a cross section of said crown is substantially square having convex side surface regions, and/or optionally concave abluminal surface region. The cross-section is substantially square in the sense that the dimensions of width and thickness are substantially the same.

The biodegradable stent prosthesis may be expandable from a crimped configuration to an expanded larger configuration to support a body lumen or a blood vessel.

The biodegradable stent prosthesis may be expandable from a crimped configuration to an expandable larger configuration at body temperature.

The biodegradable stent prosthesis may be expandable from a crimped configuration to an expanded larger configuration and have sufficient strength to support a body lumen or a blood vessel.

The biodegradable stent prosthesis may be circumferentially expandable from a crimped configuration to an expanded larger configuration.

In some embodiments, the biodegradable stent prosthesis comprises a biodegradable polymeric material.

In some embodiments, the biodegradable stent prosthesis comprises a biodegradable metal or metal alloy.

In some embodiments, the biodegradable stent prosthesis comprises a biodegradable polymeric material, and a biodegradable metal or metal alloy.

In some embodiments, the biodegradable prosthesis comprises a degradable polymeric material, said polymeric material is formed as a tubular body using extrusion, dipping, spraying, or printing.

In some embodiments, the biodegradable stent prosthesis comprises a degradable metal or metal alloy, said metal or metal alloy is formed as a tubular body.

In some embodiments, an expandable biodegradable prosthesis comprises an expandable prosthesis body formed from a biodegradable polymeric material, the expandable prosthesis body having a plurality of stent structural elements each having luminal and abluminal surface regions. The plurality of stent structural elements includes a plurality of circumferentially expandable serpentine rings, each serpentine ring including axial struts joined by crowns. At least some of the abluminal surface regions are concave across substantially the width of the stent structural elements. The prosthesis is expandable from a crimped configuration to an expanded larger configuration to support a body lumen.

In some embodiments, the biodegradable stent prosthesis comprises a degradable polymeric material formed as a tubular body, said stent is patterned into a structure comprising a plurality of rings, wherein each ring comprises a plurality of struts and crowns, wherein adjacent rings are connected by at least one link, wherein the stent struts have abluminal and luminal surface regions, wherein at least some of the struts abluminal surface regions are concave across substantially the width of said struts.

In some embodiments, the biodegradable stent prosthesis comprises a degradable polymeric material formed as a tubular body, said stent is patterned into a structure comprising a plurality of rings, wherein each ring comprises a plurality of struts and crowns, wherein adjacent rings are connected by at least one link, wherein the stent struts have abluminal and luminal surface regions, wherein substantially all of the struts abluminal surface regions are concave across substantially the width of said struts.

In some embodiments, the biodegradable stent prosthesis comprises a degradable polymeric material formed as a tubular body, said stent is patterned into a structure comprising a plurality of rings, wherein each ring comprises a plurality of struts and crowns, wherein adjacent rings are connected by at least one link, wherein the stent struts have abluminal and luminal surface regions, and at least one side surface region between the luminal and abluminal surface regions, wherein at least some of the struts abluminal surface regions are concave across substantially the width of said struts, and wherein at least some of the struts side surface regions are convex across substantially the thickness of said struts.

In some embodiments, the biodegradable stent prosthesis is patterned into a structure comprising a plurality of serpentine rings, each ring comprises struts joined by crowns, and wherein adjacent rings are joined by at least one link, said rings have abluminal and luminal surface regions, and two side surface regions between the luminal and abluminal surface regions; wherein at least some of the rings luminal surface regions are concave across substantially the width of said ring, and wherein at least some of the rings side surface regions are convex across substantially the thickness of said ring.

In some embodiments, the stent structural elements comprise side surface regions extending between the luminal and abluminal surface regions, wherein at least some of the side surface regions are convex.

In some embodiments, the expandable prosthesis body is formed from a tube and the formed prosthesis body has been treated to form the concave abluminal surface regions.

In some embodiments, the expandable prosthesis body is formed from a flat sheet and the formed prosthesis body has been treated to form the concave luminal and abluminal surface regions.

In some embodiments, the treatment does not substantially change the weight or mass of the prosthesis body.

In some embodiments, the stent prosthesis is treated to form concave shapes across substantially the width of the stent abluminal surface regions, and convex shapes across substantially the thickness of the stent side surface regions, wherein the weight or mass of the stent prosthesis before treatment and after treatment is substantially the same.

In some embodiments, the stent prosthesis is treated to form concave shapes across substantially the width of the stent abluminal surface regions, and convex shapes across substantially the thickness of the stent side surface regions, wherein the weight or mass of the stent prosthesis before treatment and after treatment are within 15% of each other.

In some embodiments, the stent prosthesis is formed comprising concave shapes across substantially the width of the stent abluminal surface regions, and convex shapes across substantially the thickness of the stent side surface regions, and wherein the weight or mass of the stent prosthesis before treatment and after treatment is substantially the same.

In some embodiments, a method of forming an expandable polymer prosthesis with modified surface regions includes the steps of forming a tubular expandable prosthesis with a plurality of stent structural elements each having a luminal surface region, an abluminal surface region and two side surface regions extending between said luminal and abluminal surface regions by patterning the prosthesis from a polymer tube; and exposing the expandable prosthesis to a treatment for a predetermined period of time to modify the surface regions, wherein resulting modified abluminal surface regions are concave.

In some embodiments of the method the modified side surface regions of the expandable prosthesis are convex.

In some embodiments of the method the treatment changes the shapes of the surface regions and does not substantially change the weight or mass of the prosthesis.

In some embodiments, an expandable prosthesis includes an expandable prosthesis body formed from a plurality of stent structural elements including struts, crowns and optionally links, each having luminal and abluminal surface regions and side surface regions extending between the luminal and abluminal surface regions, wherein at least some of the abluminal surface regions are concave and wherein at least some of the side surface regions are convex, wherein said prosthesis is expandable from a crimped configuration to an expanded larger configuration to support a body lumen.

In some embodiments, the endoprosthesis is patterned from a tube by laser cutting and the laser cut treatment forms the concave abluminal surface regions and convex side surface regions. In some embodiments, the treatment comprises shaping by application of a solvent by at least one of dipping, spraying, or contact with a solvent vapor.

In some embodiments, the treatment includes shaping by tumbling, agitating, deburring, scraping, or sandblasting. In some examples, the processing includes shaping with a laser or heat. The processing can be followed by forming a coating of at least one drug formed over the expandable endoprosthesis body.

In some examples, the endoprosthesis comprises a plurality of circumferentially expandable serpentine rings, each serpentine ring comprises axial struts joined by crowns, wherein one crown joins two adjacent axial struts of a serpentine ring, and wherein the crowns act as hinges allowing the struts to spread as the ring expands circumferentially, at least one link joining adjacent serpentine rings.

The stent endoprosthesis may be formed from a biodegradable polymeric material which has a molecular weight ranging from 100 KDa to 1000 KDa. In some embodiments, the biodegradable polymeric material has an elastic modulus of at least 0.35 GPa, preferably between 0.35 GPa and 1.5 GPa.

The biodegradable polymeric material may comprise one or more of polymers and copolymers. The endoprosthesis may be capable of being expanded from a crimped diameter to a deployed diameter at body temperature without fracture of the endoprosthesis.

The endoprosthesis may comprise a biodegradable polymeric material comprising one or more of: Lactide, poly-DL-Lactide, polylactide-co-gycolide, polylactide-co-polycaprolactone, poly (L-lactide-co-trimethylene carbonate), polytrimethylene carbonate, polyhydroxybutyrate, polyhydroxyvalerate, poly orthoesters, poly anhydrides, polylactide, polyglycolides, polycaprolactone, tyrosine derived polycarbonates, polyiminocarbonates, and copolymers thereof.

In some embodiments, the polymeric material comprises one or more polymers or co-polymers, or polymer blends.

The prosthesis body may be formed as a tube and patterned by laser cutting.

The endoprosthesis is preferably balloon expandable.

In some embodiments, the endoprosthesis is self-expandable.

In some embodiments, the stent prosthesis is self-expandable and balloon expandable.

In some embodiments, a polymer endoprosthesis comprises a tubular expandable endoprosthesis body comprising a polymeric material which has been patterned from a tube to form the stent, said stent comprises a plurality of stent structural elements each stent structural element having a luminal surface region, an abluminal surface region, and two side surface regions extending between said luminal and abluminal surface regions, wherein at least one of the abluminal surface regions is concave, and wherein the two side surface regions are convex.

A drug coating comprising at least one drug may be coated on at least a portion of the expandable endoprosthesis body. The at least one drug may be contained within a coating, preferably a polymeric coating, covering at least a portion of the stent prosthesis.

In an embodiment, a method of forming a polymer endoprosthesis prosthesis with modified surface regions comprises the steps of forming a tubular expandable endoprosthesis with a plurality of stent structural elements each having a luminal surface region, an abluminal surface region and two side surface regions extending between said luminal and abluminal surface regions by cutting the endoprosthesis from a polymer tube and exposing the tubular expandable endoprosthesis to a treatment for a predetermined period of time to modify the surface regions, wherein the resulting modified abluminal surface regions are concave while the modified two side surface regions are convex.

In some embodiments, at least some of the abluminal surface regions of some portions of the polymeric prosthesis are concave and at least some of the side surface regions are concave.

In some embodiments substantially all of the abluminal surface regions of the prosthesis are concave and substantially all of the side surface regions of the prosthesis are convex.

The treatment may change the shapes of the surface regions and not substantially change the weight or mass of the endoprosthesis.

The treatment process may not significantly dissolve the polymeric material from which the endoprosthesis is formed.

The treatment process may not substantially dissolve the polymeric material from which the endoprosthesis is formed.

In some example methods, the treatment does not dissolve more than 10%, more than 15% or more than 20% of the polymeric material from which the endoprosthesis is formed.

In some example methods, the treatment does not substantially degrade the polymeric material from which the endoprosthesis is formed either mechanically or chemically.

Preferably, the treatment shifts polymeric material from at least one surface region to an adjacent surface region without a substantial change in weight or mass before and after treatment.

Preferably, the treatment shifts polymeric material from at least one surface region to an adjacent surface region modifying at least some abluminal surface regions into concave shape and at least some side surface regions into convex surface regions without a substantially change in the weight or mass before and after treatment.

The treatment may shift polymeric material from abluminal and/or luminal surface regions of the stent prosthesis to the side surface regions of the stent prosthesis (or vice versa), preferably without substantially loss of material, more preferably without weight or mass change of more than 5%, most preferably without substantial change in stent weight or mass.

The treatment may shift polymeric material from at least one side surface region to one of luminal or abluminal surface regions of the stent prosthesis, preferably without substantially loss of material, more preferably without loss of more than 5%, most preferably without substantial change in stent weight or mass.

In some embodiments, a method of forming a polymer endoprosthesis prosthesis with a controlled strut thickness includes the steps of forming a tubular expandable endoprosthesis with a plurality of struts by cutting the endoprosthesis from a polymer tube having a first thickness, said endoprosthesis comprising a polymeric material and exposing the tubular expandable endoprosthesis to a solvent for a predetermined period of time to redistribute said polymeric material without substantially dissolving it to adjust a thickness of the plurality of struts to a second thickness, wherein the second thickness is greater than the first thickness.

In some embodiments, a polymer endoprosthesis includes a tubular expandable endoprosthesis body comprising a polymeric material which has been cut from a tube to form an endoprosthesis with a plurality of stent structural elements each having a luminal surface region, an abluminal surface region, and two side surface regions extending between said luminal and abluminal surface regions, wherein the two side surface regions are convex and have a radius of curvature of at least 0.020 mm.

In some embodiments, a polymer endoprosthesis comprises a tubular expandable endoprosthesis body comprising a polymeric material which has been cut from a tube to form an endoprosthesis with a plurality of stent structural elements each having a luminal surface region, an abluminal surface region, and two side surface regions extending between said luminal and abluminal surface regions, wherein the abluminal surface regions of the stent structural elements are shaped to form concave surface regions extending substantially from one side surface region to an opposite side surface region; a coating comprising at least one drug formed over the tubular expandable endoprosthesis body. Preferably, a coating comprising a drug is coated over said abluminal surface region without substantially changing the concave shape.

In some embodiments, a method of forming a polymer endoprosthesis prosthesis with a modified shape includes the steps of forming a tubular expandable endoprosthesis with a plurality of stent structural elements having luminal, abluminal and side surface regions extending between said luminal and abluminal surface regions by cutting the endoprosthesis from a polymer tube having a first thickness and treating the tubular expandable endoprosthesis to increase a thickness of the plurality of stent structural elements between the luminal and abluminal surface regions while decreasing a width of the stent structural elements between the side surface regions by redistributing the polymer. Preferably, the treating increases the thickness of a plurality of stent structural elements but the width of the stent structural elements remains unchanged. The width and thickness may be measured as the maximum dimensions for the width and thickness, taken at the widest or thickest spot on the strut. Although the maximum dimensions can be used, the minimum, median, average or mean dimensions, or whatever is appropriate in the circumstances can be used for dimensions. The changes or no changes can be detected regardless of the measurement protocol selected.

In some embodiments, the biodegradable stent prosthesis comprises a biodegradable polymeric material formed as a tubular body, wherein said tubular body is composed of an abluminal surface region, a luminal surface region, and two side surface regions, wherein the tubular body is patterned into a structure having an abluminal surface region, a luminal surface region, and side surface regions, and wherein the stent is treated after patterning to shift polymeric material from at least one side surface region to said luminal and/or abluminal surface regions.

In some embodiments, the biodegradable stent prosthesis comprises a biodegradable polymeric material formed as a tubular body, wherein said tubular body is composed of an abluminal surface region, a luminal surface region, and at least two side surface regions, wherein the tubular body is patterned into a structure having an abluminal surface region, a luminal surface region, and at least two side surface regions, and wherein the stent is treated after patterning to shift polymeric material from at least some luminal and/or abluminal surface regions to at least one adjacent side surface region, wherein the at least said treated abluminal surface regions become substantially concave, and wherein the at least adjacent side surface regions become substantially convex.

In some embodiments, the biodegradable stent prosthesis comprises a biodegradable polymeric material formed as a tubular body, wherein said tubular body is composed of an abluminal surface region, a luminal surface region, and at least two side surface regions, wherein the tubular body is patterned into a structure having an abluminal surface region, a luminal surface region, and at least two side surface regions, and wherein the stent is treated after patterning to shift polymeric material from at least some side surface regions to at least one adjacent luminal and/or abluminal surface region (or vice versa shifting material from luminal and/or abluminal to side), wherein the at least some treated abluminal surface regions become substantially concave, and wherein the at least some adjacent side surface regions become substantially convex, and wherein the weight or mass of the stent prosthesis before and after said treatment is substantially the same.

In some embodiments, the biodegradable stent prosthesis comprises a biodegradable polymeric material formed as a substantially flat body, wherein said body is composed of an abluminal surface region, a luminal surface region, and at least two side surface regions, wherein the body is patterned into a structure having an abluminal surface region, a luminal surface region, and at least two side surface regions, and wherein the stent is treated after patterning to shift polymeric material from at least some side surface regions to at least on adjacent luminal and/or abluminal surface region, wherein the at least said treated luminal and/or abluminal surface regions become substantially concave, and wherein the at least adjacent side surface regions become substantially convex, and wherein the weight or mass of the stent prosthesis before and after said treatment is substantially the same.

The surface region roughness of treated luminal, abluminal, and adjacent sides may be substantially reduced after treatment. For example, the surface region roughness of treated luminal, abluminal, and adjacent side surface regions, may be substantially reduced after process treatment. In some examples, the root-mean-square roughness (Sq) ranges between 0.5 micrometers to 15 micrometers. In another example the roughness average (Sa) ranges from 0.5 micrometers to 10 micrometers as measured by optical profilometry or atomic force microscopy.

The treated surface regions may increase crystallinity at the surface region of the stent prosthesis by at least 15%.

The treated surface region may have a crystallinity that is substantially different from the core of the treated stent prosthesis by at least 15%, or by at least 20%, or by at least 25%, or by at least 30%. The crystallinity of the treated surface region within 25% depth from the treated surface region may be substantially different from the crystallinity of the said core of the treated stent prosthesis.

In some examples, the crystallinity of the polymeric material after treatment including treatment to shape the structural elements can increase at least 10% or at least 20%, or between 5% and 50% or preferably between 5% and 30%. In some examples the crystallinity of the polymeric material after treatment to shape the structural elements is substantially the same.

The treatment may increase cross linking at the surface region of the stent prosthesis. Increased cross linking results in a stent which absorbs less solvent when exposed to the solvent. The increase in cross linking results in absorption of solvent reduction by at least 10%.

The treated stent prosthesis surface region may have an increased hydrophobicity. This is very helpful when coating the stent prosthesis with a coating or a drug comprising a solvent wherein the absorption of said solvent is reduced by at least 10%. It can also be helpful to delay substantially complete hydration of the stent prosthesis by at least 1 minute.

When fabricating a biodegradable stent prosthesis, it is desirable to design the prosthesis such that the stent design comprising stent structural elements, for example crowns or/and struts, having width to thickness dimensions that are approximately 1:1, or range from approximately 0.8:1 to approximately 1.1:1, such that upon expansion of the biodegradable stent prosthesis said stent structural elements along the length of the stent prosthesis are substantially free from rotating around their axis, or substantially free from rotating more than 45 degrees around their axis. This allows the stent prosthesis to have improved strength such as sufficient strength to support a body lumen, improved uniformity of expansion, and/or be free from fracture upon expanding the stent from a crimped configuration to an expanded larger configuration.

However, such desire is difficult to achieve when using biodegradable material since the biodegradable material are typically weaker material and therefore in order to achieve smaller thickness, the width of such stent prosthesis stent structural elements, for example struts, will be larger than thickness, typically width to thickness ratio are at least 1.2:1, and that contributes to having stent structural elements along the length of the stent prosthesis prone to rotating or twisting upon expanding the stent prosthesis from a crimped configuration to an expanded larger configuration, resulting in lower strength, lower uniformity of expansion, or strut and/or crown fracture, upon expansion of the stent or after expansion. It is therefore desirable to be able to design a biodegradable stent prosthesis that is smaller in thickness, having a width to thickness ratio of at least 1.2:1 wherein the stent structural elements upon expansion or after expansion are substantially free from said stent structural elements rotating, or substantially free from rotating more than 45 degrees around their axis, or substantially free from rotating more than 25 degrees around their axis. Such desire for performance is achieved when fabricating a stent comprising stent structural elements that have at least some of the luminal and/or abluminal surface region concave, and optionally at least some of the sides extending between said luminal and abluminal surface regions convex, said degradable stent prosthesis stent structural elements upon expansion from crimped configuration to an expanded configuration are substantially free from rotating more than 45 degrees around their axis.

In an embodiment, the biodegradable stent prosthesis comprises a biodegradable polymeric material formed as a tubular body using extrusion, dipping, spraying or printing, wherein the stent prosthesis is patterned into a structure comprising stent structural elements, such as struts, wherein said stent structural elements having widths that are at least 1.2 times said stent structural element thickness, wherein the patterned structure comprises luminal, abluminal, and side surface regions, wherein at least some of said stent structural elements having concave abluminal surface regions along the width of said stent structural elements, and optionally wherein at least some of said stent structural elements have at least one convex side surface region extending between said abluminal and luminal surface region, said stent prosthesis is expandable from a crimped configuration to an expanded larger configuration wherein the said stent structural elements remain substantially free from rotating.

In some embodiments, an expandable prosthesis includes an expandable prosthesis body formed from a plurality of stent structural elements each having luminal and abluminal surface regions and side surface regions extending between the luminal and abluminal surface regions, wherein at least some of the luminal and abluminal surface regions are concave and wherein at least some of the side surface regions are convex, wherein said prosthesis is expandable from a crimped configuration to an expanded larger configuration to support a body lumen.

The endoprosthesis may be cut from a tube by laser cutting and the laser cut prosthesis has been processed to form the concave luminal and abluminal surface regions and convex side surface regions. As another possibility, the processing includes shaping by application of a solvent by at least one of dipping, spraying, or contact with a solvent vapor.

The endoprosthesis stent structural elements can include a plurality of circumferentially expandable serpentine rings, each serpentine ring including struts joined by crowns, wherein one strut joins two adjacent crowns of a serpentine ring, and wherein the crowns act as hinges allowing the struts to spread as the ring expands circumferentially, links joining some but not all crowns on adjacent serpentine rings. The treatment may modify the surface regions of all of the stent structures of the endoprosthesis.

In some embodiments, a polymer endoprosthesis includes a tubular expandable endoprosthesis body comprising a polymeric material which has been cut from a tube to form an endoprosthesis with a plurality of struts each having a luminal surface region, an abluminal surface region, and two side surface regions extending between said luminal and abluminal surface regions, wherein at least one of the luminal and abluminal surface regions is concave and the two side surface regions are convex In some embodiments, a method of forming a polymer endoprosthesis with modified surface regions includes the steps of forming a tubular expandable endoprosthesis with a plurality of struts each having a luminal surface region, an abluminal surface region and two side surface regions extending between said luminal and abluminal surface regions by cutting the endoprosthesis from a polymer tube and exposing the tubular expandable endoprosthesis to a treatment for a predetermined period of time to modify the surface regions, wherein the resulting modified luminal and abluminal surface regions are concave while the modified two side surface regions are convex.

The Tg of the polymer comprised in the polymeric stent after the shaping process may be substantially unchanged from before the treatment process.

The crystallinity of the polymer comprised in the polymeric stent after the shaping process may be substantially unchanged from before the treatment process.

The molecular weight of the polymer comprised in the polymeric stent after the shaping process may be substantially unchanged from before the treatment process.

The molecular number of the polymer comprised in the polymeric stent after the shaping process may be substantially unchanged from before the treatment process.

In the polydispersity index of the polymer comprised in the polymeric stent after the shaping process may be substantially unchanged from before the treatment process.

In some embodiments, a method of forming a polymer stent prosthesis with a controlled strut thickness includes the steps of forming a tubular expandable prosthesis with a plurality of struts by cutting the prosthesis from a polymer tube having a first thickness, said prosthesis comprising a polymeric material and exposing the tubular expandable prosthesis to a solvent for a predetermined period of time to redistribute said polymeric material without substantially dissolving it to adjust a thickness of the plurality of struts to a second thickness, wherein the second thickness is greater than the first thickness.

In some embodiments, a polymer endoprosthesis includes a tubular expandable endoprosthesis body comprising a polymeric material which has been cut from a tube to form an endoprosthesis with a plurality of struts each having a luminal surface region, an abluminal surface region, and two side surface regions extending between said luminal and abluminal surface regions, wherein the abluminal surface regions of the struts are shaped to form concave surface regions extending substantially from one side surface region to an opposite side surface region; and a coating comprising at least one drug formed over at least some portions of the tubular expandable endoprosthesis body. The at least one drug may coat all surface regions of the tubular expandable endoprosthesis body.

In some embodiments, a method of forming a polymer stent prosthesis with a modified shape includes the steps of forming a tubular expandable prosthesis with a plurality of struts having luminal, abluminal and side surface regions extending between said luminal and abluminal surface regions by cutting the prosthesis from a polymer tube having a first thickness and treating the tubular expandable endoprosthesis to increase a thickness of the plurality of struts between the luminal and abluminal surface regions while decreasing a width of the struts between the side surface regions by redistributing the polymer.

In some embodiments, the biodegradable stent prosthesis comprises a tubular biodegradable polymeric material, said polymeric material is patterned into a stent capable of radial expansion from a crimped diameter to a deployed larger diameter, wherein the stent comprises a plurality of struts joined by crowns and at least some of the crowns are connected to adjacent crowns, wherein said patterned stent struts and crowns, each have a luminal surface region, an abluminal surface region, and two side surface regions extending between said luminal and abluminal surface regions, wherein at least some abluminal surface regions (optionally substantially all abluminal surface regions) have concave shapes across substantially the width of said abluminal surface regions, and at least some side surface regions (optionally substantially all side surface regions) have convex shapes across the thickness of said side surface regions, wherein the stent in the deployed diameter has sufficient strength to support a blood vessel.

In some embodiments, the biodegradable polymeric stent prosthesis comprises a tubular biodegradable polymeric material, said polymeric material is patterned into a stent capable of radial expansion from a crimped diameter to a deployed larger diameter, wherein the stent comprises a plurality of struts joined by crowns and at least some of the crowns are connected to adjacent crowns, wherein said patterned stent struts and crowns each have a luminal surface region, an abluminal surface region, and two side surface regions extending between said luminal and abluminal surface regions, wherein at least some abluminal surface regions (optionally substantially all abluminal surface regions) have concave shapes across substantially the width of said abluminal surface regions, and at least some side surface regions (optionally substantially all side surface regions) have convex shapes across the thickness of said side surface regions, wherein the stent in the deployed diameter has sufficient strength to support a blood vessel.

In some embodiments, the biodegradable polymeric stent prosthesis comprises a tubular biodegradable polymeric material, said polymeric material is patterned into a stent body capable of radial expansion from a crimped diameter to a deployed larger diameter, wherein the stent body comprises a plurality of struts joined by crowns and at least some of the crowns are connected to adjacent crowns, wherein said patterned stent structural elements each have a luminal surface region, an abluminal surface region, and two side surface regions extending between said luminal and abluminal surface regions, wherein at least some abluminal surface regions (optionally substantially all abluminal surface regions) have concave shapes across substantially the width of said abluminal surface regions, and at least some side surface regions (optionally substantially all side surface regions) have convex shapes across the thickness of said side surface regions, wherein the stent body in the deployed diameter has sufficient strength to support a blood vessel.

In some embodiments, the biodegradable stent prosthesis comprises a tubular biodegradable polymeric material, said polymeric material has a stent pattern, said stent capable of radial expansion from a crimped diameter to a deployed larger diameter, wherein the stent comprises a plurality of struts joined by crowns and at least some of the crowns are connected to adjacent crowns, wherein said stent struts and crowns each have a luminal surface region, an abluminal surface region, and two side surface regions extending between said luminal and abluminal surface regions, wherein at least some abluminal surface regions (optionally substantially all abluminal surface regions) have concave shapes across substantially the width of said abluminal surface regions, and at least some side surface regions (optionally substantially all side surface regions) have convex shapes across the thickness of said side surface regions, wherein the stent in the deployed diameter has sufficient strength to support a blood vessel.

In some embodiments, the biodegradable polymeric stent prosthesis comprises a tubular biodegradable polymeric material, said polymeric material is patterned into a stent capable of radial expansion from a crimped diameter to a deployed larger diameter, wherein the stent comprises a plurality of struts joined by crowns and at least some of the crowns are connected to adjacent crowns, wherein said patterned stent structural elements each have a luminal surface region, an abluminal surface region, and two side surface regions extending between said luminal and abluminal surface regions, wherein at least some abluminal surface regions (optionally substantially all abluminal surface regions) have concave shapes, and at least some side surface regions (optionally substantially all side surface regions) have convex shapes, wherein the stent in the deployed diameter has sufficient strength to support a blood vessel.

In some embodiments, the biodegradable stent prosthesis, comprising a biodegradable polymeric material, said polymeric material is patterned into a stent capable of expansion from a crimped diameter to a deployed larger diameter, wherein the patterned stent comprises a plurality of struts, crowns, and optionally links connecting at least some adjacent crowns, wherein said patterned stent struts, crowns, and links each have a luminal surface region, an abluminal surface region, and two side surface regions extending between said luminal and abluminal surface regions, wherein at least some abluminal surface regions (optionally substantially all abluminal surface regions) have concave shapes across substantially the width of said abluminal surface regions, and at least some side surface regions (optionally substantially all side surface regions) have convex shapes across the thickness of said side surface regions, wherein the patterned stent in the deployed diameter has sufficient strength to support a blood vessel. The polymeric material may be formed as a tubular body.

In some embodiments, the biodegradable stent prosthesis comprises a biodegradable polymeric material, said polymeric material is patterned into a stent capable of expansion from a crimped diameter to a deployed larger diameter, wherein the patterned stent comprises a plurality of struts, crowns, and optionally links connecting at least some adjacent crowns, wherein said patterned stent struts, crowns, and links each have a luminal surface region, an abluminal surface region, and two side surface regions extending between said luminal and abluminal surface regions, wherein at least some abluminal surface regions (optionally substantially all abluminal surface regions) have concave shapes along substantially the width of said abluminal surface regions, and at least some side surface regions (optionally substantially all side surface regions) have convex shapes along the thickness of said side surface regions, wherein the patterned stent in the deployed diameter has sufficient strength to support a blood vessel. The polymeric material may be formed as a tubular body.

In some embodiments, the biodegradable polymeric stent prosthesis comprises a biodegradable polymeric material, said polymeric material formed as a tubular body and patterned into a stent capable of expansion from a crimped diameter to a deployed larger diameter, wherein the patterned stent comprises a plurality of struts joined by crowns wherein at least some adjacent crowns are connected, wherein said patterned stent struts and crowns, each have a luminal surface region, an abluminal surface region, and two side surface regions extending between said luminal and abluminal surface regions, wherein at least some abluminal surface regions are (optionally substantially all abluminal surface regions) have concave shapes across substantially the width of said abluminal surface regions, and at least some side surface regions (optionally substantially all side surface regions) have convex shapes across the thickness of said side surface regions, wherein the patterned stent in the deployed diameter has sufficient strength to support a blood vessel.

The concave abluminal surface regions and convex side surface regions, may substantially increase the surface region area along the length of stent prosthesis, while reducing surface region porosity of the luminal and side surface regions.

The concave abluminal surface regions and convex side surface regions, may substantially increase the surface region area along the length of stent prosthesis, while substantially maintaining surface region porosity of the luminal and side surface regions.

The patterned stent may expand from a crimped configuration to a larger expanded configuration substantially free from rotation of patterned stent struts, crowns, and optionally links.

The patterned stent may expand from a crimped configuration to a larger expanded configuration having rotation of patterned stent struts, crowns, and optionally links, less than 45 degrees.

In some embodiments, the biodegradable stent prosthesis, comprises a biodegradable polymeric material, said polymeric material is patterned into a stent capable of radial expansion from a crimped diameter to a deployed larger diameter, wherein the patterned stent comprises a plurality of struts joined by crowns wherein at least some adjacent crowns are connected, wherein said patterned stent struts and crowns each have a luminal surface region, an abluminal surface region, and two side surface regions extending between said luminal and abluminal surface regions, wherein the patterned stent is treated and at least some abluminal surface regions (optionally substantially all abluminal surface regions) are modified from being substantially convex shapes to become flat or have a concave shape across substantially the width of said abluminal surface regions, and at least some side surface regions (optionally substantially all side surface regions) are modified from being substantially flat shapes to substantially convex shapes across the thickness of said side surface regions, wherein the patterned stent in the deployed diameter has sufficient strength to support a blood vessel.

In some embodiments, the biodegradable stent prosthesis, comprises a biodegradable polymeric material, said polymeric material is patterned into a stent capable of expansion from a crimped diameter to a deployed larger diameter, wherein the patterned stent comprises a plurality of struts joined by crowns wherein at least some adjacent crowns are connected, wherein said patterned stent struts and crowns each have a luminal surface region, an abluminal surface region, and two side surface regions extending between said luminal and abluminal surface regions, wherein the patterned stent is treated and at least some side surface regions (optionally substantially all side surface regions) are modified from being substantially flat shapes to substantially convex shapes across the thickness of said side surface regions, wherein the patterned stent in the deployed diameter has sufficient strength to support a blood vessel.

The polymeric material may be formed from a tubular body.

The biodegradable prosthesis may be a polymeric biodegradable prosthesis.

In some embodiments, the biodegradable polymeric stent prosthesis, comprises a biodegradable polymeric material, said polymeric material is patterned into a stent capable of radial expansion from a crimped diameter to a deployed larger diameter, wherein the patterned stent comprises a plurality of struts joined by crowns wherein at least some adjacent crowns are connected, wherein said patterned stent struts and crowns each have a luminal surface region, an abluminal surface region, and two side surface regions extending between said luminal and abluminal surface regions, wherein the patterned stent is treated and at least some side surface regions (optionally substantially all side surface regions) are modified to substantially convex shapes across the thickness of said side surface regions, wherein the patterned stent in the deployed diameter has sufficient strength to support a blood vessel.

In some embodiments, the biodegradable polymeric stent prosthesis comprises a biodegradable polymeric material, said polymeric material formed as a tubular body and patterned into a stent capable of expansion from a crimped diameter to a deployed larger diameter, wherein the patterned stent comprises a plurality of struts joined by crowns wherein at least some adjacent crowns are connected, wherein said patterned stent struts and crowns each have a luminal surface region, an abluminal surface region, and two side surface regions extending between said luminal and abluminal surface regions, wherein the patterned stent is treated and at least some abluminal surface regions (optionally substantially all abluminal surface regions) are modified to substantially concave shapes across substantially the width of said abluminal surface regions, and at least some side surface regions (optionally substantially all side surface regions) are modified to substantially convex shapes across the thickness of said side surface regions, wherein the patterned stent in the deployed diameter has sufficient strength to support a blood vessel.

The treatment of the stent prosthesis to modify the abluminal surface regions to concave shapes and the side surface regions to convex shapes may allow the polymeric material to flow from one surface region to an adjacent surface region.

The treatment of the stent prosthesis to modify the abluminal surface regions to concave shapes and the side surface regions to convex shapes may allow the polymeric material to flow from one surface region to an adjacent surface region without substantially dissolving the polymeric material.

The treatment of the stent prosthesis to modify the abluminal surface regions to concave shapes and side surface regions to convex shapes may allow the polymeric material to flow from one surface region to an adjacent surface region, without substantially changing the stent pattern.

The treatment of the stent prosthesis to modify the abluminal surface regions to concave shapes and the side surface regions to convex shapes may increase hydrophobicity of said surface regions, preferably by at least 15%, more preferably by at least 30%, most preferably by at least 50%.

The treatment of the stent prosthesis to modify the abluminal surface regions to concave shapes and the side surface regions to convex shapes may allow the polymeric material to flow from one surface region to an adjacent surface region.

The treatment of the stent prosthesis to modify the abluminal surface regions to concave shapes and the side surface regions to convex shapes may prevent said surface regions from rotating around their axis upon expansion of the stent prosthesis from a crimped configuration to an expanded larger configuration to support a blood vessel.

The treatment of the stent prosthesis to modify the abluminal surface regions to concave shapes and the side surface regions to convex shapes may allow the polymeric material to flow from one surface region to an adjacent surface region, without substantially changing the weight or mass of the stent prosthesis.

The biodegradable stent prosthesis may be a polymeric biodegradable stent prosthesis. As an example, the biodegradable polymeric stent prosthesis may be substantially all comprised of polymeric material. In some examples, the polymeric biodegradable stent prosthesis is substantially all comprised of polymeric material and metallic radiopaque markers. In some examples, the polymeric biodegradable stent prosthesis is substantially all comprised of polymeric material and non-polymeric radiopaque markers. In some examples, the polymeric biodegradable stent prosthesis is substantially all comprised of polymeric material and some non-polymeric material.

In some embodiments, the treatment of the stent prosthesis to modify the abluminal surface regions to concave shapes or to a concave shape provides abluminal surface regions having a concave shape, but not necessarily identical concave shapes. Similarly, the treatment of the stent prosthesis to modify the side surface regions to convex shapes or to a convex shape provides side surface regions having a convex shape but not necessarily identical convex shapes. The resulting shapes may vary in radii of curvature and where on the strut, crown or link the midpoint of the curve occurs.

The polymeric degradable stent may be formed from a tubular body by extrusion, dipping, spraying, or printing, wherein the tubular body is formed and patterned at 1.1 to 1.5 times or 1.1 to 1.3 times an intended deployed diameter of the stent (labeled nominal diameter), and treating the patterned stent to form concave shapes on at least some abluminal surface regions of the struts and crowns, and convex shapes on at least some side surface regions of said struts and crowns. The stent prosthesis may then be coated with a drug and polymer matrix maintaining the concave abluminal surface regions and convex side surface regions, may then be crimped onto a delivery system, packaged, and sterilized. Optionally the tube or stent is heated at a temperature ranging between 50 degrees and 150 degrees Celsius for between 1 minute and 5 hours, before patterning and/or after patterning, one or more times.

In some embodiments, the stent prosthesis formed from a substantially continuous tubular body using extrusion, spraying, dipping, molding, or printing; said tubular body has been formed into a stent comprising a pattern of structural elements being radially expandable from a crimped configuration to an expanded larger configuration and have sufficient strength in the deployed configuration to support a body lumen; wherein at least some of said structural elements cross sections surface regions extending between an abluminal surface region and a luminal surface region is bulbous; and optionally wherein the thickness between the abluminal and luminal surfaces changes across the width of said structural elements wherein the thickest point is substantially towards the sides of said structural elements wherein the difference in thickness between said thickest point and thinnest point (measured across the abluminal and luminal surfaces and not across the bulbous or convex side region) ranges between 1 micrometer and 15 micrometer, preferably between 2 micrometer and 10 micrometer, more preferably between 3 micrometer and 7 micrometer; wherein the stent structural elements are coated with a coating comprising a drug which coating contours to said structural elements surface regions shapes providing a thickness difference between the thickest point and the thinnest point (measured across the abluminal and luminal surfaces and not across the bulbous or convex side region) across the width of said structural elements with the coating included ranges between 1 micrometer and 15 micrometer, preferably ranges between 2 micrometer and 10 micrometer, more preferably ranges between 3 micrometer and 7 micrometer. The width of the abluminal surface region of the structural element is generally that portion which would contact the body lumen or blood vessel upon deployment.

When the stent structural elements are coated with a drug/polymer composition, the drug/polymer coating has a thickness which is substantially constant along the abluminal, luminal and side surfaces of the structural elements, and wherein a variation in coating thickness is less than 20%, less than 10% or less than 5% across any one or more of the abluminal, luminal or side surfaces.

In some examples at least some structural elements cross sections side surface regions extend outwardly forming a bulbous convex region; wherein said convex region has a widest and narrowest points across the thickness of said structural elements and wherein the widest point is substantially about the center of said structural elements side surface regions, wherein the narrowest point is substantially about the ends (top and bottom) of said structural elements side surface region, wherein the difference between the widest and narrowest point ranges between 4 micrometer and 30 micrometer, preferably ranges between 5 micrometer and 20 micrometer, most preferably ranges between 6 micrometer and 15 micrometer. Optionally, the abluminal surface region cross section is concave in shape with the difference between thickest and thinnest points across the width of said structural element (the thinnest point not including or considering the thickness of the bulbous or convex side region) ranges between 1 micrometer and 10 micrometers.

In some examples, at least some structural elements cross section has a bulbous surface region extending between an abluminal surface region to a luminal surface region wherein the bulbous surface region comprises portions of the luminal and abluminal surface regions and the side regions, wherein the bulbous surface regions forms variable thicknesses and widths across the thickness and widths of said structural elements; wherein said structural elements are coated with a coating comprising a drug and a polymer, wherein said coating contours to the shape of said surface regions maintaining a difference in thickness and widths across the thickness and widths of said structural elements cross sections. In some examples the bulbous surface region extending between the abluminal and luminal surface regions begins at the edges of the abluminal and luminal surface regions curving up in a dogbone shape and then continuing into the convex curvature of the bulbous shape. It is at this curving up or concave portion of the bulbous shape that the greatest thickness of the structural element often occurs.

In some examples the abluminal surface has a substantially concave shape across the width of the at least some structural elements cross sections, wherein the concave shape is formed between two bulbous surface region on said abluminal surfaces.

In some examples the stent prosthesis structural elements have a coating comprising a mixture of drug and polymer, said coating is coated onto said structural elements wherein said coating contours to the shape of said structural elements abluminal, luminal, and side surfaces.

In some examples the stent prosthesis structural elements have a coating comprising a mixture of drug and polymer, said coating is coated onto said structural elements wherein said coating contours to the shape of said structural elements substantially concave abluminal surface shape, substantially concave luminal surface shape, and convex side surface shapes; said coating substantially maintains concave abluminal surface shape, concave luminal surface shape, and convex side surface shapes.

In some examples, upon application of the coating an outer surface area of the structural elements is not substantially changed or is not changed by more than 5%, by more than 10% or by more than 20%.

In some examples, upon application of the coating a cross sectional area of the structural elements in not substantially changed or is not changed by more than 5%, by more than 10% or by more than 20%.

In some examples the coating comprises a drug wherein the total drug dose ranges between 50 micrograms and 200 micrograms for an 18 mm stent prosthesis.

In some examples the surface region on at least some abluminal surfaces have a lip or an edge across the abluminal surface region, wherein said lip have a thickness that is different from adjacent abluminal surface region, wherein the difference in thickness ranges between 2 micrometer and 10 micrometer.

In some examples, the stent prosthesis has concave luminal and/or abluminal surfaces which join convex side surfaces at a lip which extends along at least some of the structural elements including struts, crowns and links. The lip forms a thickest portion of the structural element cross section. As shown in FIGS. 2A-2C and FIGS. 23 and 24, the lip may be in the shape of a wave where the concave and convex surfaces meet. FIG. 24 shows the abluminal lips extending continuously along a strut and a connected crown.

In some examples, the stent prosthesis has a concave abluminal surface and two lips extending along all structural elements of the stent prosthesis.

In some examples, the stent prosthesis cross section has concave luminal and/or abluminal surfaces and convex side surfaces which form a continuous curve across these surfaces without flat portions or without substantial flat portions. For example, the convex side surfaces provide a continuous curve in the form of an arc from an abluminal lip to a luminal lip without flat portions. In some examples, the arc shape of the side surfaces may have a radius of curvature of about 0.02 to about 0.125 or about 0.05 to about 0.075. The arc shape extends between the abluminal and luminal lips or edges.

In some examples, the convex arc shape of the two side surfaces has no visible flat surfaces under a magnification such as SEM magnification of 1000×.

In some examples, the crimping of the stent prosthesis having convex arc shaped side surfaces results in a point contact or line contact between the arc shaped surfaces or between the surfaces and the balloon material. In some examples, the crimping of the stent prosthesis having convex arc shaped side surfaces results in no contact between the arc shaped surfaces. In some examples, the crimping of the stent prosthesis having convex arc shaped side surfaces results in contact between the arc shaped surfaces and the balloon material.

In some examples, a thickness between an abluminal lip and a luminal lip forms a thickest part of the cross section, while a thickness at a midpoint or substantially a midpoint between the two luminal lips or between the two abluminal lips forms a thinnest part of the cross section. A difference between the thickest and thinnest points of the cross section is at least 2%, at least 5%, at least 10%, at least 20%, or at least 30% of the maximum thickness. In some examples, a difference between the thickest and thinnest points of the cross section is 2% to 30%, 2% to 15% or 2% to 10% of the maximum thickness.

Figure 23:
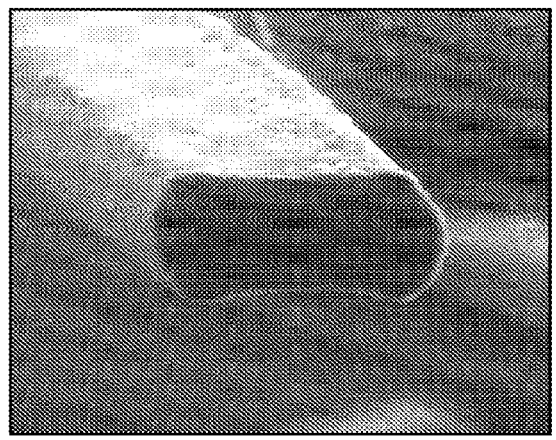
FIG. 23 is an SEM image at 1000× magnification showing a cross section of a further stent structural element showing concave a abluminal surface and convex side surfaces, wherein the region extending between the abluminal and luminal surfaces is bulbous, or dogbone, wherein the structural element shows variable thickness and variable width.

In some examples at least some structural elements abluminal surfaces are concave across the width of said abluminal surfaces all along the entire length of said structural element as shown in FIGS. 23 and/or 24.

In some examples at least some structural elements side surfaces are convex across the thickness of said side surfaces along the length of said side surfaces as shown in FIGS. 23 and/or 24.

In some examples, at least some structural elements have a concave abluminal surface, bulbous, dogbone, or convex side surface and a lip formed along the length of said structural element.

In some examples, the abluminal surface region has a convex shape across the width of said abluminal surface, while the luminal surface region has a convex, concave or substantially flat shape. In some examples, the abluminal surface region has a convex shape across the width of said abluminal surface, while the luminal surface region has concave or substantially flat shape and the side surfaces are substantially flat or convex. In some examples, the abluminal surface region has a convex shape across the width of said abluminal surface with a concave depression at about the mid-point of said abluminal surface, while the luminal surface region has a concave or substantially flat shape and the side surfaces are substantially flat or convex. In some examples both luminal and abluminal surface regions of said structural elements are substantially flat. In other examples both abluminal and luminal surface regions are convex wherein said structural element thickest point is about a midpoint across the abluminal and luminal surface regions, or wherein the structural element thickest point is about a midpoint across the width of said structural element. In some examples of any of the previous examples the surface region extending between luminal and abluminal surface regions is convex.

In some examples the treatment to shape the structural elements uses two or more solvents or other chemical material in ratios ranging from 2% to 95% for each solvent or other chemical material, preferably in ratios ranging from 5% to 80% for each solvent or other chemical material. In some examples of using two or more solvents or other chemical material, at least one solvent or other chemical material is capable of dissolving the material substantially completely within 24 hours. In some examples of using one or more solvents or other chemical material to treat the polymeric material to shape it into the desired abluminal, luminal, and/or side surfaces, the treatment ranges from 0.1 seconds to 1 hour, preferably from 1 second to 1 minute, most preferably from 1 second to 30 seconds. In some examples of treating using one or more solvent or other chemical material the stent polymeric material structural elements are sprayed, dipped, or brushed with solvent or other chemical material. In some examples of treating with solvent or other chemical material the stent pattern is substantially maintained after treatment with the solvents or other chemical material.

In a preferred example, the biodegradable stent is heat treated one or more times after patterning and before crimping. Heat treating the biodegradable stent after patterning and before crimping provides for at least some of the following: increased radial strength in the deployed configuration. aligning the polymeric material orientation in the radial direction, increased orientation of the polymeric material in the radial direction, and reduced residual solvent in the stent. In one example, heat treating the biodegradable stent after patterning and after treatment to form the desired shape cross sectional shape for the struts and/or crowns and before crimping provides for substantially maintaining the stent pattern. Heat treating the biodegradable stent after patterning and before crimping provides for increased radial strength in the deployed configuration. In a preferred example the stent radial strength increases by at least 20%, in another preferred example, the stent radial strength increases in the range of 15% to 50%. The heat treatment of the biodegradable stent after patterning and before crimping is to a temperature ranging between Tg and Tm of the polymeric material, or between 70° C. and 150° C., or between 90° C. and 120° C., typically for a time period ranging from 1 min to 10 hours, preferably from 5 minutes to 5 hours, more preferably from 1 hour to 3 hours; and then the biodegradable stent is cooled to a lower or to an ambient temperature over a time period ranging from 1 second and 30 minutes. The biodegradable stent is heat treated after patterning and before crimping while substantially maintaining the diameter of the patterned stent or so that the stent diameter post heat treatment is reduced by less than 15% of the patterned diameter. This heat treatment substantially maintains the diameter of the patterned stent but there may be a slight reduction in size following the heat treatment, that is, a reduction by a magnitude ranging between 1% and 15% of the patterned stent diameter or from 0.1 mm to 1 mm of the patterned stent diameter. The biodegradable stent is formed at an initial diameter and patterned at the same diameter (1.1-1.5 times the intended deployed diameter). The heat treatment after patterning and before crimping substantially maintains the as-formed diameter and diameter of the stent before patterning. In another example, the biodegradable stent is heat treated after patterning and before crimping while substantially maintaining the stent initial formed diameter. The heat treatment of the biodegradable stent after patterning and before crimping does not substantially alter or deform the stent pattern or the stent pattern geometry. The heat treatment of the biodegradable stent after patterning and before crimping may increase crystallinity by at least 10%, preferably by at least 15%, more preferably by at least 20%, compared to the crystallinity of the polymeric material before heat treatment. But in some instances, the heat treatment of the biodegradable stent after patterning and before crimping does not substantially change the crystallinity of the polymeric material. In one example, the biodegradable stent is heated after patterning and before crimping while having a mandrel through the patterned stent, or having a structure through the patterned stent, or not having any structure or mandrel through the stent. In another example, the biodegradable stent is heat treated after patterning and before crimping forming the desired strut and/or crown cross sectional shapes.

In another example, the biodegradable stent is treated after patterning and before crimping to form the desired strut and/or crown cross sectional shapes, and then heat treated at a temperature above the Tg of the polymeric material before crimping, preferably said heat treatment is at a temperature between 70° C. and 150° C., without substantially changing the stent pattern or without substantially changing the stent diameter, and then crimping said stent to a smaller configuration while being heated at a temperature ranging between 40° C. and 55° C., preferably while being heated at a temperature below the Tg of the polymeric material. The treatment to shape the struts and/or crowns may be one or more of chemical treatment, heating, mechanical shaping, laser shaping, or blasting. The chemical treatment may comprise contact with one or more solvents.

In another example, the biodegradable stent is heat treated after patterning and before crimping, said heat treatment at a temperature above Tg, preferably said heat treatment at a temperature between 70° C. and 150° C., without substantially changing the stent pattern or without substantially changing the stent diameter, and then crimping said stent to a smaller configuration while being heated at a temperature below Tg, preferably ranging between 40° C. and 55° C.

Before deployment, the stent is crimped to a smaller configuration in a crimper for a period of time ranging from 1 sec to 10 minutes, preferably 1 minute to 5 minutes, at a temperature about or below Tg, or within 5 degrees C. higher than Tg, or within 5 degrees C. lower than Tg, or ranging between 40° C. and 50° C. The stent is typically held after crimping at said temperatures for 1 sec to 10 minutes, preferably 10 sec to 5 minutes, more preferably 20 sec to 1 minute. The stent is typically cooled after crimping for a time period ranging from 1 second to 10 minutes, preferably 30 seconds to 5 minutes, more preferably 1 minute to 3 minutes. Then the stent is sheathed after crimping on a delivery system within a time period ranging between 1 seconds to 1 hour, preferably 1 second to 5 minutes.

The surface modification to the structural elements of the biodegradable stent may include heat treating the stent at greater than 15° C. above Tg of polymer material prior to a treatment with one or more solvents; varying the treatment time in the first solvent at ambient temperature with agitation for a time ranging from 0.5 seconds to 5 seconds, followed by a second solvent of, for example, ethanol for time ranging from 0.5 seconds to 30 seconds while maintaining agitation, then heat treating the stent at a temperature above the boiling point of the first solvent for a time ranging from 1 minute to 5 hours while supporting the stent with a mandrel to prevent shrinkage, where in the first solvent can at least substantially dissolve the polymer and the second solvent does not substantially dissolve the polymer. The overall treatment with the two solvents is under conditions such that the polymeric material of the biodegradable stent does not substantially dissolve. The solvent treatment smoothes the surface of the stent prosthesis to remove rough edges, burrs or sharp edges.

Figure 26:
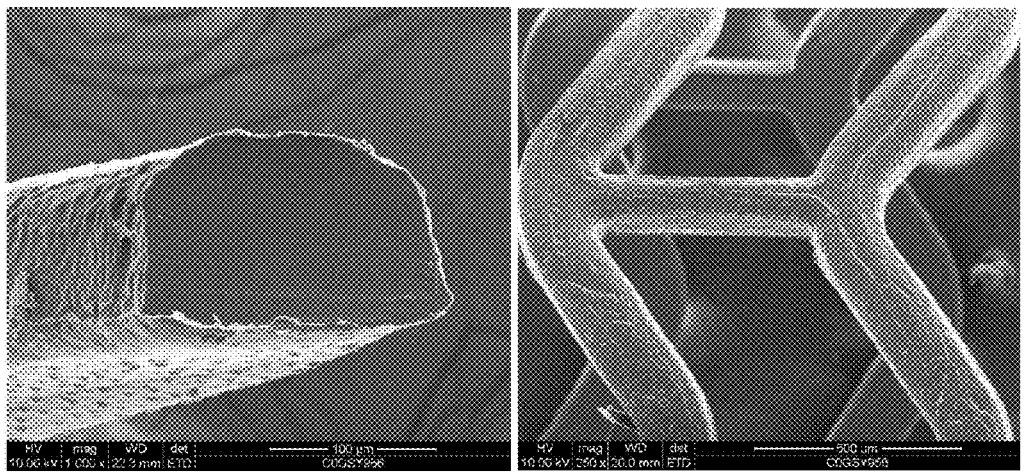
FIG. 26 is an example of an SEM image at about 1000× and about 250× magnification showing maximum thickness about middle of strut cross section, convex abluminal surface region.
Figure 28:
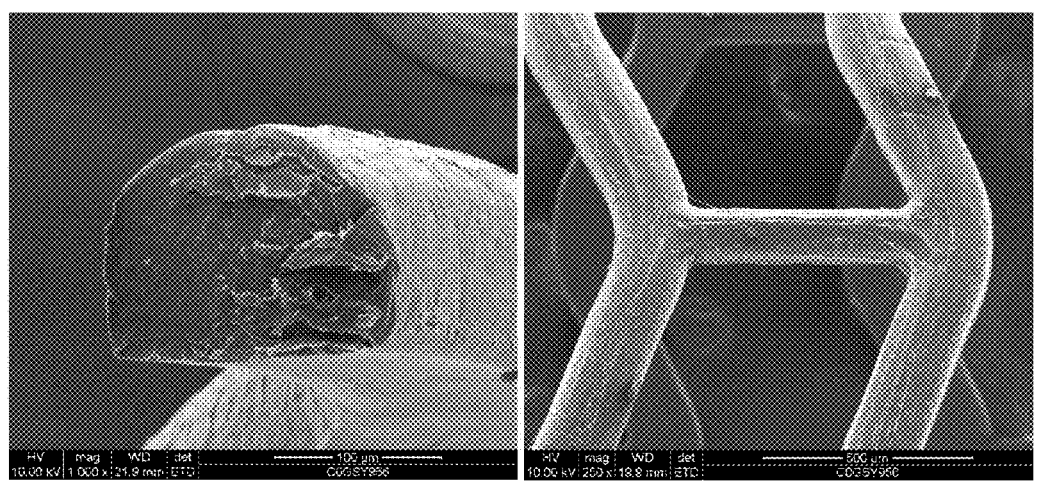
FIG. 28 is an example of an SEM image at about 1000× and about 250× magnification showing maximum thickness near middle of the abluminal surface region of the strut cross section and convex sides.

FIGS. 26, 27 and 28 show struts examples of images of the shape of the treated struts and/or crowns and also the strut and/or crowns as in the stent prosthesis. FIG. 29 shows an example: The concave shape at the abluminal surface of the strut cross section was 25 to 100 μm wide and 0 to 25 um deep. The maximum thickness was at or near the center of the strut cross section approximately 110 to 140 um thick and the radius of curvature of the convex shape mating to the abluminal surface was approximately 66 μm.

In one example, the side surface of the strut cross section is convex. In one example the luminal surface of the strut cross section is concave. In one example, the luminal surface of the strut cross section is substantially flat. In one example, the luminal surface of the strut cross section is convex.

In one example, the radius of curvature of the convex shape of the abluminal surface region which would contact or mate with the surface of the vessel wall ranges from 25 micron to 100 micron, preferably between 50 micron to 75 micron.

It can be appreciated that all the examples within this application are applicable to all biodegradable materials including polymeric and metallic materials. It can also be appreciated that all the examples of forming with a desired shape and treating to form a desired shape are applicable to all biodegradable materials including polymeric and metallic materials.

EXAMPLES

Example 1

Biodegradable polymer stents made from polylactide based polymer were treated with a solvent of 4 parts dichloromethane (methylene chloride) and 6 parts ethanol for 5 seconds and rinsed with ethanol for 3 seconds. Both treated and non-treated stents were then heat treated for 3 hours at 90 deg. C. They were coated with a drug matrix coating and sterilized by Ebeam. The stents were tested for radial strength using an Instron connected to an iris based tester. Treated and untreated stents were chosen based on their similarity in thickness and width to show the benefits of treatment in increasing strength for the same or similar strut profile. As shown in Table 1, the radial strength of the treated stents with modified structure cross section of convex sides and concave luminal and abluminal surface region were higher by at least 15% than the similarly sized stents with substantially rectangular struts (non-treated).

TABLE 1

Summary of Radial Strength

| | Strut Thickness | | Strut Width | | Radial Strength | |
|---|---|---|---|---|---|---|
| | inches | micrometer | In | micrometer | (psi) | n |
| Treated | 0.0043 | 110 | 0.0074 | 188 | 13.7 | 3 |
| Non-Treated | 0.0046 | 116 | 0.0074 | 188 | 11.9 | 4 |

FIG. 2A shows a cross section of a stent strut after treatment. The stent cross section before treatment had substantially rectangular laser cut struts. The stent of FIG. 2A is shown before coating with drug matrix.

The measurements of Table 2 were taken according to the following procedure. However, other procedures may also be used for measurements. Deploy the stents with a balloon catheter according to standard procedures and then dry in vacuum overnight or until there is no visible moisture on the stent. Support the sample with a pin gauge inside the stent prior to cutting the sample across a strut. Mount the samples on the SEM staging using a piece of double tape and then slightly bend the strut such that the cut edge is accessible by the SEM. Under the SEM, locate the first area of interest and then orient the view such that the cut surface is viewed "straight on" as much as possible. Scan the cross-sectioned surface with magnification, such as 1000×, 1200× or 1500× magnification. A strut measurement can be taken in the middle of the strut using the SEM software or at a point of maximum or minimum thickness or width.

The strut after treatment has a narrower width and a slightly greater thickness as shown in Table 2 below.

TABLE 2

Summary of Dimension Changes with Treatment

| | Strut Thickness | | Strut Width | |
|---|---|---|---|---|
| | Inches | micrometers | Inches | micrometers |
| Before Treatment | 0.0032 | 81 | 0.0080 | 203 |
| After Treatment | 0.0043 | 116 | 0.0074 | 188 |

For the particular treatment process in this Example, the struts after treatment have convex side surface regions and have a slight concavity in the luminal and abluminal surface regions. The strut dimensions given in Table 2 are maximum dimensions for the width and thickness, taken at the widest or thickest spot on the strut. According to this example, the treatment resulted in a 43% increase in strut thickness and a 7% decrease in strut width.

A percent shape modification treatment, or amount of change in shape, can be calculated by measuring at one cross section the minimum strut width, generally at the luminal or abluminal surface region of the strut ($W_{min}$) and the maximum strut width ($W_{max}$) which occurs near a midpoint between the luminal or abluminal surface region of the strut and calculating percent treatment=$[1-(W_{min}-W_{max})]\times100$ as shown in Table 3. In some examples, the percent shape modification treatment is at least 10%, or at least 20%, or at least 30% or at least 40%.

TABLE 3

Percent Treatment

| | Ring 1 Strut Width (in) | | Middle Ring Strut Width (in) | |
|---|---|---|---|---|
| Unit # | | | | |
| 3 × 28 mm | Max | Min | Max | Min* |
| 1 | 0.0073 | 0.0035 | 0.0075 | 0.0048 |
| 2 | 0.0073 | 0.0043 | 0.0074 | 0.0045 |
| 3 | 0.0073 | 0.0044 | 0.0071 | 0.0045 |
| 4 | 0.0074 | 0.0042 | 0.0073 | 0.0041 |
| 5 | 0.0072 | 0.0045 | 0.0068 | 0.0031 |
| Average | 0.0073 | 0.0042 | 0.0072 | 0.0042 |
| Low | 0.0072 | 0.0035 | 0.0068 | 0.0031 |
| High | 0.0074 | 0.0045 | 0.0075 | 0.0048 |
| % shape modification Treatment | | | 43% | |

| | Ring 1 Strut Width (in) | | Middle Ring Strut Width (in) | |
|---|---|---|---|---|
| Unit # | | | | |
| 3 × 14 mm | Max | Min | Max | Min* |
| 1 | 0.0071 | 0.0045 | 0.0071 | 0.0044 |
| 2 | 0.0071 | 0.0047 | 0.0069 | 0.0046 |
| 3 | 0.0078 | 0.0048 | | |
| Average | 0.0074 | 0.0047 | 0.0070 | 0.0045 |
| Low | 0.0071 | 0.0045 | 0.0069 | 0.0044 |
| High | 0.0078 | 0.0048 | 0.0071 | 0.0046 |
| % Treatment | | | 37% | |

The treated stents of Example 1 were found to have no significant weight/mass change after treatment. This shows that the solvent is not removing polymer from the stents, but is instead redistributing the polymer material to modify the shape of the surface regions. This also shows that substantially all the solvent is removed from the stents after treatment. In this example, the difference in mass before and after treatment is less than 1%.

TABLE 4

Mass Before and After Treatment

| Before shape modification Treatment (mg) | |
|---|---|
| 1 | 5.212 |
| 2 | 5.309 |
| 3 | 5.337 |
| Mean | 5.286 |
| After shape modification Treatment (mg) | |
| 1 | 5.194 |
| 2 | 5.353 |
| 3 | 5.370 |
| 4 | 5.379 |
| 5 | 5.372 |
| Mean | 5.329 |
| % Difference | 0.81% |

Example 2

In some examples, samples were treated by the methods described in Example 1. For these samples, a width of the struts, crowns or links was measured at a narrowest point (core) to find the minimum thickness and at the two widest portions (lip 1 and lip 2) to find two maximum thicknesses. The core was measured at about a midpoint between the location of lip 1 and lip 2. The maximum and minimum thicknesses are reported in Table 5 below and the cross sections are shown in FIGS. 2B and 2C. As shown in Table 5, the thickness varies between the maximum and minimum an amount of about 2% to about 10%.

TABLE 5

Variation in thickness from core to lip

| Sample | Min thickness Core (μm) | Average Lip (μm) | Max thickness Lip 1 (μm) | Max thickness Lip 2 (μm) |
|---|---|---|---|---|
| FIG. 2B | 91 | 98 | 101 | 95 |
| FIG. 2C | 94 | 100 | 99 | 102 |

Example 3

In some examples, the side and abluminal surface regions of at least a portion of the struts, crowns, links and other stent structures can be shaped by solvent dipping while maintaining a substantially flat surface region on the luminal side by inserting a tight mandrel such as a Teflon rod or tube inside the stent. The stent supported tightly on the mandrel is then dipped into a first solvent for about 1 second, 2 seconds, 3 seconds, or up to 20 seconds to cause the solvent to redistribute polymer material. The stent is quickly removed from the solvent when the desired shaping is achieved. Preferably the stent is rinsed in a second solvent to remove materials that are adhering to the stent and to fix the desired shape. FIG. 4 shows a cross sectional shape of a stent which can result from treatment by this process.

Although a tight fitting inner mandrel is described for blocking contact of the first solvent with the luminal side of the stent, other methods of masking the luminal side can also be used to prevent shaping of the luminal surface regions of the stent. Although the luminal surface region of the stent without treatment are described as substantially flat surface regions, it should be understood that the stent if formed from a tube, have surface regions with some slight curvature corresponding to the curvature of the tube. Substantially flat surface regions can occur if the structure is formed from a sheet.

Example 4

Biodegradable polymer stents made from polylactide based polymer were treated with a solvent based stent modification process described above to provide a structure cross section with convex sides and concave abluminal surface region. The modification of the stent surface region shapes was to provide improved tracking and/or push by reducing the force required to track or push the stent mounted on a catheter through a cylindrical body, such as a blood vessel. The reduction of track or push force is achieved by changing the area of surface region contact between the modified stent shape and the vessel. On the abluminal side, the unmodified surface regions on the stent structure can act like ratchet elements as the stent is pushed through a blood vessel, especially one with calcified lesions. This may inhibit tracking through the vessel because the sides may get caught on the walls of the artery.

A test method was developed to characterize a force required for a stent delivery system to cross a lesion located at the apex of a curve in a test fixture with a curved track to simulate a blood vessel.

Figure 16:
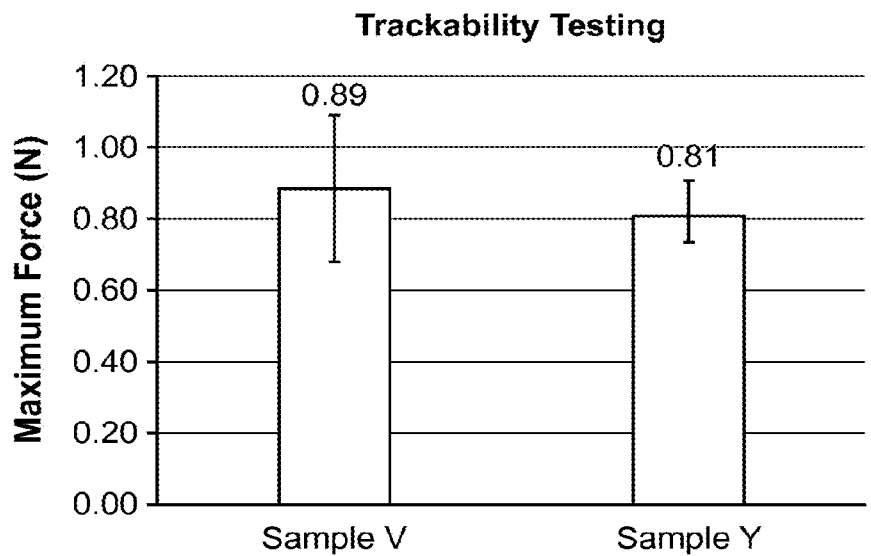
FIG. 16 is a graph of the results of trackability testing.

The fixture is immersed in a water bath maintained at 37° C. and the catheter with a mounted stent is pushed through the fixture. The push force is measured by the Instron attached to the catheter delivery system. The force is measured for units with stents with no modification (sample V) and flat side surface regions and stents with shape modification with convex side structures (sample Y). Test results of FIG. 16 showed a lower push force for the modified stent, indicating better trackability.

Example 5

A bioresorbable stent of 6.0 mm diameter and 60 mm in length is laser cut from a tube of 200 micrometer thickness made from a copolymer of polylactic acid-co-glycolide. The stent is mounted on a smaller mandrel rotating around its longer axis in an enclosed refrigerated chamber and is exposed to surface region modification with dry ice blasting equipment. The sandblasting nozzle is attached to a programmable robotic arm to propel particles along the selected portions of the stent crowns and axial struts. The dry ice blasting nozzle is aimed at the luminal surface regions to compact the treated surface region and create the concave shape of these surface regions. The nozzle of the equipment is aimed at the corners at an angle of about 20 to about 160 degrees with respect to the strut side surface regions to achieve compaction of material at the side surface regions at the corners to provide convex side surface regions without removing significant amounts of material from other parts of the stent. As described herein, the stent can be either tightly mounted on a mandrel or loosely mounting on a mandrel depending on the location of the surface regions to be shaped. The stent can also be positioned inside a tube to shape at least a portion of the surface regions on the luminal surface region of the stent.

Example 6

Figure 17:
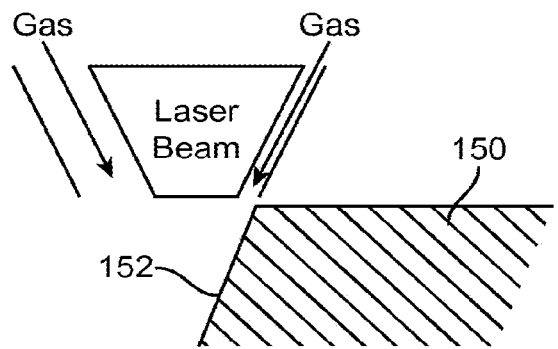
FIG. 17 is a schematic illustration of a laser process for creating convex side surface regions.

A bioresorbable stent of 3.5 mm diameter and 28 mm in length is laser cut from a tube of 100 micrometer thickness made from a polymer of polylactic acid based copolymer. A femtosecond laser is used to create convex and concave surface region crowns on a stent. Because of the ability to ablate with low energy and cut layer by layer, a laser cutting program can be set to ablate about 25 or smaller micrometer width slots. As shown in FIG. 17, a series of overlapping cuts are made from the top surface region to the edge of the stent structure 150 to achieve the desired shape on the crown, axial strut, or link. The stent structure can be cut with off-axis control such that the axis of laser beam and the axis of the assist gas supply nozzle on the laser such as a femtosecond laser is eccentrically oriented. This allows the laser to cut the stent material at an angle 152 rather than straight cut, eventually resulting in the convex cross section side surface regions.

Figure 18:
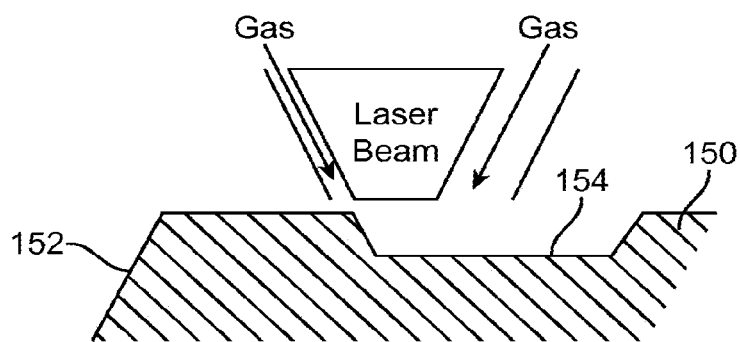
FIG. 18 is a schematic illustration of a laser process for creating concave luminal or abluminal surface regions.

FIG. 18 shows the process of the laser being used to create a concave surface region on the luminal and/or abluminal surface regions by ablating the mid-section of the crown, strut or link 150 in stepwise cuts 154 in the surface region of 150 to eventually create a concavity across substantially the width of the crown, strut or link.

Example 7

A multi-piece metal mold is created with fine stent negative features using wire EDM with the desired shaped strut features having convex sides and concave luminal and abluminal surface regions and held together under high pressure with holding clamps.

The equipment used is specifically designed to mold microparts with small plastic shot sizes for example a 3.5 mm×28 mm stent of 13 cubic millimeters, by utilizing high pressure of up to 100,000 psi and high speed to achieve injection times of around 0.01 seconds, to decrease the dwell time in the mold and minimize thermal degradation of the polymer. The strut width is 200 um and thickness is 200 um.

PLA based polymer is heated in the plasticizing portion of the machine, to the melt temperature of 200° C., and fed into the mold portion of the machine by the injector plunger.

After injection the mold is cooled rapidly to freeze the molten plastic and minimize thermal degradation, and the part removed. The stent structure has a cross section with the convex side surface regions and concave luminal and abluminal surface regions.

Example 8

Biodegradable polymer stents made from polylactide based polymer were measured to determine thickness before and after treatment. The results are shown below in Table 6. The first stent was measured as-cut prior to any treatment. Measurement was performed by taking cross sections of the stent struts and using Micro-Vu at 315× magnification to measure the thickness. The second stent was heat treated for 3 hours at 90 deg. C. The heat treated stent has a slightly concave abluminal surface and convex side surfaces and has a minimum thickness at substantially the center of the abluminal surface which is about 13% greater than the untreated stent. Third and fourth stents were treated with a solvent of 4 parts dichloromethane (methylene chloride) and 6 parts ethanol and rinsed with ethanol. Both stents were then heat treated for 3 hours at 90 deg. C. The stent labeled solvent treatment A was treated for 4 seconds in the solvent mixture and for 3 seconds in the ethanol rinse. The stent labeled solvent treatment B was treated for 2 seconds in the solvent mixture and for 3 seconds in the ethanol rinse. For all stents the treatment of either heat alone or solvent with heat caused an increase in minimum thickness of the struts in the range of about 10% to about 25%. The stents tested were measured before coating with drug matrix.

TABLE 6

Variation in thickness from core to lip

| Sample | Min thickness Core (μm) | Average Lip (μm) | Max thickness Lip 1 (μm) | Max thickness Lip 2 (μm) |
|---|---|---|---|---|
| As Cut | 95.7 | | | |
| Heat treated | 108.2 | | | |
| Solvent treated A | 117.5 | 133.2 | 130.0 | 136.4 |
| Solvent Treated B | 119.3 | 122.0 | 122.3 | 121.7 |

Example 9

Biodegradable polymer stents made from polylactide based polymer were measured to determine thickness before and after treatment. The results are shown below in Table 7. Measurement was performed by taking cross sections of the stent struts and using Micro-Vu at 315× magnification to measure the thickness. The stents were treated with a solvent of 100% tetrahydrofuran (THF) or a combination of 90% TFH and 10% ethanol and rinsed with ethanol. The stent treated with a combination of 90% TFH and 10% ethanol was treated for 3 seconds and rinsed with ethanol for 5 seconds. The stent was then heat treated for 3 hours at 90 deg. C. to remove substantially all of the solvent. The stent treated with a solvent of 100% TFH was treated for 1 second and rinsed with ethanol for 5 seconds. The stent was then heat treated for 3 hours at 90 deg. C. to remove substantially all of the solvent. For each of the stents the treatment caused lips to form along the struts and created a dogbone or bulbous shape of strut cross sections. The stents were measured before coating with drug matrix.

TABLE 7

Variation in thickness from core to lip

| Sample | Min thickness Core (μm) | Average Lip (μm) | Max thickness Lip 1 (μm) | Max thickness Lip 2 (μm) |
|---|---|---|---|---|
| THF/ethanol 90/10 treated | 105.6 | 106.6 | 105.3 | 108.0 |
| THF Treated | 100.1 | 106.5 | 110.0 | 103.0 |

Example 10

An experiment was performed to measure the dimensions of the stent structural elements including the axial length, width and thickness of the elements. The experiment was performed with a stent having elongated axial structural elements to determine the effect of heat treatment or a combination of solvent treatment and heat treatment on the dimensions of the stent structural elements. Measurements were taken of the strut thickness and width at approx. 1-2 mm from each end of the structural element and at a mid link section. The stents were treated as described in Table 8 below and the stents were remeasured. The average percent difference between the treated and untreated stents was calculated.

TABLE 8

| | Heat Treat Ony | | Solvent and Heat Treat Treatment duration | |
|---|---|---|---|---|
| | 3 hr @ 90 C. | 9 hr @ 90 C. | 2 sec solvent treatment Heat 3 hr @ 90 C. | 4 second solvent treatment Heat 3 hr @ 90 C. |
| Length | −3.7% | −3.9% | −5.8% | −7.5% |
| Width | −2.3% | −1.3% | −9.0% | −11.4% |
| Thickness | 0.1% | −0.8% | 12.1% | 22.0% |

Embodiments of the disclosure provide an expandable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions; wherein at least some of the abluminal surface regions are concave across substantially the width of the surface, optionally at least some of the side surface regions are convex across substantially the width of the surface.

Embodiments of the disclosure provide an expandable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions; wherein at least some of the abluminal surface regions have a concave overall surface shape, optionally at least some of the side surface regions have a convex overall surface shape, where the overall shape of a surface region is defined as the shape of a curve fitted to the actual surface by an appropriate fitting procedure such as a least squares fitting procedure.

Embodiments of the disclosure provide an expandable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions; wherein at least some of the side surface regions are convex across substantially the width of the surface and at least some of the abluminal surface regions are flat or concave across substantially the width of the surface.

Embodiments of the disclosure provide an expandable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions; wherein at least some of the side surface regions have a convex overall surface shape and at least some of the abluminal surface regions have a concave or flat overall surface shape, where the overall shape of a surface region is defined as the shape of a curve fitted to the actual surface by an appropriate fitting procedure such as a least squares fitting procedure.

Embodiments of the disclosure provide an expandable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions, the stent structural element having a thickness between the luminal and abluminal surface regions and a width between the side surface regions; wherein for at least some of the stent structural elements the width varies across the thickness.

Embodiments of the disclosure provide an expandable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions, the stent structural element having a thickness between the luminal and abluminal surface regions and a width between the side surface regions; wherein for at least some of the stent structural elements the width varies across the thickness such that the width increases in a direction away from the luminal and abluminal surface regions.

Embodiments of the disclosure provide an biodegradable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions, the stent structural element having a thickness between the luminal and abluminal surface regions and a width between the side surface regions; wherein for at least some of the stent structural elements the width varies across the thickness such that a minimum width is at the luminal and abluminal surface regions.

Embodiments of the disclosure provide an expandable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions, the stent structural element having a thickness between the luminal and abluminal surface regions and a width between the side surface regions; wherein for at least some of the stent structural elements the thickness varies across the width.

Embodiments of the disclosure provide an expandable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions, the stent structural element having a thickness between the luminal and abluminal surface regions and a width between the side surface regions; wherein for at least some of the stent structural elements the thickness varies across the width such that thickness decreases in a direction away from the side surface regions.

Embodiments of the disclosure provide an expandable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions, the stent structural element having a thickness between the luminal and abluminal surface regions and a width between the side surface regions; wherein for at least some of the stent structural elements the width varies across the thickness such that a minimum width is at the luminal and abluminal surface regions.

Embodiments of the disclosure provide an expandable stent prosthesis that preferably is biodegradable.

In embodiments of the disclosure, the tubular expandable stent prosthesis body may comprise a non-braided tubular body. For example, the tubular expandable stent prosthesis body may comprise a patterned tubular body. The patterned tubular body may be patterned by cutting or etching, for example by use of a laser. As examples the tube may be formed by extrusion, spraying, dipping or molding. The tubular expandable stent prosthesis body may be formed as a tube or from a flat sheet which may be patterned before or after being formed into a cylinder to form the tubular body. Any of these tubular bodies may be pre-formed with the above-described surface shapes or may be modified after formation to provide the above-described surface shapes. Where a tubular body is formed from a flat sheet then the flat sheet may be pre-formed with the above-described surface shapes or may be modified after formation to provide the above-described surface shapes.

In embodiments, concave abluminal surface regions can provide benefits in drug coating and in drug delivery and benefits in embedding the stent prosthesis into the vessel wall. In embodiments, a reduction of tracking or push force required to track or push a stent mounted on a catheter through a cylindrical body, such as a blood vessel, may be achieved because of the change of the area of contact between the stent prosthesis and the vessel wall resulting from the surface region shaping. In embodiments, a lower push force may be required for stent prostheses with convex side surface regions than for stent prostheses with flat side surface regions, providing better trackability.

In some examples, the stent prosthesis is formed as a tubular body by extrusion, dipping, molding or printing and then patterned into a stent. In some examples the stent prosthesis is formed as a sheet, wherein the sheet is rolled to form a tubular body wherein the sheet is patterned into a stent before or after forming into a tubular body. The rolled sheet edges are affixed or joined together to form a tubular body by treatment such as using heating, chemical bonding, ultrasound bonding, laser bonding or other means. In some examples the stent prosthesis is formed as a sheet, wherein the sheet is patterned prior to rolling the patterned stent into a tubular patterned stent using the methods described previously. In some examples, the stent prosthesis is formed as a tubular pattered body, wherein the patterning and forming of the tubular body take place concurrently, such as the example of 3-D printing. In some examples, the stent prosthesis is formed as a three dimensional structure or body and then patterned into a stent. In some examples, the stent prosthesis is formed as a substantially tubular body and then patterned into a stent. In any of the above examples the structural elements are formed with the desired shape or treated to form the desired shape as described herein.

Example 11

A PLLA based polymeric tubular material was formed and patterned using a laser into a stent. The stent was then heat treated at 90° C. for 3 hours. The stent was coated with a drug/polymer matrix, crimped onto a catheter while being heated at a temperature at about 45° C., packaged, and sterilized. A control group was also made using the same steps and parameters without heat treating the stent after patterning and before crimping (without heating the stent to 90° C. for 3 hours). The units were then tested for radial strength (iris compression test). The resulting radial strength increased for the heat treated group.

TABLE 9

| Test Arm (n = 3) | Radial Strength (psi) |
| --- | --- |
| 3.0 × 14 mm Control | 15.6 |
| 3.0 × 14 mm heat treatment | 18.1 |

TABLE 9-continued

| Test Arm (n = 3) | Radial Strength (psi) |
|---|---|
| post patterning and before crimping | |

Example 12

A PLLA based polymeric tubular material is formed and patterned using a laser into a stent. The stent is then treated by exposing it to a solvent mixture of DCM and Ethanol for 0.1-1.5 second. The stent is then exposed to ethanol for 1-5 seconds. The scaffold is then heat treated at 90° C. for 3 hours. The stent is coated with a drug/polymer matrix, crimped onto a catheter while being heated at a temperature below 55° C., packaged, and sterilized. The biodegradable stent is deployed from the crimped configuration to the deployed expanded configuration wherein the stent in the deployed configuration has a strength sufficient to support a body lumen.

Throughout the specification, including the claims, where the context permits, the term "comprising" and variants thereof such as "comprises" or "comprising" are to be interpreted as including the stated integer or integers without necessarily excluding any other integers.

The Disclosure of this Application Also Includes the Following Numbered Clauses:

1. An expandable biodegradable stent prosthesis comprising:
a tubular expandable stent prosthesis body comprising a biodegradable material, said expandable stent prosthesis body comprising stent structural elements having luminal and abluminal surface regions; wherein at least some of the abluminal surface regions have a concave shape across substantially the width of said surface regions.

In embodiments of the disclosure, a concave abluminal surface region minimizes or at least reduces the possibility of slippage of the stent prosthesis when expanded to a deployed configuration, such that the stent structural elements hug the vessel wall or the plaque area better.

In embodiments of the disclosure, concave abluminal surface regions may prevent or reduce rotating of stent structural elements during crimping and/or during expansion.

In embodiments of the disclosure, concave luminal and/or abluminal surface regions may also provide improved directionality of drug delivery to the lumen or vessel wall.

2. The expandable biodegradable stent prosthesis of clause 1, wherein said stent structural elements each have side surface regions extending between the luminal and abluminal surface regions; and wherein at least some of the side surface regions have a convex shape across substantially the thickness of said stent structural elements.

3. The expandable biodegradable stent prosthesis of clause 1 or 2, wherein substantially all of the side surface regions have a convex shape across substantially the thickness of said side surface regions.

In embodiments of the disclosure, concave abluminal surface regions and convex side surface regions, may increase the surface region area along the length of stent prosthesis, while reducing or maintaining surface region porosity of the luminal and side surface regions.

4. The expandable biodegradable stent prosthesis of clause 1, wherein said stent structural elements each have side surface regions extending between the luminal and abluminal surface regions; and wherein at least some of the side surface regions have a concave shape across substantially the thickness of said stent structural elements.

5. The expandable biodegradable stent prosthesis of clause 4, wherein substantially all of the side surface regions have a concave shape across substantially the thickness of said side surface regions.

6. The expandable biodegradable stent prosthesis of any of clauses 1 to 5, wherein substantially all of the abluminal surface regions have a concave shape across substantially their width.

7. The expandable biodegradable stent prosthesis of any of clauses 1 to 6, wherein at least some of the luminal surface regions have a concave shape across substantially the width of said surface regions.

8. The expandable biodegradable stent prosthesis of clause 7, wherein substantially all of the luminal surface regions have a concave shape across substantially their width.

9. An expandable biodegradable stent prosthesis comprising:
a tubular expandable stent prosthesis body, said expandable stent prosthesis body comprising stent structural elements each having a surface with a luminal surface region, an abluminal surface region, coupling portions coupling the abluminal and luminal surface regions, and a thickness between said luminal and abluminal surface regions; wherein at least a part of at least some of the coupling portions is bulbous.

10. The expandable stent prosthesis of clause 9, wherein the abluminal surface region is flat.

11. The expandable stent prosthesis of clause 9, wherein the abluminal surface region is concave.

12. The expandable stent prosthesis of clause 9, 10 or 11, wherein the luminal surface region is flat.

13. The expandable stent prosthesis of clause 9, 10 or 11, wherein the luminal surface region is flat.

14. The expandable stent prosthesis of any of clauses 9 to 13, wherein the surface has two side surface regions each coupling the abluminal and luminal surface regions and the side surface regions comprise bulbous coupling portions.

15. The expandable stent prosthesis of any of clauses 9 to 13, wherein the surface has two side surface regions each coupling the abluminal and luminal surface regions and there are two bulbous coupling portions each defined by the abluminal surface region and a respective one of the side surface regions.

16. The expandable stent prosthesis of any of clauses 9 to 13, wherein the surface has two side surface regions each coupling the abluminal and luminal surface regions and there are two bulbous coupling portions each defined by the luminal surface region and a respective one of the side surface regions.

17. The expandable stent prosthesis of any of clauses 9 to 13, wherein the surface has two side surface regions each coupling the abluminal and luminal surface regions and there are four bulbous coupling portions two defined by the luminal surface region and the side surface regions and two defined by the luminal surface region and the side surface regions.

18. The expandable stent prosthesis of clause 9, wherein the surface has a dogbone or dumbbell shape with two opposed end bulbous coupling portions.

19. The expandable stent prosthesis of clause 9, wherein the surface has two side surface regions each coupling the abluminal and luminal surface regions and there are two bulbous coupling portions each defined by the abluminal surface region and a respective one of the side surface regions, wherein the abluminal surface region has a concave portion.

20. The expandable stent prosthesis of clause 9, wherein the surface has two side surface regions each coupling the abluminal and luminal surface regions and there are two bulbous coupling portions each defined by the abluminal surface region and a respective one of the side surface regions, wherein the abluminal surface region has a concave portion, the side regions are flat and the luminal surface region is flat or convex.

21. The expandable prosthesis of any of clauses 2 to 8, wherein the stent structural elements each have two side surface regions extending between the luminal and abluminal surface regions.

22. The expandable stent prosthesis of any of clauses 1 to 21, wherein the stent structural elements comprise struts and crowns.

23. The expandable stent prosthesis of clause 22, wherein the stent prosthesis body comprises expandable rings, each ring is composed of struts joined by crowns, and each ring is connected to an adjacent ring by at least one link.

24. The expandable stent prosthesis of any of clauses 1 to 23 wherein said surface region shape is formed by treating the expandable stent prosthesis.

25. The expandable stent prosthesis of clause 24, wherein the treatment includes shaping by application of a solvent by at least one of dipping, spraying, or contact with a solvent vapor.

26. The expandable stent prosthesis of clause 24 or 25, wherein the treatment includes shaping by tumbling, agitating, deburring, scraping, media blasting, laser treatment or heat treatment.

27. The expandable stent prosthesis of clause 24, 25 or 26, wherein a weight of the expandable stent prosthesis after treatment is substantially the same as before treatment.

28. The expandable stent prosthesis of any of clauses 24 to 27, wherein the treatment does not significantly dissolve the polymeric material from which said prosthesis is formed.

29. The expandable stent prosthesis of any of clauses 24 to 28 wherein the treatment shifts material from a surface region of a said stent structural element to an immediately adjacent surface region of a said stent structural element without a substantial change in body weight of said expandable stent prosthesis.

30. The expandable stent prosthesis of any of clauses 24 to 29, said body has been treated to adjust a thickness of stent structural elements from a first thickness before treatment to a second thickness after treatment, wherein the second thickness is greater than the first thickness.

31. The expandable stent prosthesis of any of clauses 24 to 30, wherein the treatment causes a thickness of stent structural elements between the luminal and abluminal surface regions to increase while a width of the stent structural elements between the side surface regions remains substantially the same.

32. The expandable stent prosthesis of any of clauses 24 to 31, wherein the treatment causes a thickness of stent structural elements between the luminal and abluminal surface regions to increase while decreasing a minimum width of the stent structural elements between the side surface regions by redistributing the biodegradable material.

33. The expandable stent prosthesis of any of clauses 24 to 32, wherein the treatment comprises exposing the expandable stent prosthesis to a solvent for a predetermined period of time.

34. The expandable stent prosthesis of any of clauses 1 to 33, wherein the expandable stent prosthesis body has been patterned from a tube by a laser.

35. The expandable stent prosthesis of any of clauses 1 to 34, further comprising a coating formed over at least some portions of the expandable stent prosthesis body.

36. The expandable stent prosthesis of clause 35, wherein surface region shape is retained after coating.

37. The expandable stent prosthesis of clause 35 or 36 wherein the coating comprises a drug.

38. The expandable stent prosthesis of any of clauses 1 to 37, wherein the biodegradable material comprises biodegradable polymeric material.

39. The expandable stent prosthesis of clause 38, wherein the biodegradable polymeric material comprises at least one material selected from the group consisting of lactides, poly-DL-Lactide, polylactide-co-gycolide, polylactide-co-polycaprolactone, poly (L-lactide-co-trimethylene carbonate), polytrimethylene carbonate, polyhydroxybutyrate, polyhydroxyvalerate, poly orthoesters, poly anhydrides, polylactide, polyglycolides, polycaprolactone, polyiminocarbonates and copolymers thereof.

40. The expandable stent prosthesis of clause 38 or 39, wherein the biodegradable polymeric material of said expandable stent prosthesis body comprises at least two biodegradable polymers.

41. The expandable prosthesis of clause 38, 39 or 40, wherein the biodegradable polymeric material has an elastic modulus of at least 0.35 GPa.

42. The expandable stent prosthesis of clause 38 or 39, wherein the biodegradable polymeric material comprises one or more of polymers and copolymers.

43. The expandable stent prosthesis of any of clauses 38 to 42, wherein the biodegradable polymeric material has a molecular weight ranging from 100 KDa to 1000 KDa.

44. The expandable stent prosthesis of any of clauses 1 to 43, wherein the prosthesis is balloon expandable.

45. An expandable biodegradable stent prosthesis comprising:
a tubular expandable stent prosthesis body, which may comprise a biodegradable material, such as a biodegradable polymeric material, wherein the stent comprises a plurality of stent structural elements, wherein said structural elements each have a luminal surface region, an abluminal surface region, and two side surface regions extending between the luminal and abluminal surface regions; and wherein at least some of the side surface regions have a convex shape.

In some examples, the surface region area over which the tensile and compressive stresses are distributed during bending of a stent structural element is increased due to the convex side surface regions and this leads to increased radial strength of the stent prosthesis.

In some examples, convex side surface regions enable greater contact than square or rectangular flat surface regions between balloon material of the delivery system and the stent prosthesis. For example, in a process of crimping the stent prosthesis onto a balloon, there may be an increased surface region area of contact between the stent structural element with convex side regions and a flap of the balloon than with the flat side surface regions which may enable improved stent retention on a balloon catheter in a crimped configuration. Convex side surface regions can also improve crimping of the stent prosthesis because convex side surface regions are more resistant to overlapping or twisting which may occur with flat rectangular surface regions during expansion and/or during crimping.

In some examples, convex side surface regions can also improve flexibility of the stent prosthesis. For example, a stent structural element stent with convex side surface regions may be able to bend in more directions than to a stent structural element with flat surface regions providing a more flexible and deliverable stent prosthesis.

In some examples, when stent structural elements are coated with a drug for delivery to a lumen, convex side surface regions can provide for a more uniform drug coating and thus can release drug from a substantially more uniform surface region than a square or rectangular strut.

46. The expandable biodegradable stent prosthesis of clause 45, wherein at least some of the abluminal surface regions have a concave shape or are flat across substantially the width of said abluminal surface regions.

47. The expandable biodegradable stent prosthesis of clause 45 or 46, wherein substantially all of the side surface regions have a convex shape across substantially the thickness of said side surface regions.

48. The expandable biodegradable stent prosthesis of clause 45, 46 or 47, wherein said prosthesis has been treated by contact with a solvent to redistribute said biodegradable material to provide said surface region shape.

49. The expandable biodegradable stent prosthesis of clause 45, 46, 47 or 48, wherein said prosthesis has been treated by contact with a solvent to redistribute said biodegradable material to provide an increased thickness of said side surface regions and decreased width of said abluminal and luminal surface regions.

50. The expandable biodegradable stent prosthesis of any of clauses 45 to 49, wherein substantially all of the abluminal surface regions have a concave shape across substantially their width.

51. The expandable biodegradable stent prosthesis of any of clauses 45 to 50, wherein at least some of the luminal surface regions have a concave shape across substantially the width of said surface regions.

52. The expandable biodegradable stent prosthesis of any of clauses 45 to 50, wherein at least some of the luminal surface regions are flat across substantially the width of said surface regions.

53. The expandable biodegradable stent prosthesis of any of clauses 45 to 50, wherein at least some of the luminal surface regions have a concave shape across substantially the width of said surface regions.

54. The expandable stent prosthesis of any of clauses 45 to 53, wherein the stent structural elements comprise struts and crowns.

55. The expandable stent prosthesis of clause 54, wherein the stent prosthesis body comprises expandable rings, each ring is composed of struts joined by crowns, and each ring is connected to an adjacent ring by at least one link.

56. The expandable stent prosthesis of any of clauses 45 to 55 wherein said surface region shape is formed by treating the expandable stent prosthesis.

57. The expandable stent prosthesis of clause 56, wherein the treatment includes shaping by application of a solvent by at least one of dipping, spraying, or contact with a solvent vapor.

58. The expandable stent prosthesis of clause 46 or 47, wherein the treatment includes shaping by tumbling, agitating, deburring, scraping, media blasting, laser treatment or heat treatment.

59. The expandable stent prosthesis of clause 56, 57 or 58, wherein a weight of the expandable stent prosthesis after treatment is substantially the same as before treatment.

60. The expandable stent prosthesis of any of clauses 45 to 59, wherein the treatment does not significantly dissolve the polymeric material from which said prosthesis is formed.

61. The expandable stent prosthesis of any of clauses 45 to 60 wherein the treatment shifts material from a surface region of a said stent structural element to an immediately adjacent surface region of a said stent structural element without a substantial change in body weight of said expandable stent prosthesis.

62. The expandable stent prosthesis of any of clauses 45 to 61, said body has been treated to adjust a thickness of stent structural elements from a first thickness before treatment to a second thickness after treatment, wherein the second thickness is greater than the first thickness.

63. The expandable stent prosthesis of any of clauses 45 to 62, wherein the treatment causes a thickness of stent structural elements between the luminal and abluminal surface regions to increase while a width of the stent structural elements between the side surface regions remains substantially the same.

64. The expandable stent prosthesis of any of clauses 45 to 62, wherein the treatment causes a thickness of stent structural elements between the luminal and abluminal surface regions to increase while decreasing a minimum width of the stent structural elements between the side surface regions by redistributing the biodegradable material.

65. The expandable stent prosthesis of any of clauses 45 to 64, wherein the treatment comprises exposing the expandable stent prosthesis to a solvent for a predetermined period of time.

66. The expandable stent prosthesis of any of clauses 45 to 65, wherein the expandable stent prosthesis body has been patterned from a tube by a laser.

67. The expandable stent prosthesis of any of clauses 45 to 66, further comprising a coating formed over at least some portions of the expandable stent prosthesis body.

68. The expandable stent prosthesis of clause 67, wherein surface region shape is retained after coating.

69. The expandable stent prosthesis of clause 67 or 68 wherein the coating comprises a drug.

70. The expandable stent prosthesis of any of clauses 45 to 69, wherein the biodegradable material comprises biodegradable polymeric material.

71. The expandable stent prosthesis of clause 70, wherein the biodegradable polymeric material comprises at least one material selected from the group consisting of lactides, poly-DL-Lactide, polylactide-co-gycolide, polylactide-co-polycaprolactone, poly (L-lactide-co-trimethylene carbonate), polytrimethylene carbonate, polyhydroxybutyrate, polyhydroxyvalerate, poly orthoesters, poly anhydrides, polylactide, polyglycolides, polycaprolactone, polyiminocarbonates and copolymers thereof.

72. The expandable stent prosthesis of clause 70 or 71, wherein the biodegradable polymeric material of said expandable stent prosthesis body comprises at least two biodegradable polymers.

73. The expandable prosthesis of clause 70, 71 or 72, wherein the biodegradable polymeric material has an elastic modulus of at least 0.35 GPa.

74. The expandable stent prosthesis of clause 70 or 73, wherein the biodegradable polymeric material comprises one or more of polymers and copolymers.

75. The expandable stent prosthesis of any of clauses 70 to 74, wherein the biodegradable polymeric material has a molecular weight ranging from 100 KDa to 1000 KDa.

76. The expandable stent prosthesis of any of clauses 45 to 75, wherein the prosthesis is balloon expandable.

77. An expandable biodegradable stent prosthesis comprising:
a tubular expandable stent prosthesis body comprising a biodegradable polymeric material, said expandable stent prosthesis body comprising stent structural elements each having a luminal surface region and an abluminal surface region and a thickness between said luminal and abluminal surfaces; wherein a side surface region extending between the abluminal surface region and the luminal surface region of at least some structural elements is bulbous.

78. The expandable prosthesis of clause 77, wherein two side surface regions extending between the luminal and abluminal surface regions of at least some stent structural elements are bulbous.

79. The expandable stent prosthesis of clause 78, wherein at least some of the abluminal surface regions are concave between the two bulbous side surface regions.

80. The expandable prosthesis of clause 77, 78 or 79, wherein a width of the stent structural elements between the side surface regions is greater at about the mid-point between said abluminal and luminal surface regions.

81. The expandable stent prosthesis of any of clauses 77 to 80, wherein the stent structural elements comprise expandable rings, each ring comprising struts joined by crowns, and each ring is connected to an adjacent ring by at least one link.

82. The expandable stent prosthesis of any of clauses 77 to 81, wherein the stent structural elements comprise struts joined by crowns.

83. The expandable prosthesis of any of clauses 77 to 82, wherein at least some of said stent structural elements are oval in cross section.

84. The expandable prosthesis of any of clauses 77 to 83, wherein the biodegradable polymeric material of said expandable stent prosthesis body comprises at least two biodegradable polymers.

85. The expandable prosthesis of any of clauses 77 to 84, further comprising at least some of the abluminal surface regions being concave or flat across substantially the width of said surface regions.

86. The expandable prosthesis of any of clauses 77 to 85, wherein the expandable stent prosthesis body has been patterned from a tube by a laser.

87. The expandable prosthesis of clause 86, wherein the expandable prosthesis body is formed from a substantially continuous body free from discontinuities before patterning.

88. The expandable prosthesis of any of clauses 77 to 87, wherein the stent structural elements have been treated to form the bulbous region.

89. The expandable prosthesis of clause 85, wherein the expandable stent prosthesis body has been patterned from a tube by a laser and wherein the stent structural elements have been treated to form said concave or flat abluminal surface regions and bulbous side surface regions.

90. The expandable stent prosthesis of clause 88 or 89, wherein the treatment includes shaping by application of a solvent by at least one of dipping, spraying, or contact with a solvent vapor.

91. The expandable stent prosthesis of clause 88 or 89, wherein the treatment includes shaping by tumbling, agitating, deburring, scraping, media blasting, laser treatment or heat treatment.

92. The expandable stent prosthesis of any of clauses 77 to 91, further comprising a coating of at least one drug formed over at least some portions of the expandable stent prosthesis body.

93. The expandable stent prosthesis of any of clauses 77 to 92, further comprising a coating over the expandable stent prosthesis body, said bulbous regions of said stent structural elements remaining substantially bulbous after coating.

94. The expandable stent prosthesis of clause 88 or 89 or any clause dependent upon clause 88 or 89, wherein a weight of the expandable stent prosthesis after treatment is substantially the same as before treatment.

95. The expandable prosthesis of any of clauses 77 to 94, wherein the biodegradable polymeric material has an elastic modulus of at least 0.35 GPa.

96. The expandable stent prosthesis any of clauses 77 to 95, wherein the biodegradable polymeric material comprises one or more of polymers and copolymers.

97. The expandable stent prosthesis of any of clauses 77 to 96, wherein the prosthesis is expandable from a crimped diameter to a deployed larger diameter at body temperature.

98. The expandable stent prosthesis of clause 81 or any clause dependent thereon, wherein the prosthesis is expandable from a crimped diameter to a deployed diameter at body temperature without substantial rotation of at least one of the struts, crowns or links about their axis.

99. The expandable stent prosthesis of any of clauses 77 to 98, wherein the biodegradable polymeric material comprises at least one material selected from the group consisting of lactides, poly-DL-Lactide, polylactide-co-gycolide, polylactide-co-polycaprolactone, poly (L-lactide-co-trimethylene carbonate), polytrimethylene carbonate, polyhydroxybutyrate, polyhydroxyvalerate, poly orthoesters, poly anhydrides, polylactide, polyglycolides, polycaprolactone, polyiminocarbonates and copolymers thereof.

100. The expandable stent prosthesis of any of clauses 77 to 99, wherein the prosthesis is balloon expandable.

101. The expandable stent prosthesis of clause 88 or 89 or any clause dependent upon clause 88 or 89, wherein the treatment does not dissolve the polymeric material from which said prosthesis is formed.

102. The expandable stent prosthesis of clause 82 or any clause dependent thereon, wherein said prosthesis has been treated to shift material from the surface region of some struts and/or crowns to an immediately adjacent surface region of said strut or crown without a substantial change in body weight of said expandable stent prosthesis.

103. The expandable stent prosthesis of any of clauses 77 to 102, wherein biodegradable polymeric material has a molecular weight ranging from 100 KDa to 1000 KDa.

104. The expandable stent prosthesis of any of clauses 77 to 103, said body has been treated to adjust a thickness of the plurality of stent structural elements from a first thickness before treatment to a second thickness after treatment, wherein the second thickness is greater than the first thickness.

105. The expandable stent prosthesis of clause 80 or any clause dependent thereon, wherein said body has been treated to cause a thickness of a plurality of stent structural elements between the luminal and abluminal surface regions to increase while a width of the stent structural elements between the side surface regions remains substantially the same.

106. The expandable stent of clause 88 or 89 or any clause dependent upon clause 88 or 89, wherein the treatment comprises exposing the expandable prosthesis to a solvent for a predetermined period of time provide substantially at least some bulbous side surface regions and at least some concave or flat abluminal surface regions of said stent structural elements.

107. The expandable stent prosthesis of clause 88 or 89 or any clause dependent upon clause 88 or 89, wherein the treatment causes a thickness of the plurality of stent structural elements between the luminal and abluminal surface regions to increase while decreasing a minimum width of the stent structural elements between the side surface regions by redistributing the polymeric material.

108. The expandable stent prosthesis of any of clauses 77 to 107, wherein said prosthesis has been treated by contact with a solvent to redistribute said polymeric material to provide an increased thickness of said stent structural elements and a decreased width of said stent structural elements.

109. An expandable biodegradable stent prosthesis comprising:
an expandable stent prosthesis body comprising a biodegradable polymeric material, wherein the stent comprises a plurality of stent structural elements, wherein said stent structural elements each have a luminal surface region, an abluminal surface region, and two side surface regions extending between the luminal and abluminal surface regions; and wherein at least some of the stent structural elements have a bulbous shape coupling said abluminal and said luminal surface regions to form a dogbone shaped cross section.

110. The expandable stent prosthesis of clause 109, wherein some of said bulbous shaped regions have a convex shape and have a flat portion.

111. The expandable biodegradable stent prosthesis of clause 109 or 110, wherein said prosthesis has been treated by contact with a solvent to redistribute said polymeric material to provide said shapes.

112. The expandable biodegradable stent prosthesis of clause 109 or 110, wherein said prosthesis has been treated by contact with a solvent to redistribute said polymeric material to provide an increased thickness of said side surface regions and decreased width of said abluminal and luminal surface regions.

113. The expandable stent prosthesis of any of clauses 77 to 112, wherein said stent prosthesis further comprises radiopaque markers.

114. The expandable stent prosthesis of any of clauses 77 to 113, wherein the stent further comprises metallic material.

115. An expandable biodegradable stent prosthesis comprising:
a tubular expandable stent prosthesis body comprising a biodegradable polymeric material, said expandable stent prosthesis body comprising stent structural elements each having a luminal surface and an abluminal surface and a thickness between said luminal and abluminal surfaces; wherein the thickness varies across the width of at least some of the structural elements.

116. The expandable stent prosthesis of clause 115, wherein said thickness of at least some stent structural elements is greater at an edge of said abluminal surface region than the thickness near the middle of said abluminal surface region of said structural elements.

117. The expandable stent prosthesis of clause 115, wherein said thickness of at least some stent structural elements is smaller at an edge of said abluminal surface region than the thickness near the middle of said abluminal surface region of said structural elements.

118. The expandable prosthesis of clause 115, 116 or 117, wherein the stent structural elements have two side surface regions extending between the luminal and abluminal surface regions, wherein at least some of the side surface regions are convex.

119. The expandable prosthesis of clause 118, wherein a width of the stent structural elements between the side surface regions also varies across the thickness of at least some stent structural elements.

120. The expandable stent prosthesis of any preceding clause, wherein at least some abluminal surface regions and/or at least some luminal surface regions have a lip.

121. The expandable stent prosthesis of clause 120, wherein a point on said lip has a thickness that is different from the adjacent abluminal surface region, for example wherein the difference in thickness ranges between 2 micrometer and 10 micrometer.

122. The expandable stent prosthesis of any preceding clause, wherein concave luminal and/or abluminal surface regions join convex side surface regions at a lip which extends along at least some of the structural elements.

123. The expandable stent prosthesis of clause 122, wherein the lip forms a thickest point of the structural element cross section.

124. The expandable stent prosthesis of any of clauses 120 to 123, wherein the lip is in the shape of a wave where the surface regions meet.

125. The expandable stent prosthesis of any of clauses 120 to 124, wherein the lips extend continuously along a strut and a connected crown of the expandable stent prosthesis.

126. The expandable stent prosthesis of any of clauses 120 to 125, wherein the stent prosthesis cross section has concave luminal and/or abluminal surface regions and convex side surface regions which form a continuous curve across these surface, for example, the convex side surfaces provide a continuous curve in the form of an arc which extends between abluminal and luminal lips.

127. The expandable stent prosthesis of any of clauses 120 to 126, wherein at least some abluminal surface regions and at least some luminal surface regions have a lip and a thickness between an abluminal lip and a luminal lip forms a thickest part of the cross section, while a thickness at a core or substantially a midpoint between the abluminal lip and the luminal lip or between the abluminal lips forms a thinnest part of the cross section, for example a difference between the thickest and thinnest portions of the cross section may be at least 2%, at least 5%, at least 10%, at least 20%, or at least 30% of the maximum thickness.

128. The expandable stent prosthesis of any of the preceding clauses, wherein upon application of a coating an outer surface area of the structural elements is not substantially changed or is not changed by more than 5%, by more than 10% or by more than 20%.

129. The expandable stent prosthesis of any of the preceding clauses, wherein upon application of the coating a cross sectional area of the structural elements in not substantially changed or is not changed by more than 5%, by more than 10% or by more than 20%.

130. A biodegradable stent prosthesis comprising a polymeric material wherein the stent prosthesis has been formed from a tubular body having an initial diameter using extrusion, spraying, dipping, molding, or printing, and wherein the tubular body has been patterned into a stent with a patterned diameter, said stent comprising structural elements which have abluminal, luminal and side surface regions, said structural elements comprising struts joined by crowns wherein said struts and crowns have an initial thickness and an initial width, wherein said structural elements have been treated to change the thickness or the width of at least some structural elements, said stent prosthesis being expandable from a crimped configuration to an expanded larger configuration and having sufficient strength to support a body lumen, said stent prosthesis is expandable to the larger configuration without fracture.

131. The biodegradable stent prosthesis of clause 130, wherein the tubular body has been exposed to an additional treatment before patterning wherein the additional treatment comprises at least one or more of heating, cooling, pressurizing the polymeric material, or chemically treating the polymeric material.

132. The biodegradable stent prosthesis of clause 130 and 131, wherein the treatment is after patterning and comprises one or more of chemical treatment, heating, mechanical shaping, laser shaping or blasting.

133. The biodegradable stent prosthesis of any of clauses 130 to 132, wherein the polymeric material has been treated during patterning wherein the treatment comprises at least one or more of heating, solvent treatment, mechanical shaping, laser shaping or blasting.

134. The biodegradable stent prosthesis of any of clauses 130 to 133, wherein the treatment to change the thickness or width is after patterning.

135. The biodegradable stent prosthesis of any of clauses 130 to 134, wherein the thickness is larger after treatment.

136. The biodegradable stent prosthesis of any of clauses 130 to 135, wherein the thickness is increased at least in one region across the width of said structural elements.

137. The biodegradable stent prosthesis of any of clauses 130 to 136, wherein the thickness is increased at least in at least two regions across the width of said structural elements.

138. The biodegradable stent prosthesis of any of clauses 130 to 137, wherein the thickness increase is variable across the width of said structural elements.

139. The biodegradable stent prosthesis of any of clauses 130 to 138, wherein the thickness of said structural elements is greater adjacent the sides of said structural elements.

140. The biodegradable stent prosthesis of any of clauses 130 to 139, wherein the thickness is smallest near a midpoint between the sides of said structural elements.

141. The biodegradable stent prosthesis of any of clauses 130 to 140, wherein the thickness changes after treatment by from 2 micrometer to 35 micrometer, preferably between 3 micrometer and 20 micrometer, most preferably between 4 micrometer and 10 micrometer.

142. The biodegradable stent prosthesis of any of clauses 130 to 141, wherein the structural elements width changes after treatment.

143. The biodegradable stent prosthesis of any of clauses 130 to 142, wherein the width of said structural elements becomes smaller after treatment.

144. The biodegradable stent prosthesis of any of clauses 130 to 143, wherein the width changes across said structural elements.

145. The biodegradable stent prosthesis of any of clauses 130 to 144, wherein the width of said structural elements is greatest at about the center of said structural elements.

146. The biodegradable stent prosthesis of any of clauses 130 to 145, wherein the width changes after treatment by from 2 micrometer to 35 micrometer, preferably between 3 micrometer and 20 micrometer, most preferably between 4 micrometer and 10 micrometer.

147. The biodegradable stent prosthesis of any of clauses 130 to 146, wherein the structural elements have an initial shape, wherein the treatment changes the shape of said structural elements.

148. The biodegradable stent prosthesis of any of clauses 130 to 147, wherein the treatment changes the shape of said structural elements by forming a protruding bulbous region between the luminal and abluminal surface regions.

149. The biodegradable stent prosthesis of any of clauses 130 to 148, wherein the treatment changes the shape of said structural elements to form a convex shape across the thickness of said structural elements.

150. The biodegradable stent prosthesis of any of clauses 130 to 149, wherein the treatment changes the shape of said structural elements abluminal surface to form a substantially concave shape.

151. The biodegradable stent prosthesis of any of clauses 130 to 150, wherein the initial and patterned diameters are the same.

152. The biodegradable stent prosthesis of any of clauses 130 to 151, wherein the tubular body is formed at an initial diameter, wherein the treatment of said structural elements does not substantially change the diameter of said tubular body.

153. The biodegradable stent prosthesis of any of clauses 130 to 152, wherein the treatment of said structural elements reduces the initial formed diameter to a smaller diameter.

154. The biodegradable stent prosthesis of any of clauses 130 to 153, wherein the treatment reduces the patterned diameter to a smaller diameter.

155. The biodegradable stent prosthesis of any of clauses 130 to 154, wherein the treatment of said structural elements to change the width or thickness reduces an inner diameter of the prosthesis to a smaller diameter after treatment.

156. The biodegradable stent prosthesis of any of clauses 130 to 155, wherein an inner diameter of the prosthesis after treatment is reduced by between 0.05 mm to 3 mm, preferably between 0.1 mm to 2 mm, most preferably between 0.1 mm and 1 mm.

157. The biodegradable stent prosthesis of any of clauses 130 to 156, wherein the treatment does not substantially change angles between said struts.

158. The biodegradable stent prosthesis of any of clauses 130 to 156, wherein the treatment changes at least some angles between said structural elements.

159. The biodegradable stent prosthesis of any of clauses 130 to 156, wherein angles between said struts changes after treatment.

160. The biodegradable stent prosthesis of any of clauses 130 to 156, wherein the angles between said struts become smaller in an amount ranging from 1 degree to 75 degrees, preferably between 2 degrees 50 degrees, most preferably between 2 degrees and 10 degrees.

161. The biodegradable stent prosthesis of any of clauses 130 to 156, wherein the angles between said struts become larger after treatment, in the range of 1 degree to 75 degrees, preferably in the range of 2 degrees to 50 degrees, most preferably in the range of 2 degrees to 25 degrees.

162. The biodegradable stent prosthesis of any of clauses 130 to 161, wherein the treatment shrinks the length of the stent prosthesis after treatment.

163. The biodegradable stent prosthesis of any of clauses 130 to 162, wherein the length shrinkage ranges between 0.1 mm and 5 mm, preferably between 1 mm and 2 mm.

164. The biodegradable stent prosthesis of any of clauses 130 to 163, wherein the length shrinkage ranges between 1% and 20%

165. The biodegradable stent prosthesis of any of clauses 130 to 164, where the treatment comprises chemical treatment of said patterned stent with at least one solvent.

166. The biodegradable stent prosthesis of any of clauses 130 to 165, wherein a stent prosthesis weight after removal of the at least one solvent is substantially the same after treatment as before treatment.

167. The biodegradable stent prosthesis of any of clauses 130 to 166, wherein a coating is disposed over at least a portion of said stent prosthesis.

168. The biodegradable stent prosthesis of any of clauses 130 to 167, wherein the coating comprises a drug.

169. The biodegradable stent prosthesis of any of clauses 130 to 168, wherein the coating comprises a drug and a polymer.

170. The biodegradable stent prosthesis of any of clauses 130 to 169, wherein the coating contours to structural element outer surfaces.

171. The biodegradable stent prosthesis of any of clauses 130 to 170, wherein the coating thickness ranges between 0.5 and 10 micrometer, preferably ranges between 1 micrometer and 7 micrometer, and most preferably ranges between 1 micrometer and 5 micrometer.

172. The biodegradable stent prosthesis of any of clauses 130 to 170, wherein the coating does not substantially change the surface area of the structural elements.

173. The biodegradable stent prosthesis of any of clauses 130 to 171, wherein the coating surface area changes the surface area of the structural element by less than 10%.

174. The biodegradable stent prosthesis of any of clauses 130 to 173, wherein the thickness of a structural element is measured between the abluminal and luminal surfaces, and the width of said structural element is measured between the side surfaces of said structural element.

175. The biodegradable stent prosthesis of any of clauses 130 to 174, wherein the treatment comprises heating the stent prosthesis after patterning to a temperature ranging between 50° C. and 180° C.

176. The biodegradable stent prosthesis of any of clauses 130 to 175, wherein the treatment comprises heating the stent prosthesis after patterning to 30° C. to 100° C. above the Tg of said polymeric material.

177. The biodegradable stent prosthesis of any of clauses 130 to 176, wherein the heating is for a time between 1 minute and 5 hours, preferably between 5 minutes and 4 hours.

178. The biodegradable stent prosthesis of any of clauses 130 to 177, wherein the stent prosthesis is crimped to the crimped configuration having a smaller diameter than the initial diameter at which the stent is formed.

179. The biodegradable stent prosthesis of any of clauses 130 to 178, wherein the stent prosthesis in the expanded configuration does not fracture.

180. The biodegradable stent prosthesis of any of clauses 130 to 179, wherein patterned diameter of the stent prosthesis is 1.1-1.5 times an intended deployed diameter of the stent, and wherein the stent at the intended deployed diameter does not fracture.

181. The biodegradable stent prosthesis of any of clauses 130 to 180, wherein the polymeric material crystallinity after treatment increases by at least 10% or by at least 20%.

182. The biodegradable stent prosthesis of any of clauses 130 to 181, wherein the polymeric material crystallinity after treatment ranges between 5% and 50%, preferably ranges between 5% and 30%.

183. The biodegradable stent prosthesis of any of clauses 130 to 182, wherein the elastic modulus of the stent prosthesis ranges between 0.35 GPa and 1.5 GPa.

184. The biodegradable stent prosthesis of any of clauses 130 to 182, wherein the tubular body is formed from a substantially continuous polymeric tube.

185. The biodegradable stent prosthesis of any of clauses 130 to 184, wherein the treatment is performed to change the shape of at least some structural elements wherein said structural elements have an abluminal surface, a luminal surface, and two side surfaces, said treatment changes the shape of said abluminal surfaces to a shape that is substantially concave or convex across the width of said abluminal surface.

186. The biodegradable stent prosthesis of any of clauses 130 to 185, wherein the treatment is performed to change the shape of at least some structural elements wherein said treatment changes the shape of said side surface regions from being substantially flat or straight to a shape that is convex across the sides of said structural elements.

187. The biodegradable stent prosthesis of any of clauses 130 to 186, wherein the treatment is performed to change the shape of at least some structural elements wherein said structural elements have an abluminal surface, a luminal surface, and two side surfaces, said treatment changes the shape of said abluminal surfaces and side surfaces; to a bulbous shape extending between the abluminal surface region and the luminal surface region of said structural elements.

188. The biodegradable stent prosthesis of any of clauses 130 to 187, wherein the structural elements shapes are viewed and/or measured using a cross section of said structural element, or using part or all of a structural element.

189. The biodegradable stent prosthesis of any of clauses 130 to 188, wherein the structural elements shapes are viewed and/or measured using a using a two or three dimension viewing means.

190. The biodegradable stent prosthesis of any of clauses 130 to 189, wherein concave luminal and/or abluminal surface regions join convex side surface regions at lips which extend along at least some of the structural elements.

191. The expandable stent prosthesis of any of clauses 130 to 190, wherein the lip forms a thickest point of the structural element cross section.

192. The expandable stent prosthesis of any of clauses 130 to 191, wherein the lip is in the shape of a wave where the surface regions meet.

193. The expandable stent prosthesis of any of clauses 130 to 192, wherein the lips extend continuously along a strut and a connected crown of the expandable stent prosthesis.

194. The expandable stent prosthesis of any of clauses 130 to 193, wherein the stent prosthesis cross section has concave luminal and/or abluminal surface regions and convex side surface regions which form a continuous curve across the side surface regions to provide a continuous convex curve in the form of an arc which extends between abluminal and luminal lips.

195. The expandable stent prosthesis of any of clauses any of clauses 130 to 194, wherein at least some abluminal surface regions and at least some luminal surface regions join said side surface regions at a lip and a thickness between an abluminal lip and a luminal lip forms a thickest part of the cross section of said structural elements, while a thickness at a core or substantially a midpoint between the abluminal lips forms a thinnest part of the cross section of said structural elements.

196. The expandable stent prosthesis of any of clauses any of clauses 130 to 195, wherein the structural elements prior to treatment and following treatment are substantially free from pits, holes or grooves.

197. The expandable stent prosthesis of any of clauses 130 to 196, wherein the structural elements have a substantially square or rectangular cross section before treatment which becomes a non-square or non-rectangular cross section after treatment.

198. The expandable stent prosthesis of any of clauses 130 to 197, wherein the prosthesis further comprises a metallic biodegradable material 199. The expandable stent prosthesis of clause 198, wherein the biodegradable metallic material comprises metal or metal alloy.

In embodiments of the disclosure according to any of the above clauses, at least some of the stent structural elements are elongate and have a similar cross-section along their length or at least along a major portion of their length. In embodiments of the disclosure according to any of the above clauses, at least some of the stent structural elements have the same cross-section along their length or at least along a major portion of their length. The cross-sections of different stent structural elements may be the same, similar or different.

What is claimed is:

1. A biodegradable stent prosthesis comprising a polymeric material, said stent comprising structural elements which have abluminal, luminal and side surface regions, said structural elements comprising struts joined by crowns wherein at least some structural elements have convex abluminal surface regions and substantially flat or substantially concave luminal surface regions, said abluminal surface region having said convex surface region on said structural elements in the absence of a coating on said structural elements, said stent prosthesis being expandable from a crimped configuration to an expanded larger configuration and having sufficient strength in the expanded configuration to support a body lumen.

2. The biodegradable stent prosthesis of claim 1, wherein the structural elements have substantially convex or substantially flat side surface regions.

3. The biodegradable stent prosthesis of claim 2, wherein the structural elements have a lip or a ledge between the abluminal and side surface regions or between the luminal and side surface regions.

4. The biodegradable stent prosthesis of claim 3, wherein the lip protrudes outwardly.

5. The biodegradable stent prosthesis of claim 1, wherein the structural elements are substantially smooth and substantially free from rough edges.

6. The biodegradable stent prosthesis of claim 1, wherein the thickness of said structural elements is greatest near a midpoint between the sides of said structural elements.

7. The biodegradable stent prosthesis of claim 1, wherein the width of said structural elements is greatest at about the center of said structural elements.

8. The biodegradable stent prosthesis of claim 1, said abluminal surface region having said convex surface region on said structural elements without the presence of a polymeric coating on said structural elements.

9. A biodegradable stent prosthesis comprising a polymeric material wherein the stent prosthesis has been formed from a tubular body having an initial diameter and the tubular body has been patterned into a stent with a patterned diameter, said stent comprising structural elements which have abluminal, luminal, and side surface regions, said structural elements comprising struts joined by crowns wherein said structural elements have been treated to shape at least some structural elements to have convex abluminal surface regions and substantially flat or substantially concave luminal surface regions, the weight of said stent prosthesis before said treatment and after said treatment is substantially the same, said stent prosthesis being expandable from a crimped configuration to an expanded larger configuration and having sufficient strength in the expanded configuration to support a body lumen.

10. The biodegradable stent prosthesis of claim 9, wherein the structural elements have substantially convex or substantially flat side surface regions.

11. The biodegradable stent prosthesis of claim 9, wherein the structural elements have been shaped by the treatment after patterning, said treating comprising one or more of chemical treatment, heating, mechanical shaping, laser shaping, or blasting.

12. The biodegradable stent prosthesis of claim 11, where the treatment comprises chemical treatment of said patterned stent with at least one solvent.

13. The biodegradable stent prosthesis of claim 12, wherein said weight after treatment is after the removal of substantially all solvent.

14. The biodegradable stent prosthesis of claim 11, where the treatment comprises chemical treatment of said patterned stent with at least one solvent which can dissolve the polymeric material and a second solvent which does not substantially dissolve the polymeric material.

15. The biodegradable stent prosthesis of claim 14, wherein the treatment with the first solvent ranges from 0.5 seconds to 5 seconds and the second solvent treatment ranges from 0.5 seconds to 60 seconds.

16. The biodegradable stent prosthesis of claim 14, where the treatment with the two solvents does not substantially dissolve the polymeric material.

17. The biodegradable stent prosthesis of claim 14, wherein a stent prosthesis weight after removal of the solvents is substantially the same after treatment as before treatment.

18. The biodegradable stent prosthesis of claim 14, wherein the solvent treatment redistributes the polymeric material to change the shape of at least some structural elements.

19. The biodegradable stent prosthesis of claim 9, wherein the structural elements have an initial shape and the treatment changes the shape of said structural elements.

20. The expandable stent prosthesis of claim 19, wherein the initial shape of said structural elements is substantially square or rectangular cross section before treatment which becomes a non-square or non-rectangular cross section after treatment.

21. The biodegradable stent prosthesis of claim 9, wherein the tubular body has been formed using extrusion, spraying, dipping, molding, or printing.

22. The biodegradable stent prosthesis of claim 9, wherein the tubular body has been exposed to an additional treatment before patterning, said additional treatment comprises at least one or more of heating, cooling, pressurizing the polymeric material, or chemically treating the polymeric material.

23. The biodegradable stent prosthesis of claim 9, wherein the treatment changes the thickness or width of at least some of the structural elements.

24. The biodegradable stent prosthesis of claim 9, wherein the thickness is larger after treatment.

25. The biodegradable stent prosthesis of claim 24, wherein the thickness changes after treatment by from 2 micrometer to 35 micrometer.

26. The biodegradable stent prosthesis of claim 9, wherein the width of at least some of said structural elements is decreased after treatment.

27. The biodegradable stent prosthesis of claim 26, wherein the width changes after treatment by from 2 micrometer to 35 micrometer.

28. The biodegradable stent prosthesis of claim 9, wherein the initial and patterned diameters are the same.

29. The biodegradable stent prosthesis of claim 9, wherein the tubular body is formed at an initial diameter, patterned at substantially at the initial diameter and the treatment of said structural elements after patterning does not substantially change the initial diameter of said tubular body.

30. The biodegradable stent prosthesis of claim 9, wherein the treatment of said structural elements does not change the stent pattern or stent geometry.

31. The biodegradable stent prosthesis of claim 9, wherein the stent prosthesis is heated one or more times after patterning and before crimping to a temperature ranging between 70° C. and 150° C. without substantially changing the pattern, diameter or geometry of the stent.

32. The biodegradable stent prosthesis of claim 31, wherein the heating one or more times after patterning is to a temperature ranging between 90° C. and 120° C.

33. The biodegradable stent prosthesis of claim 32, wherein the stent prosthesis is crimped to the crimped configuration having a smaller diameter than the initial diameter at which the stent is formed.

34. The biodegradable stent prosthesis of claim 31, wherein the heating is for a time between 1 minute and 5 hours.

35. The biodegradable stent prosthesis of claim 31, wherein the polymeric material crystallinity after heat treatment increases by at least 10% or by at least 20%.

36. The biodegradable stent prosthesis of claim 31, wherein the polymeric material crystallinity after heat treatment ranges between 5% and 50%.

37. The biodegradable stent prosthesis of claim 9, wherein the stent prosthesis is heated after patterning to 30° C. to 100° C. above the Tg of said polymeric material.

38. The biodegradable stent prosthesis of claim 37, wherein the crimping temperature is about 40° C. to about 55° C.

39. The biodegradable stent prosthesis of claim 9, wherein patterned diameter of the stent prosthesis is 1.1-1.5 times an intended deployed diameter of the stent.

40. The expandable stent prosthesis of claim 9, wherein the structural elements prior to treatment and following treatment are substantially free from pits, holes or grooves.

41. The biodegradable stent prosthesis of claim 9, wherein said weight after treatment is after the removal of substantially all treatment material.

42. The biodegradable stent prosthesis of claim 9, wherein said weight after treatment is after the removal of substantially all non-polymeric material.

43. The biodegradable stent prosthesis of claim 9, wherein the maximum width of at least some structural elements is smaller after said treatment than before said treatment.

44. A biodegradable stent prosthesis comprising a polymeric material, said stent comprising structural elements which have abluminal, luminal and side surface regions, said structural elements comprising struts joined by crowns wherein at least some structural elements have convex abluminal surface regions and substantially flat or concave luminal surface regions and, wherein said convex abluminal surface region has a concave section located at about the mid-point between the side surfaces, said side surface regions extending between the abluminal and luminal surface regions in a continuous convex curve or substantially flat contour, said stent prosthesis being expandable from a crimped configuration to an expanded larger configuration and having sufficient strength at the expanded configuration to support a body lumen.

45. The expandable biodegradable stent prosthesis of claim 44 which has been formed as a tubular body and patterned into a stent prosthesis.

46. The biodegradable stent prosthesis of claim 45, wherein the tubular body is formed from a substantially continuous polymeric tube.

47. A biodegradable stent prosthesis comprising a polymeric material, said stent comprising structural elements which have abluminal, luminal and side surface regions, said structural elements comprising struts joined by crowns wherein at least some structural elements have convex abluminal surface regions and substantially flat or substantially concave luminal surface regions, said stent having a coating which substantially contours to and substantially maintains the convex shape of the abluminal surface region of said structural elements, said stent prosthesis being expandable from a crimped configuration to an expanded larger configuration and having sufficient strength in the expanded configuration to support a body lumen.

48. The biodegradable stent prosthesis of claim 1 or 47, wherein the abluminal surface region has an indentation between the two side surface regions.

49. The biodegradable stent prosthesis of claim 48, wherein the indentation is located at about the mid-point between said two side surface regions.

50. The biodegradable stent prosthesis of claim 49, wherein said indentation depth ranges from 1 to 50 micrometers in size.

51. The biodegradable stent prosthesis of claim 49, wherein greatest width of said indentation ranges from 1 to 50 micrometers in size.

52. The biodegradable stent prosthesis of claim 48, wherein the thickest portion of said structural elements is adjacent to said indentation.

53. The biodegradable stent prosthesis of claim 48, wherein there are two bumps along the abluminal surface region flanking the two sides of said indentation.

54. The biodegradable stent prosthesis of claim 53, wherein said bumps are asymmetrical in shape and size.

55. The biodegradable stent prosthesis of claim 1, 44 or 47, wherein said structural elements have convex side surface regions.

56. The biodegradable stent prosthesis of claim 1, 9, 44, or 47, wherein the flat or concave luminal surface regions join convex side surface regions at one or more lips which extend along at least some of the structural elements.

57. The biodegradable stent prosthesis of claim 1, 9, 44 or 47, wherein the polymeric material comprises at least one material selected from the group consisting of lactides, poly-DL-lactide, polylactide-co-glycolide, polylactide-co-polycaprolactone, poly (L-lactide-co-trimethylenecarbonate, polyhydroxybutyrate, polyhydroxyvalerate, poly orthoesters, poly anhydrides, polylactide, polyglycolides, polycaprolactone, tryrosine derived polycarbonates, polyiminocarbonates and copolymers thereof.

58. The biodegradable stent prosthesis of claim 1, 9, 44, or 47 wherein a coating is disposed over at least a portion of said stent prosthesis.

59. The biodegradable stent prosthesis of claim 58, wherein the coating comprises a drug.

60. The biodegradable stent prosthesis of claim 59, wherein the coating contours to struts and/or crowns outer surfaces without substantially changing their shape.

61. The biodegradable stent prosthesis of claim 58, wherein the coating comprises a drug and a polymer.

62. The biodegradable stent prosthesis of claim 1, 9, 44 or 47, wherein the elastic modulus of the stent prosthesis ranges between 0.35 GPa and 1.5 GPa.

63. The expandable stent prosthesis of claim 1, 9, 44 or 47, wherein the prosthesis further comprises a metallic biodegradable material.

64. The expandable stent prosthesis of claim 63, wherein the biodegradable metallic material comprises metal or metal alloy.

65. The biodegradable stent prosthesis of claim 9, 44 or 47, wherein the struts and/or crowns are substantially smooth and substantially free from rough edges.

66. The biodegradable stent prosthesis of claim 1 or 47, wherein said side surface regions extend between said abluminal and luminal surface regions in a continuous convex or substantially flat contour.

67. The biodegradable stent prosthesis of claim 1 or 47, wherein said structural elements are struts.

68. The biodegradable stent prosthesis of claim 47, wherein said coating substantially contours to and substantially maintains the shape of the surface regions of said structural elements.

* * * * *